United States Patent
Burstein et al.

(10) Patent No.: US 9,670,209 B2
(45) Date of Patent: Jun. 6, 2017

(54) MUSCARINIC AGONISTS

(71) Applicant: ACADIA Pharmaceuticals Inc., San Diego, CA (US)

(72) Inventors: Ethan S. Burstein, San Diego, CA (US); Jorgen Eskildsen, Copenhagen (DK); Roger Olsson, Bunkeflostrand (SE)

(73) Assignees: ACADIA PHARMACEUTICALS INC., San Diego, CA (US); ALLERGAN, INC., Irvine, CA (US)

( * ) Notice: Subject to any disclaimer, the term of this patent is extended or adjusted under 35 U.S.C. 154(b) by 0 days.

(21) Appl. No.: 14/774,685

(22) PCT Filed: Mar. 14, 2014

(86) PCT No.: PCT/US2014/026998
§ 371 (c)(1),
(2) Date: Sep. 10, 2015

(87) PCT Pub. No.: WO2014/152144
PCT Pub. Date: Sep. 25, 2014

(65) Prior Publication Data
US 2016/0039819 A1    Feb. 11, 2016

Related U.S. Application Data

(60) Provisional application No. 61/790,364, filed on Mar. 15, 2013.

(51) Int. Cl.
*A61K 31/46* (2006.01)
*C07D 471/08* (2006.01)
*C07D 451/06* (2006.01)

(52) U.S. Cl.
CPC ......... *C07D 471/08* (2013.01); *C07D 451/06* (2013.01)

(58) Field of Classification Search
USPC .............................. 514/230.5, 300, 304, 414
See application file for complete search history.

(56) References Cited

U.S. PATENT DOCUMENTS

| | | | |
|---|---|---|---|
| 6,627,645 B2 | 9/2003 | Andersson et al. | |
| 7,238,713 B2 | 7/2007 | Anderson et al. | |
| 7,550,459 B2* | 6/2009 | Skjaerbaek | C07D 401/04 514/230.5 |
| 2005/0209226 A1* | 9/2005 | Skjaerbaek | C07D 401/04 514/230.5 |

FOREIGN PATENT DOCUMENTS

| | | |
|---|---|---|
| EP | 1535912 A1 | 6/2005 |
| WO | 2004087158 A2 | 10/2004 |
| WO | 2014152144 A1 | 9/2014 |

OTHER PUBLICATIONS

Broadley et al., "Muscarinic Receptor Agonists and Antagonists," Molecules, vol. 6, No. 3, pp. 142-193 (2001).
Heinrich et al., "Phamacological comparison of muscarinic ligands: Historical versus more recent muscarinic M1—preferring receptor agonists," European Journal of Pharmacology, vol. 605, pp. 53-56 (2009).
The International Bureau of WIPO, International Preliminary Report on Patentability for PCT/US2014/026998 issued Sep. 15, 2015.

\* cited by examiner

*Primary Examiner* — Pancham Bakshi
(74) *Attorney, Agent, or Firm* — Jones Day

(57) ABSTRACT

Compounds of formula (I) and methods are provided for the treatment of disease or conditions in which modification of cholinergic, especially muscarinic receptor activity, has a beneficial effect.

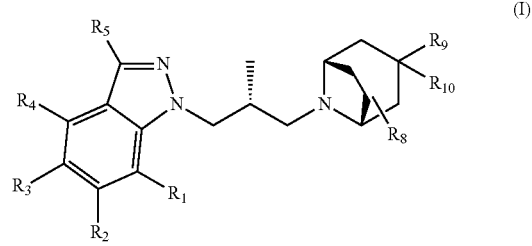

20 Claims, 2 Drawing Sheets

MUSCARINIC AGONISTS

CROSS REFERENCE TO RELATED APPLICATIONS

This application is a U.S. National Stage filing under 35 U.S.C. §371 of International Application No. PCT/US2014/026998, filed Mar. 14, 2014, which claims priority to U.S. Provisional Application No. 61/790,364, filed Mar. 15, 2013; the contents of each of which are incorporated herein by reference in their entireties.

FIELD

The present disclosure relates to the fields of chemistry and medicine. More particularly, the present disclosure relates to compounds that affect cholinergic receptors, especially muscarinic receptors, and methods of using such compounds for modulating conditions associated with muscarinic receptors.

BACKGROUND

Muscarinic cholinergic receptors mediate many of the actions of the neurotransmitter acetylcholine in the central and peripheral nervous systems, gastrointestinal system, heart, endocrine glands, lungs, and other tissues. Muscarinic receptors play a central role in the central nervous system for higher cognitive functions, as well as in the peripheral parasympathetic nervous system. Five distinct muscarinic receptor subtypes, referred to as subtypes $M_1$-$M_5$, have been identified. The $M_1$ subtype is the predominant subtype found in the cerebral cortex in hippocampus and is believed to be involved in the control of cognitive functions; the $M_2$ subtype is the predominant subtype found in heart and is believed to be involved in the control of heart rate; the $M_2$ subtype is also found in brain regions such as cortex and hippocampus where it is predominantly located presynaptically; the $M_3$ subtype is believed to be involved in gastrointestinal and urinary tract stimulation as well as sweating and salivation; the $M_4$ subtype is present in the brain and may be involved in locomotion; the $M_5$ receptor is present in the brain. $M_1$ and $M_4$ have been particularly associated with the dopaminergic system.

Pilocarpine is a pharmaceutical that has been used to treat glaucoma and to prevent other eye diseases and symptoms thereof. Pilocarpine is recognized as a non-selective muscarinic receptor agonist, and can cause unwanted side effects. Accordingly, there is a need for compounds, such as selective muscarinic agonists, that can increase acetylcholine signaling and/or effect in the brain via activity at specific muscarinic receptor subtypes in the central and peripheral nervous system, both as pharmacological tools and as therapeutic agents.

SUMMARY

In one aspect the present disclosure relates to compounds of formula (I):

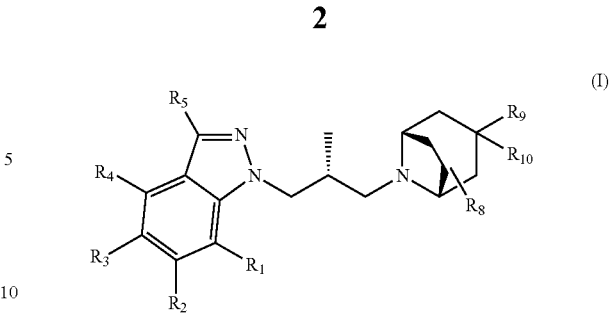

or pharmaceutically acceptable salts, hydrates, solvates, polymorphs, stereoisomers, and prodrugs thereof, wherein:
$R_1$, $R_2$, $R_3$, and $R_4$ are independently selected from a group consisting of hydrogen halogen; hydroxy; optionally substituted $C_{1-6}$ alkyl, optionally substituted $C_{2-6}$ alkenyl, optionally substituted $C_{2-6}$ alkynyl, optionally substituted $C_{1-6}$ alkoxy, optionally substituted $C_{1-6}$ heteroalkyl,
$R_5$ is selected from the group consisting of hydrogen; halogen; hydroxy optionally substituted $C_{1-6}$ alkyl, optionally substituted $C_{2-6}$ alkenyl, optionally substituted $C_{2-6}$ alkynyl, and optionally substituted $C_{1-6}$ alkoxy;
$R_8$ is present 0, 1, or 2 times and is independently selected from the group consisting of halogen, hydroxy, optionally substituted $C_{1-6}$ alkyl, and optionally substituted O—$C_{1-6}$ alkyl; and $R_9$ is selected from the group consisting of optionally substituted $C_{1-6}$ alkoxy, optionally substituted $C_{1-6}$ alkoxy-$C_{1-6}$ alkyl, optionally substituted $C_{2-6}$ alkenyl, optionally substituted $C_{2-6}$ alkynyl, optionally substituted $C_{2-6}$ alkenyloxy, optionally substituted $C_{2-6}$ alkynyloxy, optionally substituted $C_{1-6}$ heteroalkyl, optionally substituted $C_{3-6}$ cycloalkyl-$C_{1-6}$ alkyl, optionally substituted $C_{3-6}$ cycloalkenyl-$C_{1-6}$ alkyl, optionally substituted $C_{3-6}$ cycloalkyloxy; and
$R_{10}$ is hydrogen;
or $R_9$ and $R_{10}$ together form an optionally substituted $C_{1-6}$ alkoxy $C_{1-6}$ alkylidene.

In one aspect the present application relates to a pharmaceutical composition, comprising an effective amount of a compound according to Formula (I) or a pharmaceutically acceptable salt, hydrate, solvate, polymorph, or prodrug thereof.

In one aspect the present application relates to a method of increasing an activity of a muscarinic receptor, comprising contacting the muscarinic receptor or a system containing the muscarinic receptor with an effective amount of at least one compound according to Formula (I) or a pharmaceutical composition comprising a compound of Formula (I).

One aspect relates to a method of treating a disease or condition associated with a muscarinic receptor comprising administering to a subject in need of such treatment an effective amount of at least one compound according to Formula (I) or a pharmaceutical composition comprising a compound of Formula (I). In one aspect the disease or condition is selected from the group consisting of cognitive dysfunctions such as cognitive impairment, forgetfulness, confusion, memory loss, depression, attentional deficits, deficits in visual perception, and cognitive dysfunctions associated with mental disorders such as neuropsychiatric disorders, neurodegenerative disorders, dementia, age-related cognitive decline, and Down's syndrome; neuropsychiatric disorders such as sleep disorders, depression, psychosis, hallucinations, aggressiveness, paranoia, schizophrenia, attention deficit disorders, and Gilles de la Tourette's syndrome; eating disorders such as anorexia nervosa and bulimia; anxiety disorders such as obsessive compulsive disorders, panic disorders, phobic disorders, general anxiety disorders, and posttraumatic stress disorders; mood disorders, such as clinical depression, bipolar disorder, and major depressive disorder; neurodegenerative disorders and conditions such as alcoholism, Alzheimer's disease, amyotrophic lateral sclerosis, frontotemporal lobar degeneration, Huntington's disease, HIV-associated dementia, Lewy body dementia, multiple sclerosis, Parkinson's disease, Pick's disease, and progressive supranuclear palsy; and other diseases and disorders such as pain, such as neuropathic pain; increased intraocular pressure, glaucoma, ocular hypertension, dry eye, blepharitis and meibomian gland disease, restore corneal sensitivity that has been impaired due to surgery on the cornea or other surface of the eye, allergic conjunctivitis and atopic and vernal keratoconjunctivitis, ptyregia, ocular symptoms of graft versus host disease, ocular allergy, atopic keratoconjunctivitis, vernal keratoconjunctivitis, uveitis, anterior uveitis, Behcet's disease, Sjogren's syndrome, Stevens-Johnson syndrome, ocular cicatricial pemphigoid, chronic ocular surface inflammation caused by viral infection, herpes simplex keratitis, ocular rosacea, and pinguecula. In addition, the compounds disclosed herein may be used prevent corneal transplant rejection. Additionally the compounds disclosed herein may have neuroprotective effects and be used to treat age related macular degeneration, wet macular degeneration, dry macular degeneration, geographic atrophy, diabetic retinopathy, diabetic macular edema, tumors, retinal vein occlusion, optic neuropathy, ocular ischemic neuropathy, optic neuritis, retinitis pigmentosa and neuritis secondary to multiple sclerosis.

DETAILED DESCRIPTION

Definitions

Figure 1:
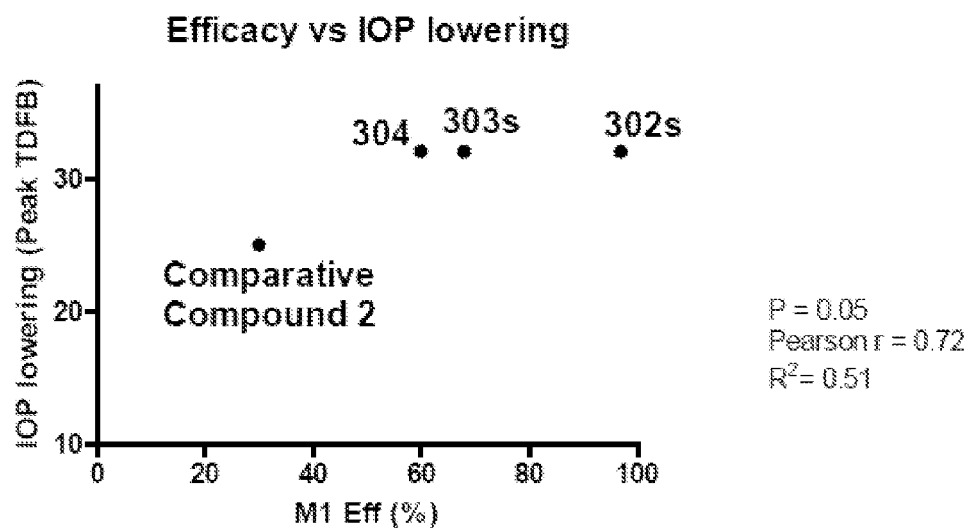
FIG. 1 illustrates the IOP lowering effect and efficacy in the GTPγS assay of compounds of disclosed herein compared to comparative compound 2.

Unless defined otherwise, all technical and scientific terms used herein have the same meaning as is commonly understood by one of ordinary skill in the art. All patents, applications, published applications and other publications referenced herein are incorporated by reference in their entirety. In the event that there are plurality of definitions for a term herein, those in this section prevail unless stated otherwise As used herein, any "R" group(s) such as, without limitation, $R_1$, $R_2$, $R_3$, $R_4$, $R_5$, $R_8$, $R_9$, and $R_{10}$, represent substituents that can be attached to the indicated atom. A non-limiting list of R groups include but are not limited to hydrogen, alkyl, alkenyl, alkynyl, cycloalkyl, cycloalkenyl, cycloalkynyl, aryl, heteroaryl, and heteroalicyclyl. An R group may be optionally substituted. If two "R" groups are covalently bonded to the same atom or to adjacent atoms, then they may be "taken together" as defined herein to form a cycloalkyl, aryl, heteroaryl or heteroalicyclyl group. For example, without limitation, if $R_a$ and $R_b$ of an $NR_aR_b$ group are indicated to be "taken together", it means that they are covalently bonded to one another at their terminal atoms to form a ring that includes the nitrogen:

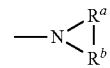

As used herein, "$IC_{50}$" refers to an amount, concentration, or dosage of a particular test compound that achieves a 50% inhibition of a maximal response in an assay that measures such response. The assay may be an R-SAT® assay as described herein but is not limited to an RSAT assay.

As used herein, "$EC_{50}$" refers to an amount, concentration, or dosage of a particular test compound that elicits a dose-dependent response at 50% of maximal expression of a particular response that is induced, provoked or potentiated by the particular test compound, in an assay that measures such response such as but not limited to R-SAT® assay described herein.

Whenever a group is described as being "optionally substituted" that group may be unsubstituted or substituted with one or more of the indicated substituents. When the group is substituted, the group may be mono-substituted or poly-substituted. When the group is described as being "mono-substituted," the group is only substituted with one substitutent. When the group is described as being "poly-substituted," the group may have two or more substitutents, and each substitutent may be independently selected from any of the indicated substituents. Likewise, when a group is described as being "unsubstituted or substituted," if substituted, the substituent(s) may be independently selected from one or more of the indicated substituents.

Unless otherwise indicated, when a substituent is deemed to be "optionally substituted," the substitutent itself may be unsubstituted or substituted with one ore more of the indicated substitutents. When the referenced substituent is substituted, it is meant that one or more hydrogen atoms on the referenced group may be replaced with a group(s) individually and independently selected from alkyl, alkenyl, alkynyl, cycloalkyl, cycloalkenyl, cycloalkynyl, aryl, heteroaryl, heteroalicyclyl, aralkyl, heteroaralkyl, (heteroalicyclyl)alkyl, hydroxy, alkoxy, mercapto, alkylthio, cyano, halogen, nitro, haloalkyl, haloalkoxy, and amino, including mono- and di-substituted amino groups, and the protected derivatives thereof. The protecting groups that may form the protective derivatives of the above substituents are known to those of skill in the art and may be found in references Greene and Wuts, Protective Groups in Organic Synthesis, 3$^{rd}$ Ed., John Wiley & Sons, New York, N.Y., 1999, which is hereby incorporated by reference in its entirety.

As used herein, "$C_m$ to $C_n$," "$C_m$-$C_n$" or "$C_m$," in which "m" and "n" are integers refers to the number of carbon atoms in the relevant group. That is, the group can contain from "m" to "n", inclusive, carbon atoms. Thus, for example, a "$C_1$ to $C_4$ alkyl" group refers to all alkyl groups having from 1 to 4 carbons, that is, $CH_3$—, $CH_3CH_2$—, $CH_3CH_2CH_2$—, $(CH_3)_2CH$—, $CH_3CH_2CH_2CH_2$—, $CH_3CH_2CH(CH_3)$— and $(CH_3)_3C$—. If no "m" and "n" are designated with regard to a group, the broadest range described in these definitions is to be assumed.

As used herein, "alkyl" refers to a straight or branched hydrocarbon chain fully saturated (no double or triple bonds) hydrocarbon group. The alkyl group may have 1 to 20 carbon atoms (whenever it appears herein, a numerical range such as "1 to 20" refers to each integer in the given range; e.g., "1 to 20 carbon atoms" means that the alkyl group may consist of 1 carbon atom, 2 carbon atoms, 3 carbon atoms, etc., up to and including 20 carbon atoms, although the present definition also covers the occurrence of the term "alkyl" where no numerical range is designated). The alkyl group may also be a medium size alkyl having 1 to 10 carbon atoms. The alkyl group could also be a lower alkyl having 1 to 5 carbon atoms. The alkyl group of the compounds may be designated as "$C_1$-$C_4$ alkyl," "$C_{1-4}$ alkyl" or similar designations. By way of example only, "$C_1$-$C_4$ alkyl" or "$C_{1-4}$ alkyl" indicates that there are one to four carbon atoms in the alkyl chain, i.e., the alkyl chain is selected from the group consisting of methyl, ethyl, propyl, iso-propyl, n-butyl, iso-butyl, sec-butyl, and t-butyl. Typical alkyl groups include, but are in no way limited to, methyl, ethyl, propyl, isopropyl, butyl, isobutyl, tertiary butyl, pentyl, hexyl, ethenyl, propenyl, butenyl, and the like.

The alkyl group may be optionally substituted. When substituted, the substituent group(s) is(are) one or more group(s) individually and independently selected from alkenyl, alkynyl, cycloalkyl, cycloalkenyl, cycloalkynyl, aryl, heteroaryl, heteroalicyclyl, aralkyl, heteroaralkyl, (heteroalicyclyl)alkyl, hydroxy, alkoxy, mercapto, alkylthio, cyano, halogen, nitro, haloalkyl, haloalkoxy, and amino, including mono- and di-substituted amino groups, and the protected derivatives thereof As used herein, "alkenyl" refers to an alkyl group that contains in the straight or branched hydrocarbon chain one or more double bonds. An alkenyl group may be unsubstituted or substituted. When substituted, the substituent(s) may be selected from the same groups disclosed above with regard to alkyl group substitution.

As used herein, "alkynyl" refers to an alkyl group that contains in the straight or branched hydrocarbon chain one or more triple bonds. An alkynyl group may be unsubstituted or substituted. When substituted, the substituent(s) may be selected from the same groups disclosed above with regard to alkyl group substitution.

As used herein, "hetero" may be attached to a group and refers to one or more carbon atom(s) and the associated hydrogen atom(s) in the attached group have been independently replace with the same or different heteroatoms selected from nitrogen, oxygen and sulfur. When $C_{m-n}$ or $C_m$-$C_n$ is also indicated, it means that one or more carbon atom(s) and the associated hydrogen atom(s) in the $C_{m-n}$ or $C_m$-$C_n$ group have been independently replace with the same or different heteroatoms selected from nitrogen, oxygen and sulfur.

As used herein, "heteroalkyl," by itself or in combination with another term, refers to a straight or branched alkyl group consisting of the stated number of carbon atoms, where one or more carbon atom(s), such as 1, 2, 3 or 4 carbon atom(s), and the associated hydrogen atom(s) have been independently replaced with the same or different heteroatoms selected from nitrogen, oxygen and sulfur. The carbon atom(s) being replace may be in the middle or at the end of the alkyl group. Examples of heteroalkyl include, but not limited to, —S— alkyl, —O-alkyl, —NH-alkyl, alkyl-O-alkyl, etc As used herein, "aryl" refers to a carbocyclic (all carbon) ring or two or more fused rings (rings that share two adjacent carbon atoms) that have a fully delocalized pi-electron system. Examples of aryl groups include, but are not limited to, benzene, naphthalene and azulene. An aryl group may be optionally substituted. When substituted, hydrogen atoms are replaced by substituent group(s) that is(are) one or more group(s) independently selected from alkyl, alkenyl, alkynyl, cycloalkyl, cycloalkenyl, cycloalkynyl, aryl, heteroaryl, heteroalicyclyl, aralkyl, heteroaralkyl, (heteroalicyclyl)alkyl, hydroxy, alkoxy, aryloxy, acyl, ester, mercapto, alkylthio, arylthio, cyano, halogen, carbonyl, thiocarbonyl, C-amido, N-amido, S-sulfonamido, N-sulfonamido, nitro, silyl, sulfenyl, sulfinyl, sulfonyl, haloalkyl, haloalkoxy, trihalomethanesulfonyl, trihalomethanesulfonamido, and amino, including mono- and di-substituted amino groups, and the protected derivatives thereof. When substituted, substituents on an aryl group may form a non-aromatic ring fused to the aryl group, including a cycloalkyl, cycloalkenyl, cycloalkynyl, and heterocyclyl.

As used herein, "heteroaryl" refers to a monocyclic or multicyclic aromatic ring system (a ring system with fully delocalized pi-electron system), one or two or more fused rings that contain(s) one or more heteroatoms, that is, an element other than carbon, including but not limited to, nitrogen, oxygen and sulfur. Examples of heteroaryl rings include, but are not limited to, furan, thiophene, phthalazine, pyrrole, oxazole, thiazole, imidazole, pyrazole, isoxazole, isothiazole, triazole, thiadiazole, pyridine, pyridazine, pyrimidine, pyrazine and triazine. A heteroaryl group may be optionally substituted. When substituted, hydrogen atoms are replaced by substituent group(s) that is(are) one or more group(s) independently selected from alkyl, alkenyl, alkynyl, cycloalkyl, cycloalkenyl, cycloalkynyl, aryl, heteroaryl, heteroalicyclyl, aralkyl, heteroaralkyl, (heteroalicyclyl)alkyl, hydroxy, alkoxy, aryloxy, acyl, ester, mercapto, alkylthio, arylthio, cyano, halogen, carbonyl, thiocarbonyl, C-amido, N-amido, S-sulfonamido, N-sulfonamido, nitro, silyl, sulfenyl, sulfinyl, sulfonyl, haloalkyl, haloalkoxy, trihalomethanesulfonyl, trihalomethanesulfonamido, and amino, including mono- and di-substituted amino groups, and the protected derivatives thereof. When substituted, substituents on a heteroayl group may form a non-aromatic ring fused to the aryl group, including a cycloalkyl, cycloalkenyl, cycloalkynyl, and heterocyclyl.

An "aralkyl" or "arylalkyl" is an aryl group connected, as a substituent, via an alkylene group. The alkylene and aryl group of an aralkyl may be optionally substituted. Examples include but are not limited to benzyl, substituted benzyl, 2-phenylethyl, 3-phenylpropyl, and naphtylalkyl. In some cases, the alkylene group is a lower alkylene group.

A "heteroaralkyl" or "heteroarylalkyl" is heteroaryl group connected, as a substituent, via an alkylene group. The alkylene and heteroaryl group of heteroaralkyl may be optionally substituted. Examples include but are not limited to 2-thienylmethyl, 3-thienylmethyl, furylmethyl, thienylethyl, pyrrolylalkyl, pyridylalkyl, isoxazollylalkyl, and imidazolylalkyl, and their substituted as well as benzo-fused analogs. In some cases, the alkylene group is a lower alkylene group.

"Lower alkylene groups" are straight-chained tethering groups, forming bonds to connect molecular fragments via their terminal carbon atoms. Examples include but are not limited to methylene (—$CH_2$—), ethylene (—$CH_2CH_2$—), propylene (—$CH_2CH_2CH_2$—), and butylene (—$(CH_2)_4$—) groups. A lower alkylene group may be optionally substituted.

As used herein, "heteroalkylene" by itself or in combination with another term refers to an alkylene group consisting of the stated number of carbon atoms in which one or more of the carbon atoms, such as 1, 2, 3 or 4 carbon atom(s), are independently replaced with the same or different heteroatoms selected from oxygen, sulfur and nitrogen. Examples of heteroalkylene include, but not limited to —CH$_2$—O—, —CH$_2$—CH$_2$—O—, —CH$_2$—CH$_2$—CH$_2$—O—, —CH$_2$—NH—, —CH$_2$—CH$_2$—NH—, —CH$_2$—CH$_2$—CH$_2$—NH—, —CH$_2$—CH$_2$—NH—CH$_2$—, —O—CH$_2$—CH$_2$—O—CH$_2$—CH$_2$—O—, —O—CH$_2$—CH$_2$—O—CH$_2$—CH$_2$—, and the like As used herein, "alkylidene" refers to a divalent group, such as =CR'R", which is attached to one carbon of another group, forming a double bond, Alkylidene groups include, but are not limited to, methylidene (=CH$_2$) and ethylidene (=CHCH$_3$). As used herein, "arylalkylidene" refers to an alkylidene group in which either R' and R" is an aryl group. An alkylidene group may be optionally substituted.

As used herein, "alkoxy" refers to the formula —OR wherein R is an alkyl is defined as above, e.g. methoxy, ethoxy, n-propoxy, 1-methylethoxy(isopropoxy), n-butoxy, iso-butoxy, sec-butoxy, tert-butoxy, amoxy, tert-amoxy and the like. An alkoxy may be optionally substituted.

As used herein, "alkylthio" refers to the formula —SR wherein R is an alkyl is defined as above, e.g. methylmercapto, ethylmercapto, n-propylmercapto, 1-methylethylmercapto (isopropylmercapto), n-butylmercapto, iso-butylmercapto, sec-butylmercapto, tert-butylmercapto, and the like. An alkylthio may be optionally substituted.

As used herein, "aryloxy" and "arylthio" refers to RO— and RS—, in which R is an aryl as defined above, e.g., phenoxy, naphthalenyloxy, azulenyloxy, anthracenyloxy, naphthalenylthio, phenylthio and the like. Both an aryloxy and arylthio may be optionally substituted.

As used herein, "alkenyloxy" refers to the formula —OR wherein R is an alkenyl as defined above, e.g., vinyloxy, propenyloxy, n-butenyloxy, iso-butenyloxy, sec-pentenyloxy, tert-pentenyloxy, and the like. The alkenyloxy may be optionally substituted.

As used herein, "acyl" refers to a hydrogen, alkyl, alkenyl, alkynyl, or aryl connected, as substituents, via a carbonyl group. Examples include formyl, acetyl, propanoyl, benzoyl, and acryl. An acyl may be optionally substituted. An acyl may be optionally substituted.

As used herein, "cycloalkyl" refers to a completely saturated (no double bonds) mono- or multi-cyclic hydrocarbon ring system. When composed of two or more rings, the rings may be joined together in a fused, bridged or spiro-connected fashion. Cycloalkyl groups may range from C$_3$ to C$_{10}$, in other embodiments it may range from C$_3$ to C$_6$. A cycloalkyl group may be unsubstituted or substituted. Typical cycloalkyl groups include, but are in no way limited to, cyclopropyl, cyclobutyl, cyclopentyl, cyclohexyl, and the like. If substituted, the substituent(s) may be an alkyl or selected from those indicated above with regard to substitution of an alkyl group unless otherwise indicated. When substituted, substituents on a cycloalkyl group may form an aromatic ring fused to the cycloalkyl group, including an aryl and a heteroaryl.

As used herein, "cycloalkenyl" refers to a cycloalkyl group that contains one or more double bonds in the ring although, if there is more than one, they cannot form a fully delocalized pi-electron system in the ring (otherwise the group would be "aryl," as defined herein). When composed of two or more rings, the rings may be connected together in a fused, bridged or spiro-connected fashion. A cycloalkenyl group may be unsubstituted or substituted. When substituted, the substituent(s) may be an alkyl or selected from the groups disclosed above with regard to alkyl group substitution unless otherwise indicated. When substituted, substituents on a cycloalkenyl group may form an aromatic ring fused to the cycloalkenyl group, including an aryl and a heteroaryl.

As used herein, "cycloalkynyl" refers to a cycloalkyl group that contains one or more triple bonds in the ring. When composed of two or more rings, the rings may be joined together in a fused, bridged or spiro-connected fashion. Cycloalkynyl groups may range from C$_3$ to C$_{10}$, in other embodiments it may range from C$_3$ to C$_6$. A cycloalkynyl group may be unsubstituted or substituted. When substituted, the substituent(s) may be an alkyl or selected from the groups disclosed above with regard to alkyl group substitution unless otherwise indicated. When substituted, substituents on a cycloalkynyl group may form an aromatic ring fused to the cycloalkynyl group, including an aryl and a heteroaryl.

As used herein, "heteroalicyclic" or "heteroalicyclyl" refers to a stable 3- to 18 membered ring which consists of carbon atoms and from one to five heteroatoms selected from the group consisting of nitrogen, oxygen and sulfur. The "heteroalicyclic" or "heteroalicyclyl" may be monocyclic, bicyclic, tricyclic, or tetracyclic ring system, which may be joined together in a fused, bridged or spiro-connected fashion; and the nitrogen, carbon and sulfur atoms in the "heteroalicyclic" or "heteroalicyclyl" may be optionally oxidized; the nitrogen may be optionally quaternized; and the rings may also contain one or more double bonds provided that they do not form a fully delocalized pi-electron system throughout all the rings. Heteroalicyclyl groups may be unsubstituted or substituted. When substituted, the substituent(s) may be one or more groups independently selected from the group consisting of alkyl, alkenyl, alkynyl, cycloalkyl, cycloalkenyl, cycloalkynyl, aryl, heteroaryl, heteroalicyclyl, aralkyl, heteroaralkyl, (heteroalicyclyl)alkyl, hydroxy, alkoxy, aryloxy, acyl, ester, mercapto, alkylthio, arylthio, cyano, halogen, C-amido, N-amido, S-sulfonamido, N-sulfonamido, isocyanato, thiocyanato, isothiocyanato, nitro, silyl, haloalkyl, haloalkoxy, trihalomethanesulfonyl, trihalomethanesulfonamido, and amino, including mono- and di-substituted amino groups, and the protected derivatives thereof. Examples of such "heteroalicyclic" or "heteroalicyclyl" include but are not limited to, azepinyl, dioxolanyl, imidazolinyl, morpholinyl, oxiranyl, piperidinyl N-Oxide, piperidinyl, piperazinyl, pyrrolidinyl, 4-piperidonyl, pyrazolidinyl, 2-oxopyrrolidinyl, thiamorpholinyl, thiamorpholinyl sulfoxide, and thiamorpholinyl sulfone. When substituted, substituents on a heteroalicyclyl group may form an aromatic ring fused to the heteroalicyclyl group, including an aryl and a heteroaryl.

A "(cycloalkyl)alkyl" is a cycloalkyl group connected, as a substituent, via an alkylene group. The alkylene and cycloalkyl of a (cycloalkyl)alkyl may be optionally substituted. Examples include but are not limited cyclopropylmethyl, cyclobutylmethyl, cyclopropylethyl, cyclopropylbutyl, cyclobutylethyl, cyclopropylisopropyl, cyclopentylmethyl, cyclopentylethyl, cyclohexylmethyl, cyclohexylethyl, cycloheptylmethyl, and the like. In some cases, the alkylene group is a lower alkylene group.

A "(cycloalkenyl)alkyl" is a cycloalkenyl group connected, as a substituent, via an alkylene group. The alkylene and cycloalkenyl of a (cycloalkenyl)alkyl may be optionally substituted. In some cases, the alkylene group is a lower alkylene group.

A "(cycloalkynyl)alkyl" is a cycloalkynyl group connected, as a substituent, via an alkylene group. The alkylene and cycloalkynyl of a (cycloalkynyl)alkyl may be optionally substituted. In some cases, the alkylene group is a lower alkylene group.

As used herein, "halo" or "halogen" refers to F (fluoro), Cl (chloro), Br (bromo) or I (iodo).

As used herein, "haloalkyl" refers to an alkyl group in which one or more of the hydrogen atoms are replaced by halogen. Such groups include but are not limited to, chloromethyl, fluoromethyl, difluoromethyl, trifluoromethyl and 1-chloro-2-fluoromethyl, 2-fluoroisobutyl. A haloalkyl may be optionally substituted.

As used herein, "haloalkoxy" refers to RO-group in which R is a haloalkyl group. Such groups include but are not limited to, chloromethoxy, fluoromethoxy, difluoromethoxy, trifluoromethoxy and 1-chloro-2-fluoromethoxy, 2-fluoroisobutyoxy. A haloalkoxy may be optionally substituted.

An "O-carboxy" group refers to a "RC(=O)O—" group in which R can be hydrogen, alkyl, alkenyl, alkynyl, cycloalkyl, cycloalkenyl, cycloalkynyl, aryl, heteroaryl, heteroalicyclyl, aralkyl, or (heteroalicyclyl)alkyl, as defined herein. An O-carboxy may be optionally substituted.

A "C-carboxy" group refers to a "—C(=O)OR" group in which R can be the same as defined with respect to O-carboxy. A C-carboxy may be optionally substituted A "trihalomethanesulfonyl" group refers to an "$X_3CSO_2$—" group wherein X is a halogen.

A "cyano" group refers to a "—CN" group.

A "cyanato" group reefers to an "—OCN" group.

An "isocyanato" group refers to a "—NCO" group.

A "thiocyanato" group refers to a "—SCN" group.

An "isothiocyanato" group refers to an "—NCS" group.

A "sulfinyl" group refers to an "—S(=O)—R" group in which R can be the same as defined with respect to O-carboxy. A sulfinyl may be optionally substituted.

A "sulfonyl" group refers to an "$SO_2R$" group in which R can be the same as defined with respect to O-carboxy. A sulfonyl may be optionally substituted.

An "S-sulfonamido" group refers to a "—$SO_2NR_AR_B$" group in which $R_A$ and $R_B$ can be the same as defined with respect to O-carboxy. An S-sulfonamido may be optionally substituted.

An "N-sulfonamido" group refers to a "$RSO_2N(R_A)$—" group in which R and $R_A$ can be the same as defined with respect to O-carboxy. A sulfonyl may be optionally substituted.

A "trihalomethanesulfonamido" group refers to an "$X_3CSO_2N(R)$—" group with X as halogen and R can be the same as defined with respect to O-carboxy. A trihalomethanesulfonamido may be optionally substituted.

A "C-amido" group refers to a "—$C(=O)NR_AR_B$" group in which $R_A$ and $R_B$ can be the same as defined with respect to O-carboxy. A C-amido may be optionally substituted.

An "N-amido" group refers to a "$RC(=O)NR_A$—" group in which R and $R_A$ can be the same as defined with respect to O-carboxy. An N-amido may be optionally substituted.

An "ester" refers to a "—C(=O)OR" group in which R can be the same as defined with respect to O-carboxy. An ester may be optionally substituted.

A lower aminoalkyl refers to an amino group connected via a lower alkylene group. A lower aminoalkyl may be optionally substituted.

A lower alkoxyalkyl refers to an alkoxy group connected via a lower alkylene group. A lower alkoxyalkyl may be optionally substituted.

Any unsubstituted or monosubstituted amine group on a compound herein can be converted to an amide, any hydroxyl group can be converted to an ester and any carboxyl group can be converted to either an amide or ester using techniques well-known to those skilled in the art (see, for example, Greene and Wuts, Protective Groups in Organic Synthesis, $3^{rd}$ Ed., John Wiley & Sons, New York, N.Y., 1999).

Where the numbers of substituents are not specified (e.g. haloalkyl), there may be one or more substituents present. For example "haloalkyl" may include one or more of the same or different halogens. As another example, "$C_1$-$C_3$ alkoxyphenyl" may include one or more of the same or different alkoxygroups containing one, two or three atoms.

As used herein, the abbreviations for any protective groups, amino acids and other compounds, are, unless indicated otherwise, in accord with their common usage, recognized abbreviations, or the IUPAC-IUB Commission on Biochemical Nomenclature (See, Biochem. 11:942-944 (1972)).

As employed herein, the following terms have their accepted meaning in the chemical literature.

AcOH acetic acid
anhyd anhydrous
$(BOC)_2O$ or $Boc_2O$ di-t-butyl dicarbonate
BOC or Boc t-butoxy carbonyl
$CDCl_3$ deuterated chloroform
CDI 1,1'-carbonyldiimidazole
$CH_3CN$ acetonitrile
$Cs_2CO_3$ Cesium carbonate
DCM dichloromethane or $CH_2Cl_2$
DIBAL-H diisobutylaluminum hydride
DIPEA N,N-diisopropylethylamine
DMF N,N-dimethylformamide
DMSO dimethyl sulfoxide
EDTA ethylenediaminetetraacetic acid
$Et_2O$ diethyl ether
$Et_3N$ triethyl amine
EtOAc ethyl acetate
EtOH ethanol
h hour(s)
HMDS hexamethyldisilazane
i-PrOH isopropanol
KOtBu potassium t-butoxide
MeOH methanol
MsCl mesyl chloride
MTBE methyl tert-butyl ether
$Na_2SO_4$ sodium sulphate
$NaHCO_3$ sodium bicarbonate
NaOEt sodium ethoxide
NaOH sodium hydroxide
NaOMe sodium methoxide
$NH_4OAc$ ammonium acetate
Pd/C palladium on activated carbon
$(Ph)_3P$ triphenylphosphine
rt room temperature
$SiO_2$ silicone dioxide/silica
TBAF tetra-n-butylammonium fluoride
TEA triethyl amine
TFA trifluoroacetic acid
THF tetrahydrofuran
TsCl tosyl chloride It is understood that, in any compound disclosed herein having one or more chiral centers, if an absolute stereochemistry is not expressly indicated, then each center may independently be of R-configuration or S-configuration or a mixture thereof. Thus, the compounds provided herein may be enatiomerically pure or be stereoisomeric mixtures. In addition, it is understood that in any compound having one or more double bond(s) generating geometrical isomers that can be defined as E or Z each double bond may independently be E or Z a mixture thereof. Likewise, all tautomeric forms are also intended to be included.

As used herein, "pharmaceutically acceptable salt" refers to a salt of a compound that does not abrogate the biological activity and properties of the compound. Pharmaceutical salts can be obtained by reaction of a compound disclosed herein with an acid or base. Base-formed salts include, without limitation, ammonium salt ($NH_4^+$); alkali metal, such as, without limitation, sodium or potassium, salts; alkaline earth, such as, without limitation, calcium or magnesium, salts; salts of organic bases such as, without limitation, dicyclohexylamine, N-methyl-D-glucamine, tris(hydroxymethyl)methylamine; and salts with the amino group of amino acids such as, without limitation, arginine and lysine. Useful acid-based salts include, without limitation, hydrochlorides, hydrobromides, sulfates, nitrates, phosphates, methanesulfonates, ethanesulfonates, p-toluenesulfonates and salicylates.

Pharmaceutically acceptable solvates and hydrates are complexes of a compound with one or more solvent of water molecules, or 1 to about 100, or 1 to about 10, or one to about 2, 3 or 4, solvent or water molecules.

As used herein, a "prodrug" refers to a compound that may not be pharmaceutically active but that is converted into an active drug upon in vivo administration. The prodrug may be designed to alter the metabolic stability or the transport characteristics of a drug, to mask side effects or toxicity, to improve the flavor of a drug or to alter other characteristics or properties of a drug. Prodrugs are often useful because they may be easier to administer than the parent drug. They may, for example, be bioavailable by oral administration whereas the parent drug is not. The prodrug may also have better solubility than the active parent drug in pharmaceutical compositions. An example, without limitation, of a prodrug would be a compound disclosed herein, which is administered as an ester (the "prodrug") to facilitate absorption through a cell membrane where water solubility is detrimental to mobility but which then is metabolically hydrolyzed to a carboxylic acid (the active entity) once inside the cell where water-solubility is beneficial. A further example of a prodrug might be a short peptide (polyaminoacid) bonded to an acid group where the peptide is metabolized in vivo to release the active parent compound. By virtue of knowledge of pharmacodynamic processes and drug metabolism in vivo, those skilled in the art, once a pharmaceutically active compound is known, can design prodrugs of the compound (see, e.g. Nogrady (1985) *Medicinal Chemistry A Biochemical Approach*, Oxford University Press, New York, pages 388-392)

As used herein, to "modulate" the activity of a receptor means either to activate it, i.e., to increase its cellular function over the base level measured in the particular environment in which it is found, or deactivate it, i.e., decrease its cellular function to less than the measured base level in the environment in which it is found and/or render it unable to perform its cellular function at all, even in the presence of a natural binding partner. A natural binding partner is an endogenous molecule that is an agonist for the receptor.

An "agonist" is defined as a compound that increases the basal activity of a receptor (i.e. signal transduction mediated by the receptor).

As used herein, "partial agonist" refers to a compound that has an affinity for a receptor but, unlike an agonist, when bound to the receptor it elicits only a fractional degree of the pharmacological response normally associated with the receptor even if a large number of receptors are occupied by the compound.

An "inverse agonist" is defined as a compound, which reduces, or suppresses the basal activity of a receptor, such that the compound is not technically an antagonist but, rather, is an agonist with negative intrinsic activity.

As used herein, "antagonist" refers to a compound that binds to a receptor to form a complex that does not give rise to any response, as if the receptor was unoccupied. An antagonist attenuates the action of an agonist on a receptor. An antagonist may bind reversibly or irreversibly, effectively eliminating the activity of the receptor permanently or at least until the antagonist is metabolized or dissociates or is otherwise removed by a physical or biological process.

As used herein, a "subject" refers to an animal that is the object of treatment, observation or experiment. "Animal" includes cold- and warm-blooded vertebrates and invertebrates such as fish, shellfish, reptiles and, in particular, mammals. "Mammal" includes, without limitation, mice; rats; rabbits; guinea pigs; dogs; cats; sheep; goats; cows; horses; primates, such as monkeys, chimpanzees, and apes, and, in particular, humans.

As used herein, a "patient" refers to a subject that is being treated by a medical professional such as an M.D. or a D.V.M. to attempt to cure, or at least ameliorate the effects of, a particular disease or disorder or to prevent the disease or disorder from occurring in the first place.

As used herein, a "carrier" refers to a compound that facilitates the incorporation of a compound into cells or tissues. For example, without limitation, dimethyl sulfoxide (DMSO) is a commonly utilized carrier that facilitates the uptake of many organic compounds into cells or tissues of a subject.

As used herein, a "diluent" refers to an ingredient in a pharmaceutical composition that lacks pharmacological activity but may be pharmaceutically necessary or desirable. For example, a diluent may be used to increase the bulk of a potent drug whose mass is too small for manufacture or administration. It may also be a liquid for the dissolution of a drug to be administered by injection, ingestion or inhalation. A common form of diluent in the art is a buffered aqueous solution such as, without limitation, phosphate buffered saline that mimics the composition of human blood.

As used herein, an "excipient" refers to an inert substance that is added to a pharmaceutical composition to provide, without limitation, bulk, consistency, stability, binding ability, lubrication, disintegrating ability etc., to the composition. A "diluent" is a type of excipient.

A "receptor" is intended to include any molecule present inside or on the surface of a cell that may affect cellular physiology when it is inhibited or stimulated by a ligand. Typically, a receptor comprises an extracellular domain with ligand-binding properties, a transmembrane domain that anchors the receptor in the cell membrane, and a cytoplasmic domain that generates a cellular signal in response to ligand binding ("signal transduction"). A receptor also includes any molecule having the characteristic structure of a receptor, but with no identifiable ligand. In addition, a receptor includes a truncated, modified, mutated receptor, or any molecule comprising partial or all of the sequences of a receptor.

"Ligand" is intended to include any substance that interacts with a receptor.

The "M1 receptor" is defined as a receptor having an activity corresponding to the activity of the M1 muscarinic receptor subtype characterized through molecular cloning and pharmacology.

"Selective" or "selectivity" is defined as a compound's ability to generate a desired response from a particular receptor type, subtype, class or subclass while generating less or little response from other receptor types. "Selective" or "selectivity" of one or more particular subtypes of a muscarinic agonist compound means a compound's ability to increase the activity of the subtypes while causing little or no increase in the activity of other subtypes.

As used herein, "coadministration" of pharmacologically active compounds refers to the delivery of two or more separate chemical entities, whether in vitro or in vivo. Coadministration means the simultaneous delivery of separate agents; the simultaneous delivery of a mixture of agents; as well as the delivery of one agent followed by delivery of a second agent or additional agents. Agents that are coadministered are typically intended to work in conjunction with each other.

The term "an effective amount" as used herein means an amount of active compound or pharmaceutical agent that elicits the biological or medicinal response in a tissue, system, animal or human that is being sought by a researcher, veterinarian, medical doctor or other clinician, which includes alleviation or palliation of the symptoms of the disease being treated.

Compounds

Disclosed herein are compounds that modulate cholinergic receptors, including muscarinic receptors. In some embodiments, the compounds are agonists of cholinergic receptors. In some embodiments, the compounds have therapeutic effect and can be used to treat disease or conditions such as cognitive dysfunctions such as cognitive impairment, forgetfulness, confusion, memory loss, depression, attentional deficits, deficits in visual perception, and cognitive dysfunctions associated with mental disorders such as neuropsychiatric disorders, neurodegenerative disorders, dementia, age-related cognitive decline, and Down's syndrome; neuropsychiatric disorders such as sleep disorders, depression, psychosis, hallucinations, aggressiveness, paranoia, schizophrenia, attention deficit disorders, and Gilles de la Tourette's syndrome; eating disorders such as anorexia nervosa and bulimia; anxiety disorders such as obsessive compulsive disorders, panic disorders, phobic disorders, general anxiety disorders, and posttraumatic stress disorders; mood disorders, such as clinical depression, bipolar disorder, and major depressive disorder; neurodegenerative disorders and conditions such as alcoholism, Alzheimer's disease, amyotrophic lateral sclerosis, frontotemporal lobar degeneration, Huntington's disease, HIV-associated dementia, Lewy body dementia, multiple sclerosis, Parkinson's disease, Pick's disease, and progressive supranuclear palsy; and other diseases and disorders such as pain, such as neuropathic pain; increased intraocular pressure, glaucoma, ocular hypertension and other ophthamological conditions such as ocular surface indications and conditions such as dry eye, blepharitis and meibomian gland disease, corneal sensitivity that has been impaired due to surgery on the cornea or other surface of the eye, allergic conjunctivitis and atopic and vernal keratoconjunctivitis, treat ptyregia, ocular symptoms of graft versus host disease, ocular allergy, atopic keratoconjunctivitis, vernal keratoconjunctivitis, uveitis, anterior uveitis, Behcet's disease, Sjogren's syndrome, Stevens-Johnson syndrome, ocular cicatricial pemphigoid, chronic ocular surface inflammation caused by viral infection, herpes simplex keratitis, ocular rosacea, and pinguecula. In addition, the compounds disclosed herein may be used prevent corneal transplant rejection. Additionally the compounds disclosed herein may have neuroprotective effects and be used to treat age related macular degeneration, wet macular degeneration, dry macular degeneration, geographic atrophy, diabetic retinopathy, diabetic macular edema, tumors, retinal vein occlusion, optic neuropathy, ocular ischemic neuropathy, optic neuritis, retinitis pigmentosa and neuritis secondary to multiple sclerosis.

These diseases/conditions are associated with the cholinergic receptors, such as the muscarinic receptors.

In some embodiments, the compounds disclosed herein have been optimized in order to have good solution stability, i.e. minimal base-catalyzed hydrolysis. Examples of such medical devices are dropper bottle of plastics such as low density polyethylene or polyethylene terephthalate. In some embodiments, the compounds disclosed herein have been developed to have a good systemic metabolic lability without losing ocular efficacy. This generally means that the compounds disclosed herein are easily metabolized once they leave the eye, improving the selectivity for ocular effects.

Consequently the embodiments and aspects disclosed herein includes compounds that have been designed to have targeted properties (such as those disclosed above) compared to other known muscarinic receptor agonists, for example those disclosed in WO2006/068904. The compounds herein are thus designed to be muscarinic receptor agonists.

In some embodiments the compounds are M1 agonists, which for example, is shown in Table 1. In some embodiments the compounds are M1 selective agonists. In some embodiments the compounds are M1 agonists with no or low M3 activity.

Some of the compounds disclosed herein have been assayed by for example R-SAT and GTPγS binding.

In some embodiments the compounds should have an M1 pEC50 value of at least 7.5, or at least 8.0, or at least 8.5 as assayed by R-SAT.

In some embodiments the compounds should have an M1 pEC50 value of at least 6.5, or at least 7.0, or at least 7.5 as assayed by GTPγS binding.

In some embodiments the compounds should have a EFF % (percent efficacy) of at least 25, such as at least 30, such as above 30, such as above 40, such as above 50, as assayed by GTPγS binding.

Some embodiment provides compounds of formula (I):

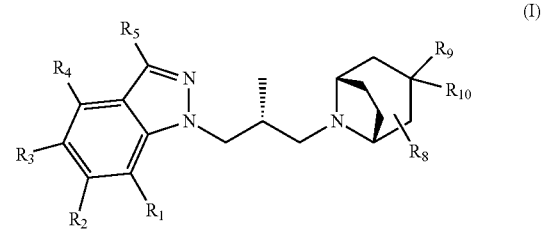

or pharmaceutically acceptable salts, hydrates, solvates, polymorphs, stereoisomers, and prodrugs thereof, wherein:

$R_1$, $R_2$, $R_3$, and $R_4$ are independently selected from a group consisting of hydrogen halogen, hydroxy, optionally substituted $C_{1-6}$ alkyl, optionally substituted $C_{2-6}$ alkenyl, optionally substituted $C_{2-6}$ alkynyl, optionally substituted $C_{1-6}$ alkoxy, optionally substituted $C_{1-6}$ heteroalkyl, $R_5$ is selected from the group consisting of hydrogen, halogen, hydroxy, optionally substituted $C_{1-6}$ alkyl, optionally substituted $C_{2-6}$ alkenyl, optionally substituted $C_{2-6}$ alkynyl, and optionally substituted $C_{1-6}$ alkoxy;

$R_8$ is present 0, 1, or 2 times and is independently selected from the group consisting of halogen, hydroxy, optionally substituted $C_{1-6}$ alkyl, and optionally substituted $O-C_{1-6}$alkyl; and $R_9$ is selected from the group consisting of optionally substituted $C_{1-6}$ alkoxy, optionally substituted $C_{1-6}$ alkoxy-$C_{1-6}$ alkyl, optionally substituted $C_{2-6}$ alkenyl, optionally substituted $C_{2-6}$ alkynyl, optionally substituted $C_{2-6}$ alkenyloxy, optionally substituted $C_{2-6}$ alkynyloxy, optionally substituted $C_{1-6}$ heteroalkyl, optionally substituted $C_{3-6}$ cycloalkyl-$C_{1-6}$ alkyl, optionally substituted $C_{3-6}$ cycloalkenyl-$C_{1-6}$ alkyl, optionally substituted $C_{3-6}$ cycloalkyloxy; and $R_{10}$ is hydrogen; or $R_9$ and $R_{10}$ together form an optionally substituted $C_{1-6}$ alkoxy $C_{1-6}$alkylidene.

In one embodiment the compound of formula (I) is selected from formula (Ia)

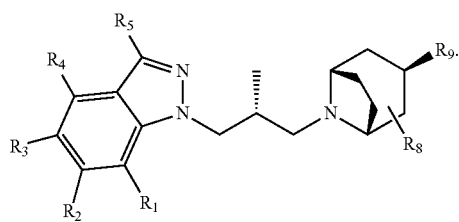

(Ia)

In some embodiments $R_1$, $R_2$, $R_3$, and $R_4$ are independently selected from a group consisting of hydrogen, halogen, optionally substituted $C_{1-6}$ alkyl, and optionally substituted $C_{1-6}$ alkoxy. In some embodiments, $R_1$, $R_2$, $R_3$, and $R_4$ are independently selected from a group consisting of hydrogen, halogen, $C_{1-6}$ alkyl substituted by halogen or hydroxy, and $C_{1-6}$ alkoxy.

In some embodiments, $R_4$ is hydrogen, and $R_1$, $R_2$, and $R_3$ are independently selected from a group consisting of hydrogen, halogen, optionally substituted $C_{1-6}$ alkyl, and optionally substituted $C_{1-6}$ alkoxy. In some embodiments, $R_1$ and $R_4$ are hydrogen, and $R_2$ and $R_3$ are independently selected from a group consisting of hydrogen, halogen, optionally substituted $C_{1-6}$ alkyl, and optionally substituted $C_{1-6}$ alkoxy.

In some embodiments, $R_1$, $R_2$, $R_3$, and $R_4$ are independently selected from a group consisting of hydrogen, Br, F, Cl, —$CH_3$, —$CF_3$, —$CH_2OH$, and —$OCH_3$. In some embodiments $R_1$ is selected from Br, F, Cl, —$CH_3$, —$CF_3$, —$CH_2OH$, and —$OCH_3$, and the other R groups are hydrogens. In some embodiments, $R_2$ is selected from hydrogen, Br, F, Cl, —$CH_3$, —$CF_3$, —$CH_2OH$, and —$OCH_3$, and the other R groups are hydrogens. In some embodiments, $R_3$ is selected from Br, F, Cl, —$CH_3$, —$CF_3$, —$CH_2OH$, and —$OCH_3$ and the other R groups are hydrogens. In some embodiments, $R_2$ is selected from hydrogen, F, —$CH_3$, and the other R groups are hydrogens.

In some embodiments, $R_5$ is selected from a group consisting of hydrogen, methyl, ethyl, benzyl, and halogen. In some embodiments, $R_5$ is hydrogen or methyl.

In some embodiments, $R_9$ is selected from the group consisting of optionally substituted $C_{1-6}$ alkoxy, optionally substituted $C_{1-6}$ alkoxy-$C_{1-6}$ alkyl (—$C_{1-6}$ alkyl-O—$C_{1-6}$ alkyl), optionally substituted $C_{2-6}$ alkenyloxy (—O—$C_{2-6}$ alkenyl), optionally substituted $C_{2-6}$ alkynyloxy (—O—$C_{2-6}$ alkynyl), optionally substituted $C_{3-6}$ cycloalkyloxy (—O—$C_{3-6}$ cycloalkyl).

In some embodiments, $R_9$ is selected from the group consisting of $C_{1-6}$ alkoxy, optionally substituted $C_{3-6}$ cycloalkyl-$C_{1-6}$ alkoxy (—O—$C_{1-6}$ alkyl-$C_{3-6}$ cycloalkyl), $C_{1-6}$ alkoxy-$C_{1-6}$alkyl (—$C_{1-6}$ alkyl-O—$C_{1-6}$ alkyl), $C_{2-6}$ alkenyloxy (—O—$C_{2-6}$ alkenyl), $C_{2-6}$ alkynyloxy (—O—$C_{2-6}$ alkynyl), and $C_{3-6}$ cycloalkyloxy (—O—$C_{3-6}$ cycloalkyl). In some embodiments, $R_9$ is selected form the group consisting of $C_{1-6}$ alkoxy, optionally substituted $C_{3-6}$ cycloalkyl-$C_{1-6}$ alkoxy, $C_{1-6}$ alkoxy-$C_{1-6}$ alkyl, $C_{2-6}$ alkenyloxy, $C_{2-6}$ alkynyloxy, and $C_{3-6}$ cycloalkyloxy.

In some embodiments, $R_9$ is selected from the group consisting of propoxy, cyclopropylmethoxy, cyclobutylmethoxy, allyloxy, methoxyethyl, ethoxyethyl, cyclopentyloxy, and prop-2-ynyloxy.

In some embodiments, $R_9$ is selected from the group consisting of cyclopropylmethoxy, allyloxy, and methoxyethyl.

In some embodiments, $R_9$ and $R_{10}$ together form optionally substituted $C_{1-6}$ alkoxy-$C_{1-6}$ alkylidene (—$C_{1-6}$ alkylidene-O—$C_{1-6}$ alkyl). In some embodiments, optionally substituted $C_{1-6}$ alkoxy-$C_{1-6}$ alkylidene is methoxyethylidene.

Any of the above disclosed embodiments may be combined with other embodiments making more specific emodiments, for example as disclosed in the accompanying claims.

Non-limiting examples of compounds according to formula (I) include:
1-(3-((1R,3r,5S)-3-(cyclopropylmethoxy)-8-azabicyclo[3.2.1]octan-8-yl)-2-methylpropyl)-1H-indazole;
1-((R)-3-((1R,3R,5S)-3-(cyclopropylmethoxy)-8-azabicyclo[3.2.1]octan-8-yl)-2-methylpropyl)-1H-indazole;
1-((R)-3-((1R,3R,5S)-3-(2-Methoxyethyl)-8-azabicyclo[3.2.1]octan-8-yl)-2-methylpropyl)-1H-indazole;
1-((R)-3-(3-(Cyclopropylmethoxy)-8-aza-bicyclo[3.2.1]octan-8-yl)-2-methylpropyl)-6-methyl-1H-indazole;
1-((R)-3-((1R,3R,5S)-3-(Allyloxy)-8-azabicyclo[3.2.1]octan-8-yl)-2-methylpropyl)-1H-indazole;
1-((R)-3-(3-(Cyclopropylmethoxy)-8-aza-bicyclo[3.2.1]octan-8-yl)-2-methylpropyl)-6-(trifluoromethyl)-1H-indazole;
1-((R)-3-(3-(Cyclopropylmethoxy)-8-aza-bicyclo[3.2.1]octan-8-yl)-2-methylpropyl)-6-fluoro-1H-indazole;
1-((R)-3-(3-(Allyloxy)-8-aza-bicyclo[3.2.1]octan-8-yl)-2-methylpropyl)-6-fluoro-1H-indazole;
1-((R)-3-(3-(2-Methoxyethyl)-8-aza-bicyclo[3.2.1]octan-8-yl)-2-methylpropyl)-6-fluoro-1H-indazole;
(1-((R)-3-((1R,3R,5S)-3-(cyclopropylmethoxy)-8-azabicyclo[3.2.1]octan-8-yl)-2-methylpropyl)-1H-indazol-6-yl)methanol;
1-((R)-3-(3-(cyclopropylmethoxy)-8-aza-bicyclo[3.2.1]octan-8-yl)-2-methylpropyl)-6-methoxy-1H-indazole;
1-((R)-3-((1R,3R,5S)-3-(2-methoxyethyl)-8-azabicyclo[3.2.1]octan-8-yl)-2-methylpropyl)-6-methyl-1H-indazole;
1-((R)-3-((1R,3R,5S)-3-(2-methoxyethyl)-8-azabicyclo[3.2.1]octan-8-yl)-2-methylpropyl)-6-methoxy-1H-indazole;
1-((R)-3-((1R,3R,5S)-3-(cyclopentyloxy)-8-azabicyclo[3.2.1]octan-8-yl)-2-methylpropyl)-1H-indazole;
1-((R)-3-(3-(cyclobutylmethoxy)-8-aza-bicyclo[3.2.1]octan-8-yl)-2-methylpropyl)-1H-indazole;
1-((R)-3-(3-(cyclopropylmethoxy)-8-aza-bicyclo[3.2.1]octan-8-yl)-2-methylpropyl)-3-methyl-1H-indazole;
1-((R)-3-(3-(cyclopropylmethoxy)-8-aza-bicyclo[3.2.1]octan-8-yl)-2-methylpropyl)-7-methyl-1H-indazole;
1-((R)-3-((1R,3R,5S)-3-(prop-2-ynyloxy)-8-azabicyclo[3.2.1]octan-8-yl)-2-methylpropyl)-1H-indazole;

1-((R)-3-((1R,3R,5S)-3-(propoxy)-8-azabicyclo[3.2.1]octan-8-yl)-2-methylpropyl)-1H-indazole;
1-((R)-3-((1R,3R,5S)-3-(2-methoxyethylidene)-8-azabicyclo[3.2.1]octan-8-yl)-2-methylpropyl)-1H-indazole;
1-((R)-3-(3-(cyclopropylmethoxy)-8-aza-bicyclo[3.2.1]octan-8-yl)-2-methylpropyl)-5-methyl-1H-indazole;
1-((R)-3-((1R,3R,5S)-3-(prop-2-ynyloxy)-8-azabicyclo[3.2.1]octan-8-yl)-2-methylpropyl)-6-methoxy-1H-indazole;
1-((R)-3-((1R,3R,5 S)-3-(2-ethoxyethyl)-8-azabicyclo[3.2.1]octan-8-yl)-2-methylpropyl)-1H-indazole; and
1-((R)-3-((1R,3R,5 S)-3-(2-ethoxyethyl)-8-azabicyclo[3.2.1]octan-8-yl)-2-methylpropyl)-6-methyl-1H-indazole.

Methods of Preparation

The compounds disclosed herein may be synthesized by methods described below, or by modification of these methods. Ways of modifying the methodology include, among others, temperature, solvent, reagents etc., and will be obvious to those skilled in the art. In general, during any of the processes for preparation of the compounds disclosed herein, it may be necessary and/or desirable to protect sensitive or reactive groups on any of the molecules concerned. This may be achieved by means of conventional protecting groups, such as those described in *Protective Groups in Organic Chemistry* (ed. J. F. W. McOmie, Plenum Press, 1973); and Greene & Wuts, *Protective Groups in Organic Synthesis*, John Wiley & Sons, 1991, which are both hereby incorporated herein by reference in their entirety. The protecting groups may be removed at a convenient subsequent stage using methods known from the art. Synthetic chemistry transformations useful in synthesizing applicable compounds are known in the art and include e.g. those described in R. Larock, *Comprehensive Organic Transformations*, VCH Publishers, 1989, or L. Paquette, ed., *Encyclopedia of Reagents for Organic Synthesis*, John Wiley and Sons, 1995, which are both hereby incorporated herein by reference in their entirety.

In some embodiments, the compounds disclosed herein may be synthesized according to Scheme I. Those of skill in the art will appreciate that the reactions depicted in Scheme I may be extended to substituted indazoles and other optionally substituted aromatic compounds. The variables, R is $R_1$, $R_2$, $R_3$, or $R_4$ as defined in Formula (I), and $R_9$ is the same as defined in Formula (I). Additionally other similar schemes are possible and are well understood by those skilled in the art based on the examples.

Scheme I

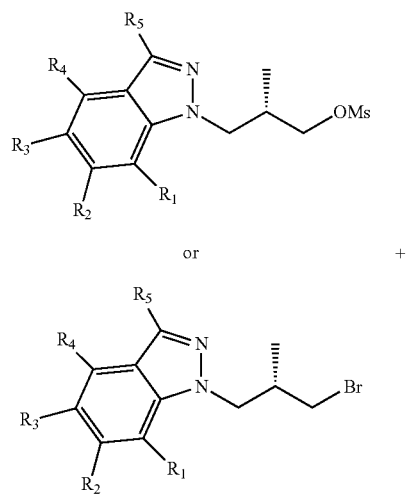

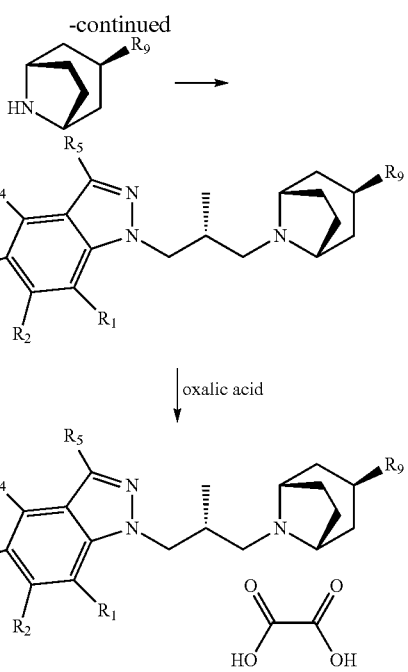

During any of the processes for preparation of the compounds disclosed herein, it may be necessary and/or desirable to protect sensitive or reactive groups on any of the molecules concerned. This may be achieved by means of conventional protecting groups, such as those described in Protective Groups in Organic Chemistry (McOmie ed., Plenum Press, 1973); and Greene & Wuts, Protective Groups in Organic Synthesis (John Wiley & Sons, 1991) The protecting groups may be removed at a convenient subsequent stage using methods known from the art.

Methods of Use

In general, compounds disclosed herein are active at cholinergic, specifically muscarinic receptors. In some embodiments, the compounds are selective for the M1 muscarinic receptor. In some embodiments, the compounds are muscarinic (M1) receptor selective agonists.

In some embodiments, the compounds disclosed herein exhibit low or no $M_3$ activity.

The compounds disclosed herein typically have therapeutic effects and can be used to treat or alleviate symptoms of disease or conditions associated with cholinergic receptors such as cognitive dysfunctions such as cognitive impairment, forgetfulness, confusion, memory loss, depression, attentional deficits, deficits in visual perception, and cognitive dysfunctions associated with mental disorders such as neuropsychiatric disorders, neurodegenerative disorders, dementia, age-related cognitive decline, and Down's syndrome; neuropsychiatric disorders such as sleep disorders, depression, psychosis, hallucinations, aggressiveness, paranoia, schizophrenia, attention deficit disorders, and Gilles de la Tourette's syndrome; eating disorders such as anorexia nervosa and bulimia; anxiety disorders such as obsessive compulsive disorders, panic disorders, phobic disorders, general anxiety disorders, and posttraumatic stress disorders; mood disorders, such as clinical depression, bipolar disorder, and major depressive disorder; neurodegenerative disorders and conditions such as alcoholism, Alzheimer's disease, amyotrophic lateral sclerosis, frontotemporal lobar degeneration, Huntington's disease, HIV-associated dementia, Lewy body dementia, multiple sclerosis, Parkinson's disease, Pick's disease, and progressive supranuclear palsy; and other diseases and disorders such as pain, such as neuropathic pain; increased intraocular pressure, glaucoma, ocular hypertension and other ophthamological conditions such as ocular surface indications and conditions such as dry eye, blepharitis and meibomian gland disease, corneal sensitivity that has been impaired due to surgery on the cornea or other surface of the eye, allergic conjunctivitis and atopic and vernal keratoconjunctivitis, treat ptyregia, ocular symptoms of graft versus host disease, ocular allergy, atopic keratoconjunctivitis, vernal keratoconjunctivitis, uveitis, anterior uveitis, Behcet's disease, Sjogren's syndrome, Stevens-Johnson syndrome, ocular cicatricial pemphigoid, chronic ocular surface inflammation caused by viral infection, herpes simplex keratitis, ocular rosacea, and pinguecula. In addition, the compounds disclosed herein may be used prevent corneal transplant rejection. Additionally the compounds disclosed herein may have neuroprotective effects and be used to treat age related macular degeneration, wet macular degeneration, dry macular degeneration, geographic atrophy, diabetic retinopathy, diabetic macular edema, tumors, retinal vein occlusion, optic neuropathy, ocular ischemic neuropathy, optic neuritis, retinitis pigmentosa and neuritis secondary to multiple sclerosis.

The diseases or conditions may result from dysfunction, decreased activity, modification, mutation, truncation, or loss of cholinergic receptors, especially muscarinic receptors, as well as from reduced levels of acetylcholine.

The compounds disclosed herein can also be used to treat diseases, e.g., cognitive dysfunctions such as cognitive impairment, forgetfulness, confusion, memory loss, depression, attentional deficits, deficits in visual perception, and cognitive dysfunctions associated with mental disorders such as neuropsychiatric disorders, neurodegenerative disorders, dementia, age-related cognitive decline, and Down's syndrome; neuropsychiatric disorders such as sleep disorders, depression, psychosis, hallucinations, aggressiveness, paranoia, schizophrenia, attention deficit disorders, and Gilles de la Tourette's syndrome; eating disorders such as anorexia nervosa and bulimia; anxiety disorders such as obsessive compulsive disorders, panic disorders, phobic disorders, general anxiety disorders, and posttraumatic stress disorders; mood disorders, such as clinical depression, bipolar disorder, and major depressive disorder; neurodegenerative disorders and conditions such as alcoholism, Alzheimer's disease, amyotrophic lateral sclerosis, frontotemporal lobar degeneration, Huntington's disease, HIV-associated dementia, Lewy body dementia, multiple sclerosis, Parkinson's disease, Pick's disease, and progressive supranuclear palsy; and other diseases and disorders such as pain, such as neuropathic pain; increased intraocular pressure, glaucoma, ocular hypertension and other ophthamological conditions such as ocular surface indications and conditions such as dry eye, blepharitis and meibomian gland disease, corneal sensitivity that has been impaired due to surgery on the cornea or other surface of the eye, allergic conjunctivitis and atopic and vernal keratoconjunctivitis, treat ptyregia, ocular symptoms of graft versus host disease, ocular allergy, atopic keratoconjunctivitis, vernal keratoconjunctivitis, uveitis, anterior uveitis, Behcet's disease, Sjogren's syndrome, Stevens-Johnson syndrome, ocular cicatricial pemphigoid, chronic ocular surface inflammation caused by viral infection, herpes simplex keratitis, ocular rosacea, and pinguecula. In addition, the compounds disclosed herein may be used prevent corneal transplant rejection. Additionally the compounds disclosed herein may have neuroprotective effects and be used to treat age related macular degeneration, wet macular degeneration, dry macular degeneration, geographic atrophy, diabetic retinopathy, diabetic macular edema, tumors, retinal vein occlusion, optic neuropathy, ocular ischemic neuropathy, optic neuritis, retinitis pigmentosa and neuritis secondary to multiple sclerosis.

The compounds disclosed herein may have the ability to increase cholinergic receptor activity or activate cholinergic receptors. Cholinergic receptor activity includes signaling activity or any other activity that is directly or indirectly related to cholinergic signaling or activation. The cholinergic receptors include muscarinic receptors. The muscarinic receptor can be, for example, in the central nervous system, peripheral nervous system, gastrointestinal system, heart, endocrine glands, or lungs. The muscarinic receptor can be a wild-type, truncated, mutated, or modified cholinergic receptor. Kits comprising the compounds disclosed herein for increasing cholinergic receptor activity or activating cholinergic receptors are also contemplated.

The system containing the cholinergic receptor may, for example, be a subject such as a mammal, non-human primate or a human. The system may also be an in vivo or in vitro experimental model, such as a cell culture model system that expresses a cholinergic receptor, a cell-free extract thereof that contains a cholinergic receptor, or a purified receptor. Non-limiting examples of such systems are tissue culture cells expressing the receptor, or extracts or lysates thereof. Cells that may be used in the present method include any cells capable of mediating signal transduction via cholinergic receptors, for example the $M_1$ muscarinic receptor, either via endogenous expression of this receptor (certain types of neuronal cells lines, for example, natively express the $M_1$ receptor), or such as following introduction of the an exogenous gene into the cell, for example, by transfection of cells with plasmids containing the receptor gene. Such cells are typically mammalian cells (or other eukaryotic cells, such as insect cells or *Xenopus* oocytes), because cells of lower life forms generally lack the appropriate signal transduction pathways for the present purpose. Examples of suitable cells include: the mouse fibroblast cell line NIH 3T3 (ATCC CRL 1658), which responds to transfected $M_1$ receptors by increased growth; RAT 1 cells (Pace et al., Proc. Natl. Acad. Sci. USA 88:7031-35 (1991)); and pituitary cells (Vallar et al., Nature 330:556-58 (1987)). Other useful mammalian cells for the present method include but are not limited to HEK 293 cells, CHO cells and COS cells.

The compounds disclosed herein also have the ability to reduce intraocular pressure and therefore can be used in the treatment of such diseases as glaucoma. Glaucoma is a disease in which an abnormality is observed in the circulation-control mechanism of the aqueous humor filling up the anterior chamber, i.e., the space formed between the cornea and the lens. This leads to an increase in the volume of the aqueous humor and an increase in intraocular pressure, consequently leading to visual field defects and even to loss of eyesight due to the compulsion and contraction of the papillae of the optic nerve. Some embodiments disclosed hererin are concerned with exploring muscarinic agonists to treat eye diseases. Examples of eye diseaseas are increased intraocular pressure, glaucoma, ocular hypertension, dry eye, blepharitis and meibomian gland disease, restore corneal sensitivity that has been impaired due to surgery on the cornea or other surface of the eye, allergic conjunctivitis and atopic and vernal keratoconjunctivitis, ptyregia, ocular symptoms of graft versus host disease, ocular allergy, atopic keratoconjunctivitis, vernal keratoconjunctivitis, uveitis, anterior uveitis, Behcet's disease, Sjogren's syndrome, Stevens-Johnson syndrome, ocular cicatricial pemphigoid, chronic ocular surface inflammation caused by viral infection, herpes simplex keratitis, ocular rosacea, and pinguecula. In addition, the compounds disclosed herein may be used prevent corneal transplant rejection. As stated above glaucoma generally refers to damage in the optic nerve. There are theories indicating that increased intraocular pressure (IOP) is a factor to consider in connection with damage of the optic nerve.

Accordingly, compounds disclosed herein have been found to reduce intraocular pressure. Compounds disclosed herein have also been found to have improved efficacy in vitro and in vivo, for example as tested by topical administration. The effect of some of the compounds disclosed herein can be seen in FIG. 1 where compounds disclosed herein have been compared to a compound as previously described as AC00263201 (Comparative compound 2). The compounds were topically administered to an ocular hypertensive monkey eye.

Figure 3:
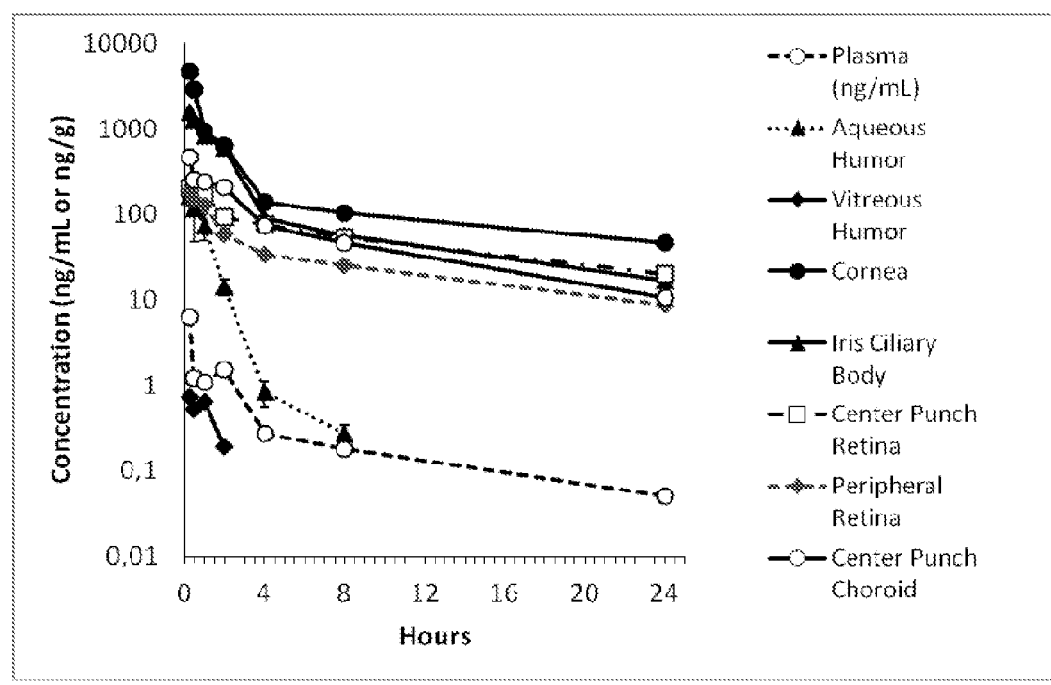
FIG. 3 shows concentration data of a compound disclosed herein in the compartments of the eye and in plasma.

Additionally compounds disclosed herein have been found to have good pharmacokinetic properties in particular in connection with eye diseases such as glaucoma and other ophthalmic conditions. Examples of pharmacokinetic (PK) properties are good corneal exposure, iris ciliary body exposure and retinal exposure for at least 24 h whereas the systemic exposure is low as can be seen in FIG. 3. The improved pharmacokinetics for example means that the half life of the compound in iris ciliary body may be improved.

Figure 2:
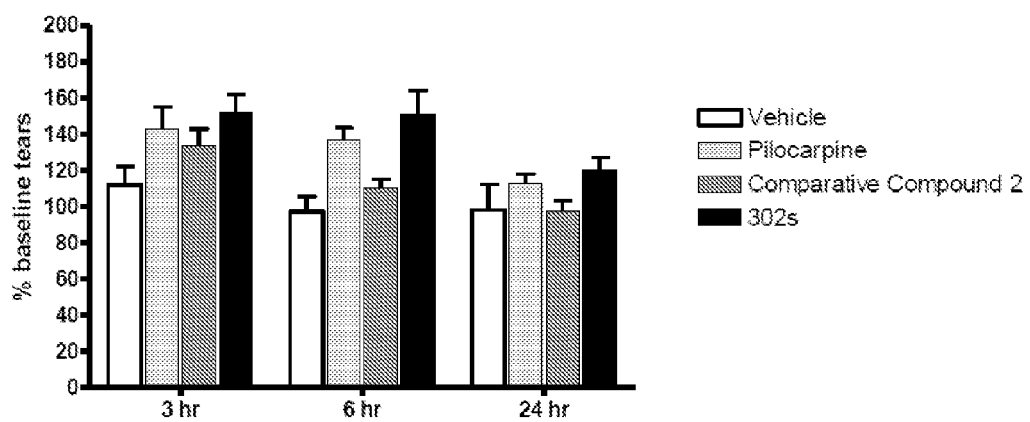
FIG. 2 illustrates the tear secreation effect over time of compounds disclosed herein compared to comparative compound 2 and pilocarpine.

The compounds disclosed herein have been found to increase tear secretion upon comparison with known pharmaceuticals used to treat eye diseases. An example of such pharmaceuticals is Pilocarpine. Pilocarpine is a non-selective muscarinic agonist and has in particular been used to treat dry eye and dry mouth symptoms by increasing tear and saliva secrection. FIG. 2 illustrates the results obtained from the increased tear secreation study between compounds disclosed herein, AC00263201 and Pilocarpine. Surprisingly compounds disclosed herein (i.e. M1 selective muscarinic agonists) have an action similar to Pilocarpine.

Some embodiments also pertain to the field of predictive medicine in which pharmacogenomics is used for prognostic (predictive) purposes. Pharmacogenomics deals with clinically significant hereditary variations in the response to drugs due to altered drug disposition and abnormal action in affected persons (see e.g., Eichelbaum, Clin Exp Pharmacol. Physiol., 23:983-985 (1996) and Linder, Clin. Chem. 43:254-66 (1997)). In general, two types of pharmacogenetic conditions can be differentiated: genetic conditions transmitted as a single factor altering the way drugs act on the body (altered drug action) or genetic conditions transmitted as single factors altering the way the body acts on drugs (altered drug metabolism). These pharmacogenetic conditions can occur as naturally-occurring polymorphisms.

One pharmacogenomics approach to identifying genes that predict drug response, known as "a genome-wide association", relies primarily on a high-resolution map of the human genome consisting of known gene-related markers (e.g., a "bi-allelic" gene marker map that consists of 60,000-100,000 polymorphic or variable sites on the human genome, each of which has two variants). Such a high-resolution genetic map can be compared to a map of the genome of each of a statistically significant number of patients taking part in a Phase II/III drug trial to identify markers associated with a particular observed drug response or side effect. Alternatively, such a high resolution map can be generated from a combination of some ten-million known single nucleotide polymorphisms (SNPs) in the human genome. As used herein, a "SNP" is a common alteration that occurs in a single nucleotide base in a stretch of DNA. For example, a SNP may occur once per every 1,000 bases of DNA. A SNP may be involved in a disease process although the vast majority may not be disease-associated. Given a genetic map based on the occurrence of such SNPs, individuals can be grouped into genetic categories depending on a particular pattern of SNPs in their individual genome. In such a manner, treatment regimens can be tailored to groups of genetically similar individuals, taking into account traits that may be common among such genetically similar individuals.

Alternatively, a method termed the "candidate gene approach" can be utilized to identify genes that predict drug response. According to this method, if a gene that encodes a drug's target is known (e.g., a protein or a receptor), all common variants of that gene can be identified in the population. It can be readily determined by standard techniques a particular version of the gene is associated with a particular drug response.

Alternatively, a method termed "gene expression profiling" can be utilized to identify genes that predict drug response. For example, the gene expression of an animal dosed with a drug (e.g., a compound or composition disclosed herein) can give an indication whether gene pathways related to toxicity have been turned on.

Information generated from more than one of the above pharmacogenomics approaches can be used to determine appropriate dosage and treatment regimens for prophylactic or therapeutic treatment of an individual. This knowledge, when applied to dosing or drug selection, can avoid adverse reactions or therapeutic failure and thus enhance therapeutic or prophylactic efficiency when treating a subject with a compound or composition disclosed herein, such as a modulator identified by one of the exemplary screening assays described herein. These approaches can also be used to identify novel candidate receptor or other genes suitable for further pharmacological characterization in vitro and in vivo.

Accordingly, other embodiments include methods for identifying a genetic polymorphism predisposing a subject to being responsive to a compound described herein. The method comprises administering to a subject an effective amount of a compound; identifying a responsive subject having an ameliorated disease or condition associated with a cholinergic receptor; and identifying a genetic polymorphism in the responsive subject, wherein the genetic polymorphism predisposes a subject to being responsive to the compound. Identifying a genetic polymorphism in the responsive subject can be performed by any means known in the art including the methods discussed above. In addition, a kit to be used for identifying a genetic polymorphism predisposing a subject to being responsive to a compound disclosed herein comprises the compound disclosed herein, and preferably reagents and instructions for performing a genetic polymorphism test.

In one embodiment, a subject can be tested for a known polymorphism that predisposes the subject to being responsive to the compound disclosed herein. The presence of the polymorphism indicates that the subject is suitable for treatment.

The pharmacological properties and the selectivity of the compounds disclosed herein for specific muscarinic receptor subtypes may be demonstrated by a number of different assay methods using, for example, recombinant receptor subtypes, preferably of the human receptors as available, e.g., conventional second messenger or binding assays. A particularly convenient functional assay system is the receptor selection and amplification assay disclosed in U.S. Pat. No. 5,707,798, which describes a method of screening for bioactive compounds by utilizing the ability of cells transfected with receptor DNA, e.g., coding for the different muscarinic subtypes, to amplify in the presence of a ligand of the receptor. Cell amplification is detected as increased levels of a marker also expressed by the cells.

One embodiment includes a method of increasing an activity of a cholinergic receptor comprising contacting the cholinergic receptor or a system containing the cholinergic receptor with an effective amount of at least one compound of Formula I, as defined supra.

Disorders suitable for treatment by compound disclosed herein include, but are not limited to, cognitive dysfunctions such as cognitive impairment, forgetfulness, confusion, memory loss, depression, attentional deficits, deficits in visual perception, and cognitive dysfunctions associated with mental disorders such as neuropsychiatric disorders, neurodegenerative disorders, dementia, age-related cognitive decline, and Down's syndrome; neuropsychiatric disorders such as sleep disorders, depression, psychosis, hallucinations, aggressiveness, paranoia, schizophrenia, attention deficit disorders, and Gilles de la Tourette's syndrome; eating disorders such as anorexia nervosa and bulimia; anxiety disorders such as obsessive compulsive disorders, panic disorders, phobic disorders, general anxiety disorders, and posttraumatic stress disorders; mood disorders, such as clinical depression, bipolar disorder, and major depressive disorder; neurodegenerative disorders and conditions such as alcoholism, Alzheimer's disease, amyotrophic lateral sclerosis, frontotemporal lobar degeneration, Huntington's disease, HIV-associated dementia, Lewy body dementia, multiple sclerosis, Parkinson's disease, Pick's disease, and progressive supranuclear palsy; and other diseases and disorders such as pain, such as neuropathic pain; increased intraocular pressure, glaucoma, ocular hypertension, dry eye, blepharitis and meibomian gland disease, restore corneal sensitivity that has been impaired due to surgery on the cornea or other surface of the eye, allergic conjunctivitis and atopic and vernal keratoconjunctivitis, ptyregia, ocular symptoms of graft versus host disease, ocular allergy, atopic keratoconjunctivitis, vernal keratoconjunctivitis, uveitis, anterior uveitis, Behcet's disease, Sjogren's syndrome, Stevens-Johnson syndrome, ocular cicatricial pemphigoid, chronic ocular surface inflammation caused by viral infection, herpes simplex keratitis, ocular rosacea, and pinguecula. In addition, the compounds disclosed herein may be used prevent corneal transplant rejection. Additionally the compounds disclosed herein may have neuroprotective effects and be used to treat age related macular degeneration, wet macular degeneration, dry macular degeneration, geographic atrophy, diabetic retinopathy, diabetic macular edema, tumors, retinal vein occlusion, optic neuropathy, ocular ischemic neuropathy, optic neuritis, retinitis pigmentosa and neuritis secondary to multiple sclerosis.

The Tic disorders also include a spectrum of disorders including Tourettes and obsessive compulsive disorder (OCD).

The affective disorder spectrum, including unipolar, bipolar are also anticipated to be suitable for treatment using compounds of Formula I.

Neuropathic pain results from damage to or dysfunction of the peripheral or central nervous system, rather than stimulation of pain receptors.

Pharmaceutical Compositions

In another aspect, the present disclosure relates to a pharmaceutical composition comprising a physiologically acceptable surface active agents, carriers, diluents, excipients, smoothing agents, suspension agents, film forming substances, and coating assistants, or a combination thereof; and a compound disclosed herein. Acceptable carriers or diluents for therapeutic use are well known in the pharmaceutical art, and are described, for example, in Remington's Pharmaceutical Sciences, 18th Ed., Mack Publishing Co., Easton, Pa. (1990), which is incorporated herein by reference in its entirety. Preservatives, stabilizers, dyes, sweeteners, fragrances, flavoring agents, and the like may be provided in the pharmaceutical composition. For example, sodium benzoate, ascorbic acid and esters of p-hydroxybenzoic acid may be added as preservatives. In addition, antioxidants and suspending agents may be used. In various embodiments, alcohols, esters, sulfated aliphatic alcohols, and the like may be used as surface active agents; sucrose, glucose, lactose, starch, crystallized cellulose, mannitol, light anhydrous silicate, magnesium aluminate, magnesium methasilicate aluminate, synthetic aluminum silicate, calcium carbonate, sodium acid carbonate, calcium hydrogen phosphate, calcium carboxymethyl cellulose, and the like may be used as excipients; magnesium stearate, talc, hardened oil and the like may be used as smoothing agents; coconut oil, olive oil, sesame oil, peanut oil, soya may be used as suspension agents or lubricants; cellulose acetate phthalate as a derivative of a carbohydrate such as cellulose or sugar, or methylacetate-methacrylate copolymer as a derivative of polyvinyl may be used as suspension agents; and plasticizers such as ester phthalates and the like may be used as suspension agents.

The term "pharmaceutical composition" refers to a mixture of a compound disclosed herein with other chemical components, such as diluents or carriers. The pharmaceutical composition facilitates administration of the compound to an organism. Multiple techniques of administering a compound exist in the art including, but not limited to, oral, injection, aerosol, parenteral, and topical administration. Pharmaceutical compositions can also be obtained by reacting compounds with inorganic or organic acids such as hydrochloric acid, hydrobromic acid, sulfuric acid, nitric acid, phosphoric acid, methanesulfonic acid, ethanesulfonic acid, p-toluenesulfonic acid, salicylic acid and the like.

The term "carrier" defines a chemical compound that facilitates the incorporation of a compound into cells or tissues. For example dimethyl sulfoxide (DMSO) is a commonly utilized carrier as it facilitates the uptake of many organic compounds into the cells or tissues of an organism.

The term "diluent" defines chemical compounds diluted in water that will dissolve the compound of interest as well as stabilize the biologically active form of the compound. Salts dissolved in buffered solutions are utilized as diluents in the art. One commonly used buffered solution is phosphate buffered saline because it mimics the salt conditions of human blood. Since buffer salts can control the pH of a solution at low concentrations, a buffered diluent rarely modifies the biological activity of a compound.

The term "physiologically acceptable" defines a carrier or diluent that does not abrogate the biological activity and properties of the compound.

The pharmaceutical compositions described herein can be administered to a human patient per se, or in pharmaceutical compositions where they are mixed with other active ingredients, as in combination therapy, or suitable carriers or excipient(s). Techniques for formulation and administration of the compounds of the instant application may be found in "Remington's Pharmaceutical Sciences," Mack Publishing Co., Easton, Pa., 18th edition, 1990.

Suitable routes of administration may, for example, include oral, rectal, transmucosal, topical, or intestinal administration; parenteral delivery, including intramuscular, subcutaneous, intravenous, intramedullary injections, as well as intrathecal, direct intraventricular, intraperitoneal, intranasal, or intraocular injections. The compounds can also be administered in sustained or controlled release dosage forms, including depot injections, osmotic pumps, pills, transdermal (including electrotransport) patches, and the like, for prolonged and/or timed, pulsed administration at a predetermined rate.

The pharmaceutical compositions may be manufactured in a manner that is itself known, e.g., by means of conventional mixing, dissolving, granulating, dragee-making, levigating, emulsifying, encapsulating, entrapping or tabletting processes.

Pharmaceutical compositions for use as described herein may be formulated in conventional manner using one or more physiologically acceptable carriers comprising excipients and auxiliaries which facilitate processing of the active compounds into preparations which can be used pharmaceutically. Proper formulation is dependent upon the route of administration chosen. Any of the well-known techniques, carriers, and excipients may be used as suitable and as understood in the art; e.g., in Remington's Pharmaceutical Sciences, above.

Injectables can be prepared in conventional forms, either as liquid solutions or suspensions, solid forms suitable for solution or suspension in liquid prior to injection, or as emulsions. Suitable excipients are, for example, water, saline, dextrose, mannitol, lactose, lecithin, albumin, sodium glutamate, cysteine hydrochloride, and the like. In addition, if desired, the injectable pharmaceutical compositions may contain minor amounts of nontoxic auxiliary substances, such as wetting agents, pH buffering agents, and the like. Physiologically compatible buffers include, but are not limited to, Hanks's solution, Ringer's solution, or physiological saline buffer. If desired, absorption enhancing preparations (for example, liposomes), may be utilized.

For transmucosal administration, penetrants appropriate to the barrier to be permeated may be used in the formulation.

Pharmaceutical formulations for parenteral administration, e.g., by bolus injection or continuous infusion, include aqueous solutions of the active compounds in water-soluble form. Additionally, suspensions of the active compounds may be prepared as appropriate oily injection suspensions. Suitable lipophilic solvents or vehicles include fatty oils such as sesame oil, or other organic oils such as soybean, grapefruit or almond oils, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents that increase the solubility of the compounds to allow for the preparation of highly concentrated solutions. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen-free water, before use.

For oral administration, the compounds can be formulated readily by combining the active compounds with pharmaceutically acceptable carriers well known in the art. Such carriers enable the compounds disclosed herein to be formulated as tablets, pills, dragees, capsules, liquids, gels, syrups, slurries, suspensions and the like, for oral ingestion by a patient to be treated. Pharmaceutical preparations for oral use can be obtained by combining the active compounds with solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate. Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols.

In addition, stabilizers may be added. All formulations for oral administration should be in dosages suitable for such administration.

For buccal administration, the compositions may take the form of tablets or lozenges formulated in conventional manner.

For administration by inhalation, the compounds for use as described herein are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of, e.g., gelatin for use in an inhaler or insufflator may be formulated containing a powder mix of the compound and a suitable powder base such as lactose or starch.

Further disclosed herein are various pharmaceutical compositions well known in the pharmaceutical art for uses that include intraocular, intranasal, and intraauricular delivery. Suitable penetrants for these uses are generally known in the art. Topical ophthalmic compositions may be formulated as a solution in water buffered at a pH of 5.0 to 8.0. Other ingredients that may be desirable to use in the ophthalmic preparations include preservatives (such as benzalkonium chloride, stabilized oxychloro complex, which is sold as Purite™, or stabilized chlorine dioxide), cosolvents (such as polysorbate 20, 60 and 80, Pluronic® F-68, F-84 and P-103, cyclodextrin, or Solutol) and viscosity-building agents (such as polyvinyl alcohol, polyvinyl pyrrolidone, methyl cellulose, hydroxypropyl methyl cellulose, hydroxyethyl cellulose, carboxymethyl cellulose, or hydroxypropyl cellulose). The compounds disclosed herein may also be used in an intraocular implant as described in U.S. Pat. No. 7,931,909 which is hereby incorporated by reference. Pharmaceutical compositions for intraocular delivery include aqueous ophthalmic solutions of the active compounds in water-soluble form, such as eyedrops, or in gellan gum (Shedden et al., *Clin. Ther.,* 23(3):440-50 (2001)) or hydrogels (Mayer et al., *Ophthalmologica,* 210(2): 101-3 (1996)); ophthalmic ointments; ophthalmic suspensions, such as microparticulates, drug-containing small polymeric particles that are suspended in a liquid carrier medium (Joshi, A., *J. Ocul. Pharmacol.,* 10(1):29-45 (1994)), lipid-soluble formulations (Alm et al., *Prog. Clin. Biol. Res.,* 312:447-58 (1989)), and microspheres (Mordenti, Toxicol. Sci., 52(1):101-6 (1999)); and ocular inserts. All of the above-mentioned references, are incorporated herein by reference in their entireties. Such suitable pharmaceutical formulations are most often and preferably formulated to be sterile, isotonic and buffered for stability and comfort. Pharmaceutical compositions for intranasal delviery may also include drops and sprays often prepared to simulate in many respects nasal secretions to ensure maintenance of normal ciliary action. As disclosed in Remington's Pharmaceutical Sciences, 18th Ed., Mack Publishing Co., Easton, Pa. (1990), which is incorporated herein by reference in its entirety, and well-known to those skilled in the art, suitable formulations are most often and preferably isotonic, slightly buffered to maintain a pH of 5.5 to 6.5, and most often and preferably include antimicrobial preservatives and appropriate drug stabilizers. Pharmaceutical formulations for intraauricular delivery include suspensions and ointments for topical application in the ear. Common solvents for such aural formulations include glycerin and water.

The compounds may also be formulated in rectal compositions such as suppositories or retention enemas, e.g., containing conventional suppository bases such as cocoa butter or other glycerides.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

For hydrophobic compounds, a suitable pharmaceutical carrier may be a cosolvent system comprising benzyl alcohol, a nonpolar surfactant, a water-miscible organic polymer, and an aqueous phase. A common cosolvent system used is the VPD co-solvent system, which is a solution of 3% w/v benzyl alcohol, 8% w/v of the nonpolar surfactant Polysorbate 80™, and 65% w/v polyethylene glycol 300, made up to volume in absolute ethanol. Naturally, the proportions of a co-solvent system may be varied considerably without destroying its solubility and toxicity characteristics. Furthermore, the identity of the co-solvent components may be varied: for example, other low-toxicity nonpolar surfactants may be used instead of POLYSORBATE 80™; the fraction size of polyethylene glycol may be varied; other biocompatible polymers may replace polyethylene glycol, e.g., polyvinyl pyrrolidone; and other sugars or polysaccharides may substitute for dextrose.

Alternatively, other delivery systems for hydrophobic pharmaceutical compounds may be employed. Liposomes and emulsions are well known examples of delivery vehicles or carriers for hydrophobic drugs. Certain organic solvents such as dimethylsulfoxide also may be employed, although usually at the cost of greater toxicity. Additionally, the compounds may be delivered using a sustained-release system, such as semipermeable matrices of solid hydrophobic polymers containing the therapeutic agent. Various sustained-release materials have been established and are well known by those skilled in the art. Sustained-release capsules may, depending on their chemical nature, release the compounds for a few weeks up to over 100 days. Depending on the chemical nature and the biological stability of the therapeutic reagent, additional strategies for protein stabilization may be employed.

Agents intended to be administered intracellularly may be administered using techniques well known to those of ordinary skill in the art. For example, such agents may be encapsulated into liposomes. All molecules present in an aqueous solution at the time of liposome formation are incorporated into the aqueous interior. The liposomal contents are both protected from the external micro-environment and, because liposomes fuse with cell membranes, are efficiently delivered into the cell cytoplasm. The liposome may be coated with a tissue-specific antibody. The liposomes will be targeted to and taken up selectively by the desired organ. Alternatively, small hydrophobic organic molecules may be directly administered intracellularly.

Additional therapeutic or diagnostic agents may be incorporated into the pharmaceutical compositions. Alternatively or additionally, pharmaceutical compositions may be combined with other compositions that contain other therapeutic or diagnostic agents.

Methods Of Administration

The compounds or pharmaceutical compositions may be administered to the patient by any suitable means. Non-limiting examples of methods of administration include, among others, (a) administration though oral pathways, which administration includes administration in capsule, tablet, granule, spray, syrup, or other such forms; (b) administration through non-oral pathways such as rectal, vaginal, intraurethral, intraocular, intranasal, or intraauricular, which administration includes administration as an aqueous suspension, an oily preparation or the like or as a drip, spray, suppository, salve, ointment or the like; (c) administration via injection, subcutaneously, intraperitoneally, intravenously, intramuscularly, intradermally, intraorbitally, intracapsularly, intraspinally, intrasternally, or the like, including infusion pump delivery; (d) administration locally such as by injection directly in the renal or cardiac area, e.g., by depot implantation; as well as (e) administration topically; as deemed appropriate by those of skill in the art for bringing the compound disclosed herein into contact with living tissue.

Pharmaceutical compositions suitable for administration include compositions where the active ingredients are contained in an amount effective to achieve its intended purpose. The therapeutically effective amount of the compounds disclosed herein required as a dose will depend on the route of administration, the type of animal, including human, being treated, and the physical characteristics of the specific animal under consideration. The dose can be tailored to achieve a desired effect, but will depend on such factors as weight, diet, concurrent medication and other factors which those skilled in the medical arts will recognize. More specifically, a therapeutically effective amount means an amount of compound effective to prevent, alleviate or ameliorate symptoms of disease or prolong the survival of the subject being treated. Determination of a therapeutically effective amount is well within the capability of those skilled in the art, especially in light of the detailed disclosure provided herein.

As will be readily apparent to one skilled in the art, the useful in vivo dosage to be administered and the particular mode of administration will vary depending upon the age, weight and mammalian species treated, the particular compounds employed, and the specific use for which these compounds are employed. The determination of effective dosage levels, that is the dosage levels necessary to achieve the desired result, can be accomplished by one skilled in the art using routine pharmacological methods. Typically, human clinical applications of products are commenced at lower dosage levels, with dosage level being increased until the desired effect is achieved. Alternatively, acceptable in vitro studies can be used to establish useful doses and routes of administration of the compositions identified by the present methods using established pharmacological methods.

In non-human animal studies, applications of potential products are commenced at higher dosage levels, with dosage being decreased until the desired effect is no longer achieved or adverse side effects disappear. The dosage may range broadly, depending upon the desired effects and the therapeutic indication. Typically, dosages may be between about 10 microgram/kg and 100 mg/kg body weight, preferably between about 100 microgram/kg and 10 mg/kg body weight. Alternatively dosages may be based and calculated upon the surface area of the patient, as understood by those of skill in the art.

The exact formulation, route of administration and dosage for the pharmaceutical compositions disclosed herein can be chosen by the individual physician in view of the patient's condition. (See e.g., Fingl et al. 1975, in "The Pharmacological Basis of Therapeutics", which is hereby incorporated herein by reference in its entirety, with particular reference to Ch. 1, p. 1). Typically, the dose range of the composition administered to the patient can be from about 0.5 to 1000 mg/kg of the patient's body weight. The dosage may be a single one or a series of two or more given in the course of one or more days, as is needed by the patient. In instances where human dosages for compounds have been established for at least some condition, those same dosages may be used, or dosages that are between about 0.1% and 500%, more preferably between about 25% and 250% of the established human dosage. Where no human dosage is established, as will be the case for newly-discovered pharmaceutical compounds, a suitable human dosage can be inferred from $ED_{50}$ or $ID_{50}$ values, or other appropriate values derived from in vitro or in vivo studies, as qualified by toxicity studies and efficacy studies in animals.

It should be noted that the attending physician would know how to and when to terminate, interrupt, or adjust administration due to toxicity or organ dysfunctions. Conversely, the attending physician would also know to adjust treatment to higher levels if the clinical response were not adequate (precluding toxicity). The magnitude of an administrated dose in the management of the disorder of interest will vary with the severity of the condition to be treated and to the route of administration. The severity of the condition may, for example, be evaluated, in part, by standard prognostic evaluation methods. Further, the dose and perhaps dose frequency, will also vary according to the age, body weight, and response of the individual patient. A program comparable to that discussed above may be used in veterinary medicine.

Although the exact dosage will be determined on a drug-by-drug basis, in most cases, some generalizations regarding the dosage can be made. The daily dosage regimen for an adult human patient may be, for example, an oral dose of between 0.1 mg and 2000 mg of each active ingredient, preferably between 1 mg and 500 mg, e.g. 5 to 200 mg. An ocular eye drop may range in concentration between 0.005 and 5 percent. In one embodiment, an eye drop may range between 0.01 and 1 percent, or between 0.01 and 0.3 percent in another embodiment. In other embodiments, an intravenous, subcutaneous, or intramuscular dose of each active ingredient of between 0.01 mg and 100 mg, preferably between 0.1 mg and 60 mg, e.g. 1 to 40 mg is used. In cases of administration of a pharmaceutically acceptable salt, dosages may be calculated as the free base. In some embodiments, the composition is administered 1 to 4 times per day. Alternatively the compositions disclosed herein may be administered by continuous intravenous infusion, preferably at a dose of each active ingredient up to 1000 mg per day. As will be understood by those of skill in the art, in certain situations it may be necessary to administer the compounds disclosed herein in amounts that exceed, or even far exceed, the above-stated, preferred dosage range or frequency in order to effectively and aggressively treat particularly aggressive diseases or infections. In some embodiments, the compounds will be administered for a period of continuous therapy, for example for a week or more, or for months or years.

Dosage amount and interval may be adjusted individually to provide plasma or tissue levels of the active moiety which are sufficient to maintain the modulating effects, or minimal effective concentration (MEC). The MEC will vary for each compound but can be estimated from in vitro data. Dosages necessary to achieve the MEC will depend on individual characteristics and route of administration. However, HPLC assays or bioassays can be used to determine plasma concentrations.

Dosage intervals can also be determined using MEC value. Compositions should be administered using a regimen which maintains plasma levels above the MEC for 10-90% of the time, preferably between 30-90% and most preferably between 50-90%.

In cases of local administration or selective uptake, the effective local concentration of the drug may not be related to plasma concentration.

The amount of composition administered may be dependent on the subject being treated, on the subject's weight, the severity of the affliction, the manner of administration and the judgment of the prescribing physician.

Compounds disclosed herein can be evaluated for efficacy and toxicity using known methods. For example, the toxicology of a particular compound, or of a subset of the compounds, sharing certain chemical moieties, may be established by determining in vitro toxicity towards a cell line, such as a mammalian, and preferably human, cell line. The results of such studies are often predictive of toxicity in animals, such as mammals, or more specifically, humans. Alternatively, the toxicity of particular compounds in an animal model, such as mice, rats, rabbits, or monkeys, may be determined using known methods. The efficacy of a particular compound may be established using several recognized methods, such as in vitro methods, animal models, or human clinical trials. Recognized in vitro models exist for nearly every class of condition, including but not limited to cancer, cardiovascular disease, and various immune dysfunction. Similarly, acceptable animal models may be used to establish efficacy of chemicals to treat such conditions. When selecting a model to determine efficacy, the skilled artisan can be guided by the state of the art to choose an appropriate model, dose, and route of administration, and regime. Of course, human clinical trials can also be used to determine the efficacy of a compound in humans.

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration. The pack or dispenser may also be accompanied with a notice associated with the container in form prescribed by a governmental agency regulating the manufacture, use, or sale of pharmaceuticals, which notice is reflective of approval by the agency of the form of the drug for human or veterinary administration. Such notice, for example, may be the labeling approved by the U.S. Food and Drug Administration for prescription drugs, or the approved product insert. Compositions comprising a compound disclosed herein formulated in a compatible pharmaceutical carrier may also be prepared, placed in an appropriate container, and labeled for treatment of an indicated condition.

Further details are provided in the following examples, which are not in any way intended to limit the scope of the accompanying claims.

EXAMPLES

Methods of Preparation

The compounds disclosed here can be synthesized by methods described below, or by modification of these methods. Ways of modifying the methodology include, for example, temperature, solvent, reagents etc, will be apparent to those skilled in the art.

General Analytical LC-MS Procedure

LC-MS Procedure 1:

Spectra were obtained using a HP1100 LC/MSD-instrument. A set-up with a binary pump, auto sampler, column oven, diode array detector, and electro spray ionisation interface was used. A reversed phase column (C18 Luna 3μ, 75×4.6 mm ID) with a guard column cartridge system was used. The mobile phase was acetonitrile/8 mM aqueous ammonium acetate. A 15-minute gradient program was used, starting at 70% acetonitrile over 12 minutes to 95% acetonitrile, over 1 minute to 70% acetonitrile, hold for 2 minutes. The flow rate was 0.6 mL/min.

LC-MS Procedure 2:

Spectra were obtained using a Waters LC/ZMD-instrument. A set-up with a 600 gradient pump, 2700 sample manager, 996 diode array detector, and electro spray ionisation interface was used. A reversed phase column (C18 X-Terra 5μ, 50×4.6 mm ID) with a guard column cartridge system was used. The mobile phase was acetonitrile/10 mM aqueous ammonium acetate. A 14-minute gradient program was used; starting at 30% acetonitrile, over 10 minutes to 95% acetonitrile, hold for 2 minutes, over 0.5 minutes to 30% acetonitrile, hold for 4.5 minutes. The flow rate was 1 mL/min.

General Preparative HPLC Procedure:

Preparative purification was performed on Waters Delta 4000 preparative system, Water 2487 dual absorbance detector, and Waters Fraction collector II. The column used was a Luna 15 μm C18, 250×21.2 mm. The following mobile phases were used: $H_2O$/acetonitrile ammonium acetate buffer (25 nM) or $H_2O$/acetonitrile TFA buffer (25 nM).

Cation-exchange column chromatography was performed with Varian BOND ELUT (mega BE-SCX, 1 g, 6 mL) columns. After applying the compound to the column, it was first washed with MeOH (2 column volumes) and thereafter the desired compound was eluted applying 2 column volumes of an NH4OH (25% $NH_3$ in $H_2O$)/MeOH mixture (1:9).

Starting Materials

Chemical names of starting materials and of the examples were generated by Beilstein CrossFire AutoNom Name or by ChemDraw Ultra 10.0.

3α-Cyclopropylmethoxy-8-azabicyclo[3.2.1]octane (4)

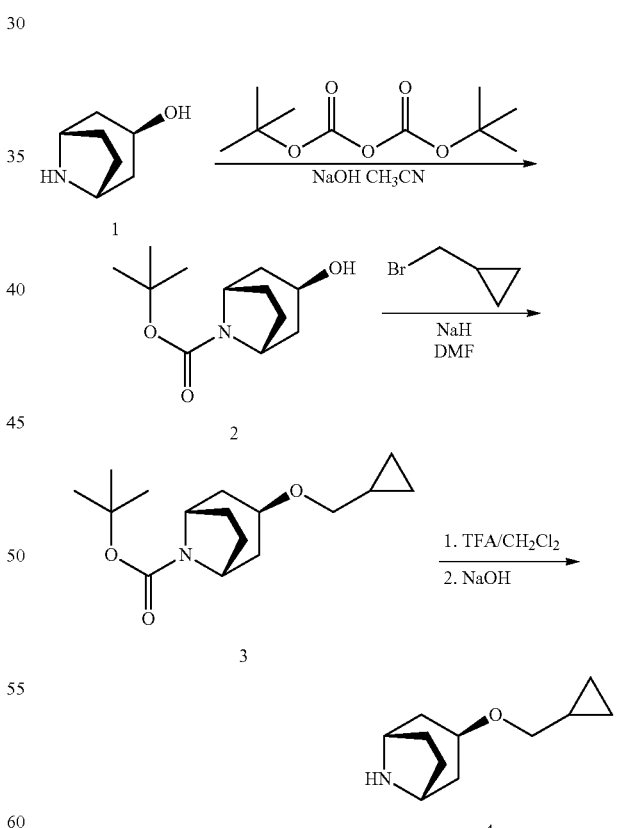

A reaction flask was charged with 8-azabicyclo[3.2.1]octan-3α-ol (1) (42.3 g, 0.33 mol) and di-tert-butyldicarbonate (80 g, 0.37 mol) in acetonitrile (500 mL) and 1 M NaOH (150 mL). The reaction was stirred at rt for 20 h, quenched with water and the product extracted into ethyl acetate. The combined organic phases were washed with 5% aqueous citric acid and brine, then dried over Na₂SO₄, filtered, and concentrated. The solid material was washed with n-heptane and dried to give the crude compound 2, 3α-hydroxy-8-azabicyclo[3.2.1]octane-8-carboxylic acid tert-butyl ester (76.2 g).

A reaction flask was charged with crude compound 2 (5.5 g) in dry DMF (25 mL) under argon. NaH (60% in oil, 0.968 g, 24.2 mmol) was added in portions and the mixture was stirred at 50° C. for 1 h. The mixture was cooled to rt and bromomethylcyclopropane (3.252 g, 24.2 mmol) was added followed by stirring at rt for 20 h under argon. The reaction mixture was quenched with water and the product extracted into ethyl acetate. The combined organic phases were dried over Na₂SO₄, filtered, and concentrated. The product was purified by flash column chromatography (SiO₂; n-heptane/ethyl acetate 2:1) to give the compound 3, 3α-cyclopropylmethoxy-8-azabicyclo[3.2.1]octane-8-carboxylic acid tert-butyl ester (3.354 g). $^1$H NMR (CDCl₃) δ 3.98-3.94 (m, 2H), 3.44-3.40 (m, 1H), 3.05 (d, 2H), 1.96-1.88 (m, 2H), 1.79-1.62 (m, 6H), 1.29 (s, 9H), 0.88-0.79 (m, 1H), 0.35-0.30 (m, 2H), 0.04-0.00 (m, 2H); $^{13}$C NMR (CDCl₃) δ 153.4, 78.9, 73.0, 72.5, 52.7, 34.9, 28.5, 28.1, 10.9, 2.8.

A reaction flask was charged with compound 3 (3.35 g, 11.9 mmol) in dichloromethane (5 mL). TFA (5 mL) was added and the reaction was stirred at rt for 4 h. The reaction mixture was quenched with 1 M NaOH and the product extracted into ethyl acetate. The combined organic phases were dried over Na₂SO₄, filtered, and concentrated to give the compound 4, 3α-Cyclopropylmethoxy-8-azabicyclo[3.2.1]octane (2.028 g, 94%). $^1$H NMR (CDCl₃) δ 3.38-3.37 (m, 1H), 3.33-3.28 (m, 2), 3.02 (d, J=6.5 Hz, 2H), 2.62 (br s, 2H), 1.97-1.86 (m, 2H), 1.72-1.44 (m, 4H), 0.89-0.76 (m, 1H), 0.36-0.23 (m, 2H), 0.04-0.00 (m, 2H); $^{13}$C NMR (CDCl₃) δ 72.6, 72.2, 53.5, 36.5, 29.0, 10.7, 2.6.

3α-(2-ethoxyethyl)-8-azabicyclo[3.2.1]octane (13)

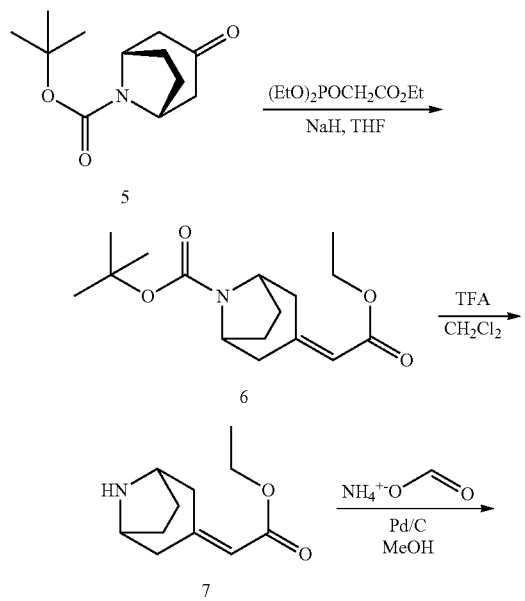

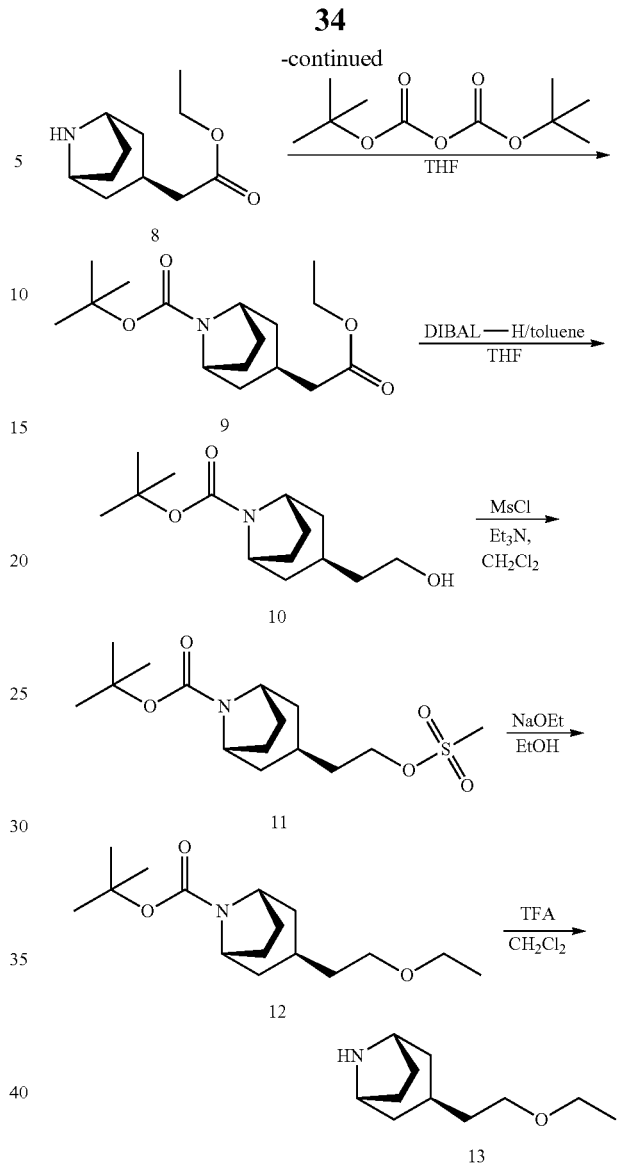

A reaction flask was charged with triethyl phosphonoacetate (7.458 g, 33.3 mmol) in dry THF (20 mL) under argon. NaH (60% in oil, 1.33 g, 33.3 mmol) was added in portions and the mixture was stirred at rt for 1 h. The clear solution was cooled to <10° C. with an icebath followed by dropwise addition of 3-oxo-8-azabicyclo[3.2.1]octane-8-carboxylic acid tert-butyl ester (5) (4.977 g, 22.2 mmol, commercially available from e.g. SigmaAldrich) dissolved in THF (5 mL) over 45 min. The temperature was slowly raised to rt. The reaction was stirred for 20 h. The reaction mixture was quenched with water and the product extracted into ethyl acetate. The combined organic phases were dried over Na₂SO₄, filtered, and concentrated. The product was purified by flash column chromatography (SiO₂; n-heptane/ethyl acetate 4:1) to give the compound 6,3-ethoxycarbonylmethylene-8-azabicyclo[3.2.1]octane-8-carboxylic acid tert-butyl ester (5.416 g, 82%). $^1$H NMR (CDCl₃) δ 5.76-5.74 (m, 1H), 4.28 (br s, 2H), 4.19-4.07 (m 2), 3.66-3.59 (m, 1H), 2.76-2.20 (m, 2H), 2.11-2.06 (m, 1H), 1.93-1.87 (m, 2H), 1.58-1.54 (m, 2H), 1.46 (m, 9H), 1.26 (m, 3H).

To 3-ethoxycarbonylmethylene-8-azabicyclo[3.2.1]octane-8-carboxylic acid tert-butyl ester (12.3 g, 41.8 mmol) in dichloromethane was added TFA (10 mL) and the reaction was stirred for 8 h. The solution was concentrated under reduced pressure, diluted with dichloromethane, and washed first with 2 M NaOH and followed by brine. The water phases were thereafter back-extracted with ethyl acetate and the combined organic phases were dried over $Na_2SO_4$, filtered, and concentrated under reduced pressure. The crude compound 7, (8-azabicyclo[3.2.1]oct-3-ylidene)acetic acid ethyl ester, was used without further purification (7.04 g, 37.9 mmol, 91%).

A 250 mL reaction flask was charged with compound 7 (3.7 g, 19 mmol), ammonium formiate (14 g, 190 mmol), and Pd/C (0.32 g, 8.6%) in 150 mL MeOH. When all of the ammonium formiate was dissolved the reaction flask was evacuted and flushed with nitrogen. The reaction was stirred on under an inert atmosphere ($N_2$) over night at rt. The reaction was filtered through celite, concentrated under reduced pressure, diluted with 2 M NaOH (ca pH 10), and extracted with ethyl acetate. The combined organic phases were washed with brine, dried over $Na_2SO_4$, filtered, and concentrated under reduced pressure. The crude product (8-azabicyclo[3.2.1]oct-3α-yl)acetic acid ethyl ester (8) (3.1 g, 16 mmol, 83%; 85:15 α:β) that was used without further purification. Major isomer: $^1$H NMR (CDCl$_3$) δ 4.08 (q, J=7.2 Hz, 2H), 3.45-3.41 (m, 2H), 2.40 (d, J=8.0 Hz, 2H), 2.25-2.18 (m, 1H), 2.06-1.96 (m, 2H), 1.82-1.55 (m, 5H), 1.31-1.23 (m, 2H), 1.21 (t, J=7.2 Hz, 3H); $^{13}$C NMR (CDCl$_3$) δ 173.3, 60.4, 53.6, 42.6, 36.7, 30.4, 25.4, 14.4.

A solution of di-tert-butyldicarbonate (4.3 g, 20 mmol) in THF (10 mL) was added to a cooled solution of compound 8 (2.8 g, 14 mmol) in THF (40 mL). The reaction was stirred at rt for 14 h and concentrated under reduced pressure. The semi-solid residue was dissolved with ethyl acetate, washed with brine, dried over $Na_2SO_4$, filtered, and concentrated under reduced pressure. The oily residue was purified by flash column chromatography ($SiO_2$; n-heptane/ethyl acetate 70:30) to yield 3α-ethoxycarbonylmethyl-8-aza-bicyclo[3.2.1]octane-8-carboxylic acid tert-butyl ester (9) as an oil (3.8 g, 73%). Major isomer: $^1$H NMR (CDCl$_3$) δ 4.16 (vbr s, 2H), 4.11 (q, J=6.8 Hz, 2H), 2.43 (d, J=7.6 Hz, 2H), 2.24-2.12 (m, 3H), 2.00-1.92 (m, 2H), 1.70-1.61 (m, 2H), 1.44 (s, 9H), 1.23 (t, J=6.8 Hz, 3H).

Under an inert atmosphere a solution of DIBAL-H (20 mL, 1.5 M) in toluene was slowly added to a −72° C. solution of compound 9 (3.7 g, 12 mmol) in dry THF (20 mL). The reaction was stirred at −72° C. for 1 h and then the temperature was slowly raised. At −10° C. the reaction was quenched with i-PrOH, stirred for 15 min and then water was added. The resulting gel-like substance was filtered through celite with dichloromethane and the eluent was washed with brine, dried over $Na_2SO_4$, filtered, and concentrated under reduced pressure. The oily residue was purified by flash column chromatography ($SiO_2$; n-heptane/ethyl acetate 40:60) to yield 3α-(2-hydroxyethyl)-8-azabicyclo[3.2.1]octane-8-carboxylic acid tert-butyl ester (10) as an oil (2.4 g, 74%). Major isomer: $^1$H NMR (CDCl$_3$) δ 4.15 (vbr s, 2H), 3.64 (t, J=4.4 Hz, 2H), 2.24-2.15 (m, 2H), 1.99-1.92 (m, 2H), 1.77-1.61 (m, 5H), 1.44 (s, 9H), 1.28-1.17 (m, 2H); $^{13}$C NMR (CDCl$_3$) δ 154.2, 79.2, 61.7, 52.4, 40.5, 35.9, 29.9, 28.7, 25.2.

Compound 10 (2.3 g, 9.0 mmol) was added to a solution of Et3N (5 mL) in dichloromethane (20 mL) and then cooled on an ice bath. Thereafter, MsCl (1.0 mL, 13.5 mmol) was slowly added. The reaction was stirred at 0° C. for 5 min and then at rt for 2 h. The reaction was quenched with brine, the phases were separated, and the water phase was extracted with dichloromethane. The combined organic phases were washed with brine, dried over $Na_2SO_4$, filtered, and concentrated under reduced pressure. The oily residue was purified by flash column chromatography ($SiO_2$; n-heptane/ethyl acetate 50:50) to yield 3α-(2-methanesulfonyloxyethyl)-8-azabicyclo[3.2.1]octane-8-carboxylic acid tert-butyl ester (11) (2.9 g, 95%) as an oil, which solidified upon standing.

A solution of compound 11 (2.8 g, 8.4 mmol) in dry EtOH (15 mL) was added to a solution of NaOEt (17 mL, 2.8 M in EtOH). The reaction was stirred under an inert atmosphere at 40° C. for 64 h, concentrated under reduced pressure, poured onto brine and extracted with ethyl acetate. The organic phase were dried over $Na_2SO_4$, filtered, and concentrated under reduced pressure. The oily residue was purified by flash column chromatography ($SiO_2$; n-heptane/ethyl acetate 70:30) to yield 3α-(2-ethoxyethyl)-8-azabicyclo[3.2.1]octane-8-carboxylic acid tert-butyl ester (12) as an oil (2.9 g, 7.1 mmol, 83%). Major isomer: $^1$H NMR (CDCl$_3$) δ 4.14 (vbr s, 2H), 3.44 (t, J=7.2 Hz, 2H), 3.39 (q, J=6.6 Hz, 2H), 2.13 (m, 2H), 1.98-1.90 (m, 2H), 1.74-1.62 (m, 5H), 1.44 (s, 9H), 1.25-1.18 (m, 2H), 1.17 (t, J, =6.6 Hz); $^{13}$C NMR (CDCl$_3$) δ 154.1, 79.1, 69.6, 66.4, 52.5, 37.6, 35.9, 29.8, 28.7, 25.7, 15.4.

To compound 12 (2.0 g, 7.1 mmol) in dichloromethane (5 mL) was added TFA (5 mL) and the reaction was stirred for 4 h. The solution was concentrated under reduced pressure, diluted with ethyl acetate, and the solution was washed with aq NaOH (2M) and brine. The organic solution was dried over $Na_2SO_4$, filtered, and concentrated under reduced pressure. The crude 3α-(2-ethoxyethyl)-8-azabicyclo[3.2.1]octane (13) (1.2 g, 6.3 mmol, 88%) was used without further purification. Major isomer: $^1$H NMR (CDCl$_3$) δ 3.47-3.34 (m, 6H), 2.04-1.94 (m, 2H), 1.82-1.64 (m, 8H), 1.30-1.23 (m, 2H), 1.16 (t, J=7.2 Hz, 3H); $^{13}$C NMR (CDCl$_3$) δ 69.8, 66.3, 53.7, 37.9, 37.3, 30.6, 25.3, 15.4

3α-(2-Methoxyethyl)-8-azabicyclo[3.2.1]octane (15)

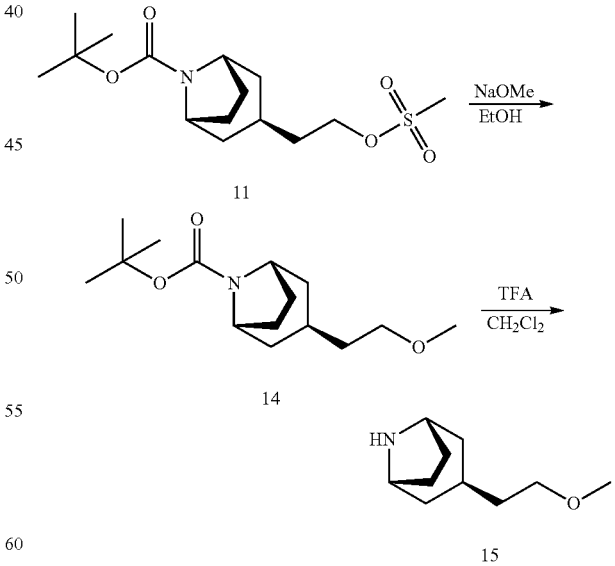

To a solution of compound 11 (1.0 g, 3.0 mmol) in dry EtOH (7 mL) was added a solution of NaOMe (17 mL, 2.8 M in EtOH). The reaction was stirred under an inert atmosphere (N2) at 40° C. for 6 days, concentrated, poured into brine, and extracted with ethyl acetate. The combined organic phases were dried over Na$_2$SO$_4$, filtered, and concentrated. The oily residue was purified by flash column chromatography (SiO$_2$; n-heptane/ethyl acetate 7:3) to yield 3α-(2-methoxyethyl)-8-azabicyclo[3.2.1]octane-8-carboxylic acid tert-butyl ester (14) (0.7 g, 86%) as an oil. Major isomer: $^1$H NMR (CDCl$_3$) δ 4.14 (vbr s, 2H), 3.35 (t, J=6.4 Hz, 2H), 3.28 (s, 3H), 2.16 (brs, 2H), 1.98-1.87 (m, 2H), 1.74-1.62 (m, 5H), 1.44 (s, 9H), 1.25-1.15 (m, 2H); $^{13}$C NMR (CDCl$_3$) δ 154.1, 79.1, 71.8, 58.8, 52.6 (br), 37.4, 35.8 (br), 29.8 (br), 28.7, 25.7.

To compound 14 (0.7 g, 2.6 mmol) in dichloromethane (2 mL) was added TFA (1 mL) and the reaction was stirred for 3 h. The solution was concentrated under reduced pressure, diluted with diethyl ether, and the solution was washed with aq NaOH (2M) and brine. The organic solution was dried over Na$_2$SO$_4$, filtered, and concentrated under reduced pressure. Compound 15, 3α-(2-Methoxyethyl)-8-azabicyclo[3.2.1]octane (0.400 g, 91%), was used without further purification.

3α-Prop-2-ynyloxy-8-azabicyclo[3.2.1]octane (16)

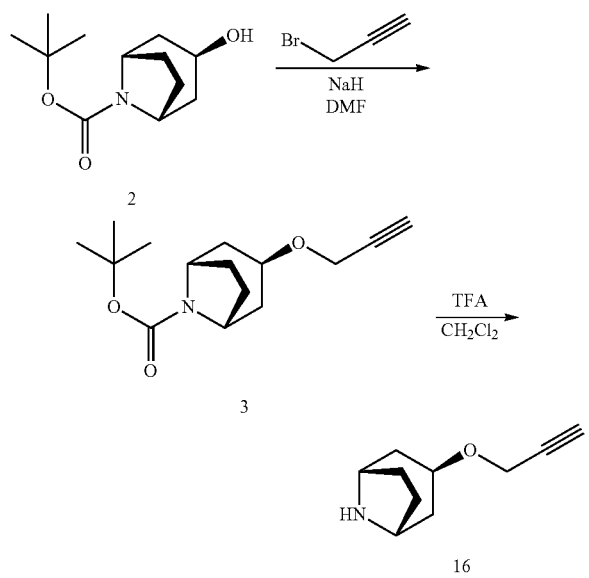

A reaction flask was charged with crude compound 2 (2.852 g, 12.5 mmol) in dry DMF (15 mL) under argon. NaH (60% in oil, 0.550 g, 12.5 mmol) was added in portions and the mixture was stirred at 50° C. for 1 h. The mixture was cooled to rt and 3-bromopropyne (1.869 g, 80% in toluene, 12.5 mmol) was added followed by stirring at rt for 20 h under argon. The reaction mixture was quenched with water and the product extracted into ethyl acetate. The combined organic phases were dried over Na$_2$SO$_4$, filtered, and concentrated. The product was purified by flash column chromatography (SiO$_2$; n-heptane/ethyl acetate 2:1) to give 3α-prop-2-ynyloxy-8-azabicyclo[3.2.1]octane-8-carboxylic acid tert-butyl ester (3) (0.977 g, 29%).

A reaction flask was charged with compound 3 (0.100 g, 0.38 mmol) in dichloromethane (0.2 mL). TFA (0.1 mL) was added and the reaction was stirred at rt for 1½ h. The reaction mixture was concentrated to give the TFA salt of 3α-Prop-2-ynyloxy-8-azabicyclo[3.2.1]octane (16).

(1R,3r,5S)-3-(allyloxy)-8-azabicyclo[3.2.1]octane (17)

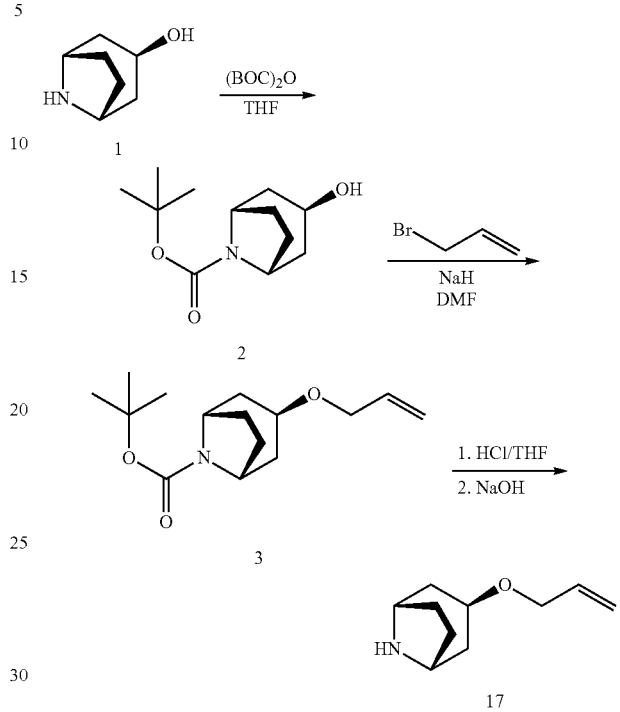

Compound 1 (10 g, 0.079 mol) was taken up in tetrahydrofuran (200 mL) followed by the addition of BOC-anhydride (17.2 g, 0.079 mol) in one portion. The solution was stirred at room temperature for overnight and then concentrated in vacuo to a brown solid. The crude product was taken up in 95% dichloromethane/5% methanol and added to a pad of silica gel (elution with 95% dichloromethane/5% methanol). Fractions containing compound 2 were combined and concentrated to a white solid. Yield: 16.6 g (93%); MS [M+H]+ 171.8 (M-56), 127.8 (M-100); $^1$HNMR (DMSO-d6) δ4.59 (s, 1H), 3.98-3.91 (m, 3H), 2.11 (bs, 2H), 1.85 (m, 4H), 1.64 (m, 2H), 1.47 (s, 9H) ppm.

The BOC-protected amine 2 (3 g, 0.013 mol) was taken up in 30 mL of anhydrous N.Ndimethylformamide and treated with 60% sodium hydride (NaH) (1 g, 0.025 mol) in small portions. The mixture was stirred at room temperature for 30 minutes followed by the dropwise addition of allyl bromide (3.2 g, 0.026 mol). The reaction mixture was stirred at room temperature for overnight and then diluted with equal portions of water and diethyl ether (100 mL each). The organic phase was separated, dried (MgSO4), filtered and the filtrate was concentrated to a viscous liquid. The crude product was taken up in 80% hexane/20% ethyl acetate and passed through a pad of silica gel eluting with the hexane/ethyl acetate mobile phase. Fractions containing the product were combined and concentrated to give compound 3 as a colorless liquid. Yield: 2.98 g (86%); MS [M+H]$^+$ 211.9 (M-56).

Compound 3 (2.98 g; 0.011 mol) was taken up in 20 mL of tetrahydrofuran followed by the addition of concentrated HCl (3 mL). The solution was stirred at room temperature for 2 days at which time the solvent was concentrated to dryness. The resulting viscous syrup was washed several times with tetrahydrofuran and concentrated. The solid was trituated with diethyl ether and collected by filtration to give compound 17 (1.76 g) as the HCl salt. The salt (1.1 g) was suspended in 25 mL of dichloromethane and treated with 12 mL of 1M sodium hydroxide (NaOH). The mixture was stirred at room temperature for overnight and then the organic phase was separated and dried over sodium sulfate. The drying agent was removed by filtration and the filtrate was concentrated to yield compound 17 as a colorless liquid. Yield 0.86 g; MS [M+H]⁺ 167.8

(1R,3r,5S)-3-(cyclopentyloxy)-8-azabicyclo[3.2.1]octane (18)

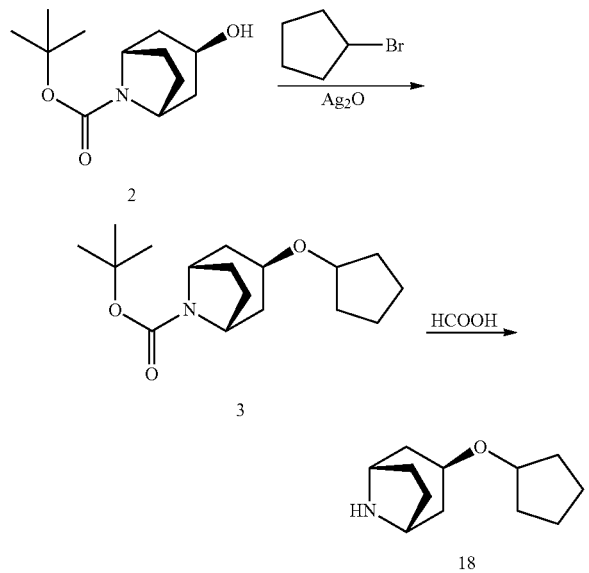

A reaction flask was charged with compound 2 (1 eq) and bromocyclopentane (20 mL). The mixture was heated to 70° C. and turned clear. To the solution was added powder Ag$_2$O (2 eq) and the mixture was continued to stir overnight. The volatile was removed under reduced pressure and the residue was purified by flash column chromatography to afford the product compound 3 (0.6 g).

The mixture of HCOOH (3 mL) and compound 3 (0.6 g, 1.9 mmol) was stirred for 36 h at room temperature. After the volatile was removed, the residue was adjusted pH to 10-11 by aqueous NaOH solution and stirred for 5-10 min. The organic solution was dried and concentrated to give the product compound 18 (0.3 g) as yellow oil.

(1R,3r,5S)-3-(cyclobutylmethoxy)-8-azabicyclo[3.2.1]octane (22)

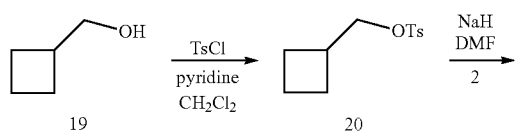

To a stirring solution of cyclobutanemethanol 19 (1.0 g, 11.61 mmol) and pyridine (2.5 mL, 31.03 mmol) in CH$_2$Cl$_2$ (25.0 mL) at 0° C. was added to sylchloride (1.8 g, 9.44 mmol). The mixture was warmed to room temperature and stirred for 20 h. The mixture was diluted with EtOAc and washed with water. Extracted with EtOAc (2×100 mL), washed with 1% HCl, water and brine, dried (MgSO$_4$) and concentrated. The colorless oil was dried under high vacuum to afford compound 20 (2.20 g).

To a stirring solution of 3-hydroxy-8-azabicyclo[3.2.1]octane-8-carboxylic acid tert-butyl ester (2) (1.82 g, 8.0 mmol) in DMF (50.0 mL) was added NaH (0.384 g, 9.6 mmol) portion wise. Stirred at room temperature for 30 min., then added compound 20 (1.97 g, 8.19 mmol). The mixture stirred at 55° C. for 20 h. The mixture was concentrated, then carefully diluted with water and extracted with EtOAc (3×120 mL). The org. extracts were washed with water, dried (MgSO$_4$) and concentrated. Purified via column chromatography, eluting with 10-20% EtOAc/hexanes to afford compound 21 (1.35 g) as a colorless oil.

To a stirring solution of compound 21 (1.35 g, 4.56 mmol) in CH$_2$Cl$_2$ (35.0 mL) was added TFA (3.89 mL, 52.36 mmol). Let stir at rt (room temperature) for 4 h. A 1N NaOH (52.0 mL) solution was added and the mixture stirred at room temperature for 1 h. Extracted with EtOAc (3×100 mL), dried (MgSO$_4$) and concentrated to afford compound 22 (0.70 g) as a dark yellow oil. No further purification was performed.

(R)-3-((1R,3R,5S)-3-(cyclopropylmethoxy)-8-azabicyclo[3.2.1]octan-8-yl)-2-methylpropan-1-ol (23)

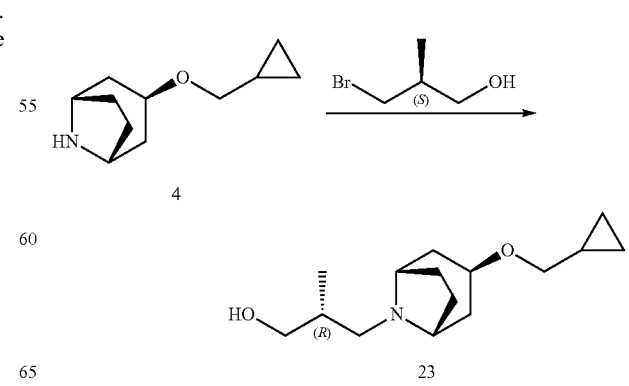

A solution of compound 4, (S)-3-bromo-2-methylpropan-1-ol and Cs$_2$CO$_3$ were stirred in DMF at 50° C. 7 h. The suspension was cooled to room temperature, water was added and the mixture extracted with diethyl ether. The combined organic layers were washed with water, brine, dried over Na$_2$SO$_4$. After flash column chromatography (petroleum ether/EtOAc ("PE/EA")=100:1). (R)-3-((1R,3R,5S)-3-(cyclopropylmethoxy)-8-azabicyclo[3.2.1]octan-8-yl)-2-methylpropan-1-ol (23) (0.063 g) was obtained. Yield: 37.7%; m/z=254[M+H]$^+$ (1R,3r,5S)-3-propoxy-8-azabicyclo[3.2.1]octane (24)

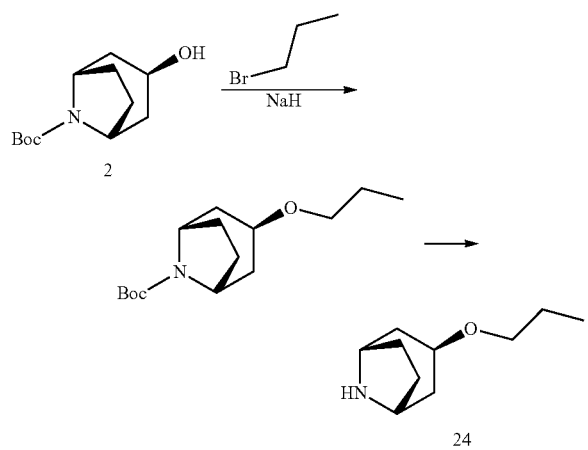

A mixture of compound 2 (3.2 g. 14 mmol) and NaH (60% in oil, 2.12 g, 53 mmol) in DMF was stirred under N$_2$ for 1 hour and then 1-bromopropanee (1.72 g, 14 mmol) was added. This mixture was stirred at room temperature overnight. The solvents were removed. The residue was chromatographed (petroleum ether/ethyl acetate=20/1) on gel to give the N-protected intermediate compound (1.254 g, yield: 32.9%); LC-MS (ESI): 270[M+H]$^+$ A mixture of the N-protected intermediate compound (1254 mg, 4.66 mmol) and 50% TFA (trifluoroacetic acid) in DCM (dichloromethane) (30 ml) was stirred at rt for 3 h. The reaction mixture was concentrated under a reduce pressure and dissolved in DCM 50 ml, washed with saturated Na$_2$CO$_3$ 20 ml, the organic layer was dried over anhydrous Na$_2$SO$_4$, filtered, and concentrated to afford (1R,3r,5S)-3-propoxy-8-azabicyclo[3.2.1]octane (24) (780 mg, yield: 99%); LC-MS (ESI): 170[M+H]$^+$ (1R,5S,Z)-3-(2-methoxyethylidene)-8-azabicyclo[3.2.1]octane (25)

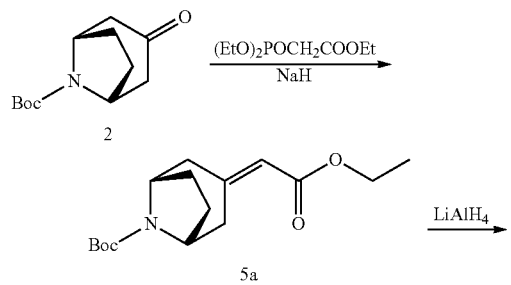

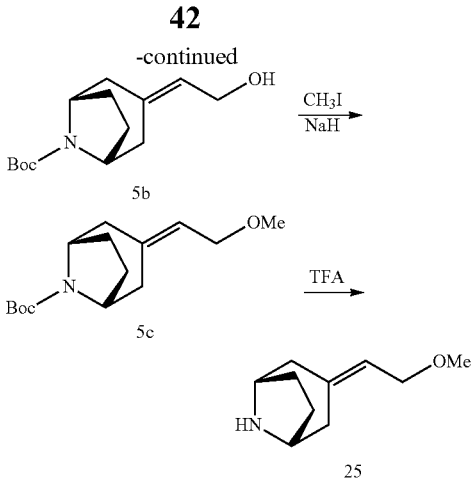

To a slurry of 70% NaH (1.3 g, 38 mmol) in THF (tetrahydrofuran) (50 mL) at 0° C. under N$_2$ atmosphere was added dropwise a solution of triethyl phosphonoacetate (8.5 g, 38 mmol). After the addition was completed, the mixture was continued to stir at room temperature for 1 hour. Then the mixture was re-cooled to 0° C. and a solution of N-Boc-nortropinone (5) (8.5 g, 38 mmol) in THF was added in dropwise. The resulted mixture was stirred at room temperature overnight. Water was added in to quench the reaction and the mixture was extracted with ethyl acetate (100 mL×3). The combined organic phase was washed with brine and dried over anhydrous sodium sulfate. After removing the solvent, the residue was purified by silica-gel column to obtain compound 5a (3.0 g).

To a solution of compound 5a (3.0 g, 10 mmol) in THF was added LiAlH$_4$ (1.0 g, 26 mmol) carefully. Then the mixture was heated to reflux under nitrogen atmosphere for 1 h. After cooling down to room temperature, 50 mL of ethyl acetate was added in carefully. The jam-like mixture was filtrated and washed with ethyl acetate. The filtration was washed with brine, dried over anhydrous sodium sulfate and concentrated. The residue was purified by column chromatography to give compound 5b as colorless oil (1.2 g).

To a solution of compound 5b (1.0 g, 3.95 mmol) in DMF (20 mL) was added NaH (1.0 g, 29.2 mmol) at 0° C. The mixture was stirred at room temperature for 1 hour. Then the mixture was cooled to 0° C. again and methyl iodide (4.0 g, 28.2 mmol) was added in. The resulting mixture was stirred at room temperature overnight. The mixture was partitioned between ethyl acetate and water. Then organic phase was separated and aqueous phase was extracted with ethyl acetate twice. The combined organic phase was washed with brine, dried over anhydrous sodium sulfate and concentrated. The residue was purified by column chromatography to give compound 5c as colorless oil (0.6 g).

TFA (2 mL) was added slowly to a solution of 5c (0.6 g, 2.24 mmol) in DCM (5 mL). After the mixture was stirred for 3 h at rt, the solvent was removed and then the residue was dissolved in 20 ml DCM and pH was adjusted to 10-11 by aqueous NaOH solution and stirred for 5-10 min. The organic solution was separated and dried and concentrated to give 350 mg of compound 25. The product was used without further purification.

(R,S)-1-(3-Chloro-2-methylpropyl)-1H-indazole (102)

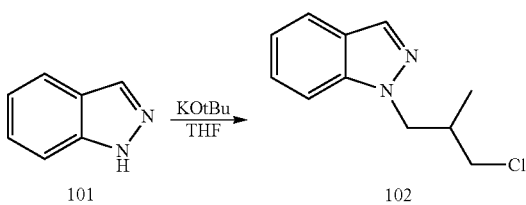

A reaction flask was charged with indazole 101 (3.54 g, 30.0 mmol) in dry THF (100 mL). KOtBu (3.54 g, 31.5 mmol) was added and the mixture was stirred at rt for 1 h. Then (R,S)-1-bromo-3-chloro-2-methylpropane (3.68 mL, 31.5 mmol) was added and the mixture stirred at 50° C. overnight. The reaction mixture was quenched with water and extracted with ethyl acetate. The combined organic layers were dried over $Na_2SO_4$, filtered, and evaporated to dryness. The crude product was purified by flash column chromatography ($SiO_2$; n-heptane/ethyl acetate 2:1) to give the title compound 102 (4.66 g).

(S)-3-(1H-indazol-1-yl)-2-methylpropyl methanesulfonate (104)

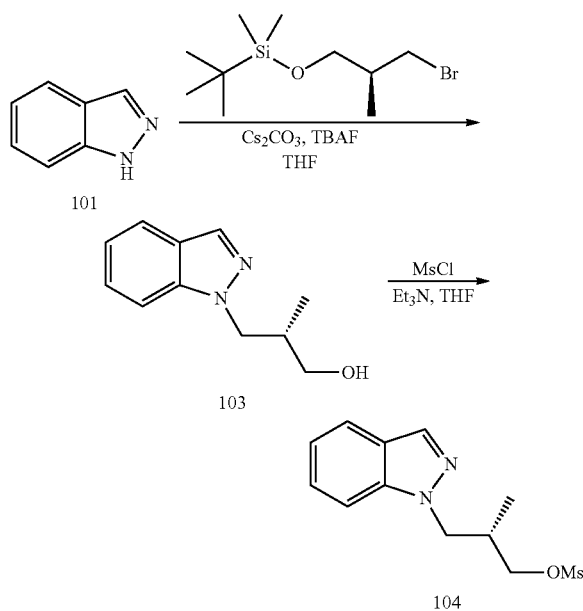

A solution of indazole 101 (2.41 g, 20.4 mmol), ((S)-3-bromo-2-methylpropoxy)(tert-butyl)dimethylsilane (4.81 g, 19.0 mmol), and $Cs_2CO_3$ (10.03 g, 30.9 mmol) were stirred in DMF (40 mL) at 70° C. overnight. The suspension was cooled to rt, water was added and the mixture extracted with diethyl ether. The combined organic layers were washed with water, brine, dried over $Na_2SO_4$ and adsorbed onto celite. After flash column chromatography ($SiO_2$; n-heptane→n-heptane/ethyl acetate 95:5) the crude 1-[(R)-3-(tert-butyldimethylsilanyloxy)-2-methyl-propyl]-1H-indazole was obtained as a colorless oil. To this material dissolved in THF (10 mL) at rt was added a solution of TBAF (tetra-n-butylammonium fluoride) in THF (1.0 M, 12 mL, 12 mmol) and the mixture was stirred overnight. The solution was adsorbed onto celite and after flash column chromatography ($SiO_2$; n-heptane→ethyl acetate), (R)-3-Indazol-1-yl-2-methylpropan-1-ol (103) (1.76 g, 45%) was obtained as colorless crystals.

A dry reaction flask was charged with the compound 103 (1.5 mmol), $Et_3N$ (3.0 mmol) in THF (10 mL) and cooled to 0° C. MsCl (0.19 mL, 2.45 mmol) was added dropwise. After 30 min 1 M aqueous $NaHCO_3$ (5 mL) was added, cooling was removed and the mixture stirred for 10 min. The mixture was extracted with ethyl acetate and the combined organic layers were washed with water, 0.5 M HCl, water, 1 M aqueous $NaHCO_3$, brine, dried over $Na_2SO_4$, and evaporated to dryness to give a quantitative yield of the mesylate, compound 104.

(S)-3-(6-methoxy-1H-indazol-1-yl)-2-methylpropyl methanesulfonate (104b)

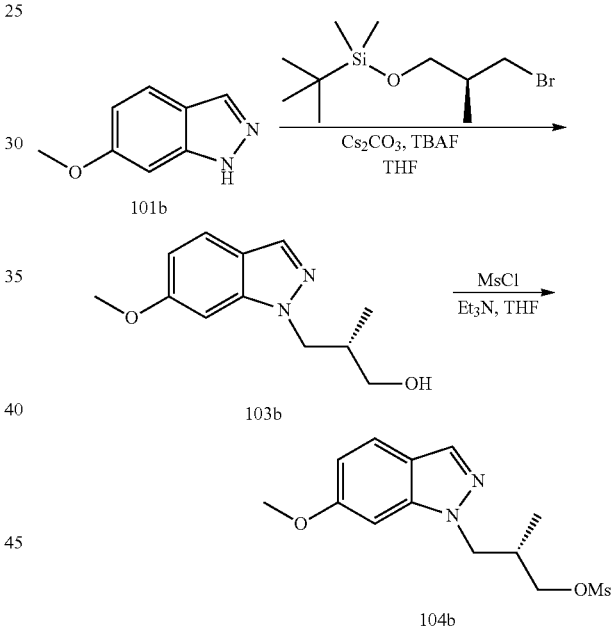

Compound 104b was synthesized according to the same procedure as compound 104. The starting material 6-methoxy-1H-indazole is commercially available from for example Pure Chemistry Scientific Inc.

(S)-1-(3-bromo-2-methylpropyl)-1H-indazole (105)

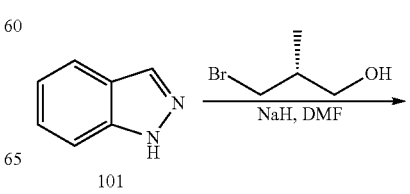

-continued

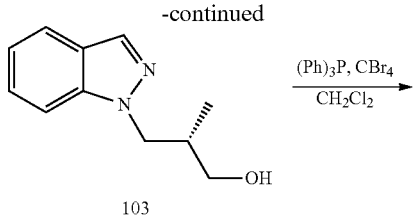

103

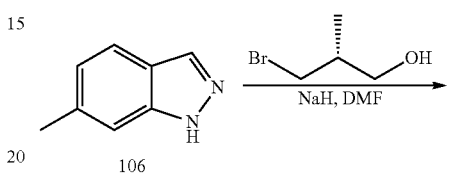

105

The indazole 101 (3 g, 0.025 mol) was taken up in 40 mL of dimethylformamide followed by the addition of 60% sodium hydride (1.27 g, 0.032 mol) in small portions. The mixture was stirred at room temperature for 30 minutes at which time (R)-3-Bromo-2-methyl-1-propanol (4.08 g, 0.027 mol) was added via dropwise addition. The reaction mixture was stirred at room temperature for over the weekend and then poured into 150 mL of water. The desired product was extracted with two 100 mL portions of diethyl ether. The combined extracts was dried over magnesium sulfate and concentrated to a viscous liquid containing unreacted compound 101, compound 103, and the corresponding regioisomer of compound 103. Compound 103 was isolated pure as a colorless liquid from this mixture utilizing silica gel chromatography (elution with 1:1 hexane/ethyl acetate). Yield: 2.1 g (44%); MS [M+H]$^+$ 190.8; $^1$HNMR (CDCl$_3$) δ7.99 (s, 1H), 7.71 (d, 1H), 7.42-7.35 (m, 2H), 7.12 (m, 1H), 4.41 (d, 2H), 3.47-3.36 (m, 2H), 2.32 (m, 1H), 0.97 (d, 3H) ppm.

The alcohol 103 (6.8 g, 0.036 mol) was taken up in dichloromethane (275 mL) and treated with triphenylphosphine (10.36 g) and carbon tetrabromide (13.1 g) respectively. The solution was stirred at room temperature for 1.5 hours at which time the solvent was concentrated to approximately 50 mL (precipitation occurs). The slurry was added to a pad of silica gel eluting with 4:1 hexane/ethyl acetate. Fractions containing the product (least polar) were combined and concentrated to a viscous syrup compound 105. Yield: 6.2 g (69%); MS [M+H]$^+$ 254.8

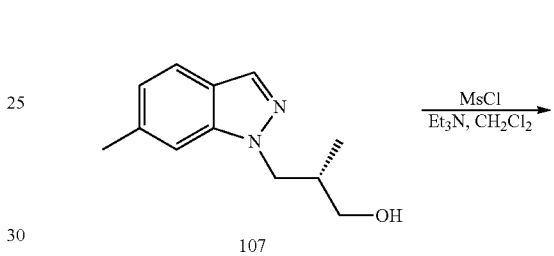

To a stirring solution of compound 103 (0.666 g, 3.50 mmol) in toluene (7.0 mL) was added PBr$_3$ (0.329 mL, 3.50 mmol). The mixture stirred at 55° C. for 1 h. The mixture was cooled to room temperature, quenched with sat. NaHCO$_3$ and extracted with EtOAc (3×100 mL). The org. extracts were washed with brine, dried (MgSO$_4$) and concentrated. The resulting oil was purified via column chromatography, eluting with 20% EtOAc/hexanes to afford compound 105 (0.200 g) as an oil.

(S)-2-methyl-3-(6-methyl-1H-indazol-1-yl)propyl methanesulfonate (108)

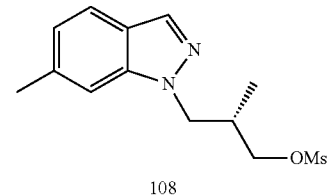

106

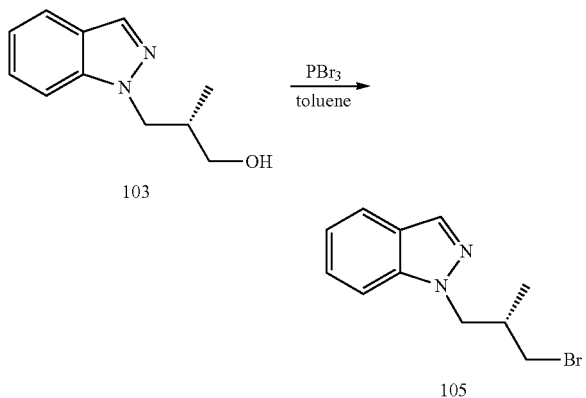

To a stirring solution of 6-methyl indazole 106 (1.0 g, 7.56 mmol) in DMF (20 mL) was added NaH (0.454 g, 11.35 mmol) portion wise. Stirred at rt for 30 min. (R)-3-Bromo-2-methyl-1-propanol (0.833 mL, 7.94 mmol) was added. The mixture stirred at 55° C. for 20 h. The mixture was concentrated, then carefully diluted with water and extracted with EtOAc (3×50 mL). The org. extracts were washed with water, dried (MgSO$_4$) and concentrated. Purified via column chromatography, eluting with 25-45% EtOAc/hexanes to afford compound 107, (R)-3-(6-Methyl-indazol-1yl)-2-methylpropan-1-ol (0.750 g) as a yellow oil.

To a mixture of compound 107 (0.740 g, 3.62 mmol) and Et$_3$N (1.01 mL, 7.24 mmol) in CH$_2$Cl$_2$ (8.0 mL) at 0° C. was added MsCl (0.446 mL, 5.79 mmol) dropwise. The mixture stirred at room temperature for 1.5 h. Quenched carefully with sat. NaHCO$_3$ and diluted with water. Extracted with EtOAc (3×150 mL). The org. extracts were washed with water and brine, dried (Na$_2$SO$_4$) and concentrated. Dried under high vacuum to afford compound 108, (R)-3-(6-Methyl-1H-indazol-1-yl)-propyl methanesulfonate (1.0 g) as a dark yellow oil. No further purification was performed.

(S)-1-(3-bromo-2-methylpropyl)-6-methyl-1H-indazole (108a)

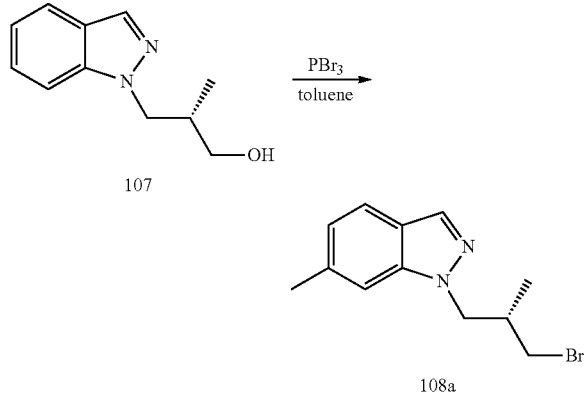

Compounds 107 (640 mg, 3.13 mmol) was dissolved in 30 mL of dry toluene. Tribromophosphine (0.445 mL, 4.72 mmol) was added slowly. The reaction mixture was heated to 55° C. for 1 h and was cooled to rt The reaction mixture was diluted with EtOAc and sat'd NaHCO$_3$ solution to pH>8. Layers were separated and the aqueous layer was extracted with EtOAc three times. Combined organics was washed with sat'd NaCl solution and dried over MgSO$_4$, filtered, and concentrated. Crude product was purified by flash chromatography (15% EtOAc in hexanes) to afford the desired product 108a as a yellow oil (240 mg, 29%). MS and NMR are consistent with the structure.

(S)-1-(3-bromo-2-methylpropyl)-6-(trifluoromethyl)-1H-indazole (111)

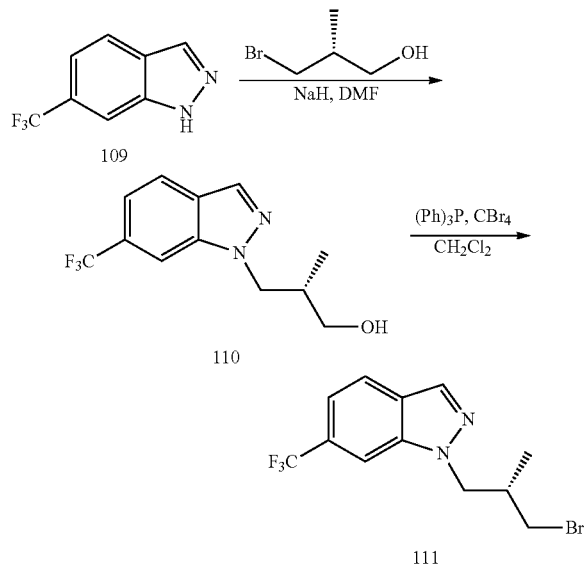

To a stirring solution of 6-trifluoromethyl indazole 109 (1.50 g, 8.06 mmol) in DMF (35.0 mL) was added NaH (0.450 g, 11.25 mmol) portion wise. Stirred at rt for 30 min. NaI (0.420 g, 2.80 mmol) was added, followed by (R)-3- Bromo-2-methyl-1-propanol (1.89 mL, 18.02 mmol). The mixture stirred at 55° C. for 20 h. The mixture was concentrated, then carefully diluted with water and extracted with EtOAc (3×100 mL). The org. extracts were washed with water, dried (MgSO$_4$) and concentrated. Purified via column chromatography, eluting with 40-50% EtOAc/hexanes to afford compound 110 (1.04 g) as a yellow oil.

To a stirring solution of 110 (1.40 g, 4.03 mmol) in CH$_2$Cl$_2$ (23.0 mL) was added PPh$_3$ (1.31 g, 5.01 mmol). Stirred at room temperature for 10 min. CBr$_4$ (1.49 g, 4.49 mmol) was added and the mixture stirred at room temperature for 3 h. The mixture was washed with water, extracted with CH$_2$Cl$_2$ (3×90 mL), dried (MgSO$_4$) and concentrated. Purified via column chromatography, eluting with 20-30% EtOAc/hexanes to afford compound 111 (0.83 g) as a pale yellow oil.

(S)-1-(3-bromo-2-methylpropyl)-6-fluoro-1H-indazole (115)

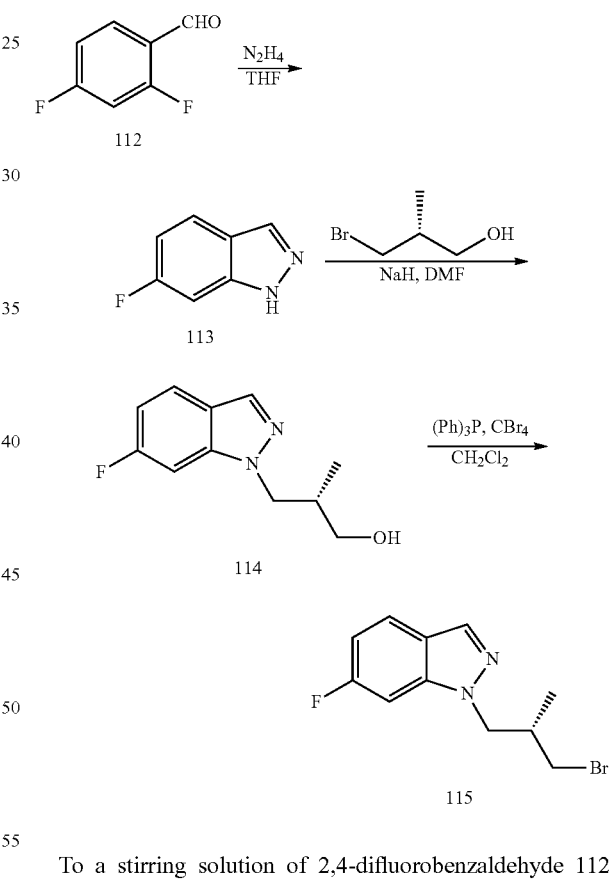

To a stirring solution of 2,4-difluorobenzaldehyde 112 (4.0 g, 28.15 mmol) in THF (18.0 mL) was added hydrazine (24.0 mL, 763 mmol). The mixture was stirred at 105° C. for 2.5 days. The mixture was concentrated to ⅓ its volume. Water was added and the product precipitated out. The solid was filtered off, washed with ample amounts of water and dried in a vacuum oven to afford compound 113 (1.20 g) as a bright yellow solid. No further purification was performed.

To a stirring solution of compound 113 (0.90 g, 6.61 mmol) in DMF (25.0 mL) was added NaH (0.370 g, 9.25 mmol) portion wise. Stirred at rt for 30 min. NaI (0.34 g, 2.26 mmol) was added, followed by (R)-3-Bromo-2-methyl- 1-propanol (0.831 mL, 7.92 mmol). The mixture stirred at 54° C. for 18 h. The mixture was concentrated, then carefully diluted with water and extracted with EtOAc (3×100 mL). The org. extracts were washed with water, dried (MgSO₄) and concentrated. Purified via column chromatography, eluting with 40% EtOAc/hexanes to afford compound 114 (0.63 g) as a colorless oil. This was combined with another lot for a total of 0.850 g.

To a stirring solution of compound 114 (0.85 g, 4.08 mmol) in CH₂Cl₂ (20.0 mL) was added PPh₃ (1.34 g, 5.09 mmol). Stirred at room temperature for 10 min. CBr₄ (1.4 g, 4.22 mmol) was added and the mixture stirred at room temperature for 4 h. The mixture was washed with water, extracted with CH₂Cl₂ (3×100 mL), dried (MgSO₄) and concentrated. Purified via column chromatography, eluting with 70-60% hexanes/EtOAc to afford compound 115 (0.78 g) as a dark yellow oil.

(S)-ethyl 1-(2-methyl-3-((methylsulfonyl)oxy)propyl)-1H-indazole-6-carboxylate (119)

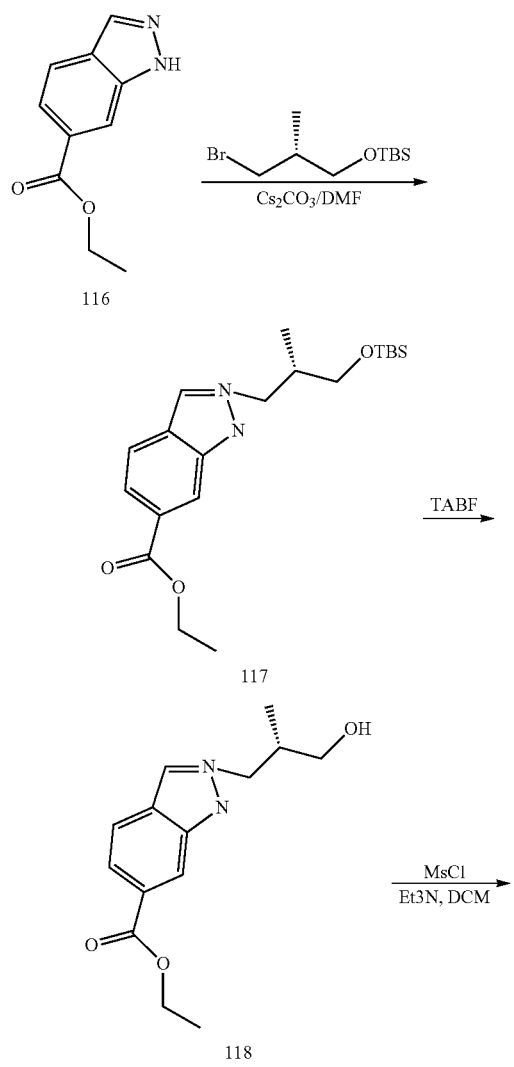

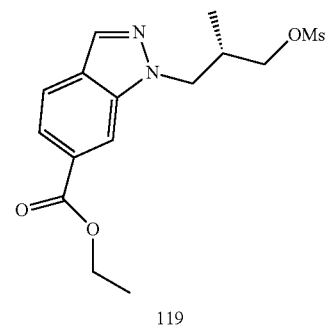

Under an inert atmosphere of nitrogen, a mixture of compound 116 (360 mg, 1.89 mmol), compound (R)-3-Bromo-2-methyl-1-propanol (502 mg, 1.89 mmol), Cs₂CO₃ (1.0 g, 3.08 mmol) in DMF (25 ml) was stirred at 70° C. overnight. Then solvent was evaporated and the residue was purified by flash chromatography (silica gel, PE/EA=50:1) to yield compound 117 (319 mg, yield: 44.9%). LC-MS (ESI): 377 [M+H]⁺

A mixture of compound 117 (319 mg, 0.848 mmol) and TBAF (221 mg, 0.848 mmol) in 20 ml of THF was stirred at room temperature overnight. Upon completion, the resulting solution was concentrated under vacuum to dryness to afford the crude product of compound 118. The crude was purified by flash chromatography (silica gel, PE/EA=1:1) to give compound 118 (220 mg, yield: 99%). LC-MS (ESI): 263 [M+H]⁺

A dry flask was charged with compound 118 (220 mg, 0.84 mmol) and triethylamine (254 mg, 2.52 mmol), and the mixture was cooled to 0° C. with an ice-bath. MsCl (209 mg, 1.34 mmol) was added dropwisely at the same temperature. After 1.5 hours, cooling was removed and the mixture stirred for 10 min. The mixture was extracted with ethyl acetate and the combined organic layers were washed with water, 0.5 M HCl, water, 1 M aqueous NaHCO₃, brine, dried over Na₂SO₄, and evaporated to dryness. The residue was purified by flash chromatography (silica gel, PE/EA=10:1) to afford compound 119 (260 mg, yield: 91%) as a colorless oil. LC-MS (ESI): 341 [M-41]⁺

(S)-1-(3-bromo-2-methylpropyl)-6-methoxy-1H-indazole (123)

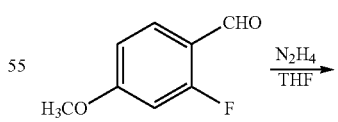

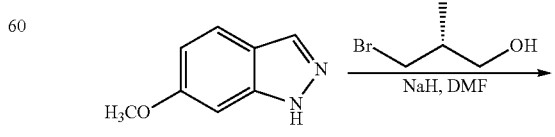

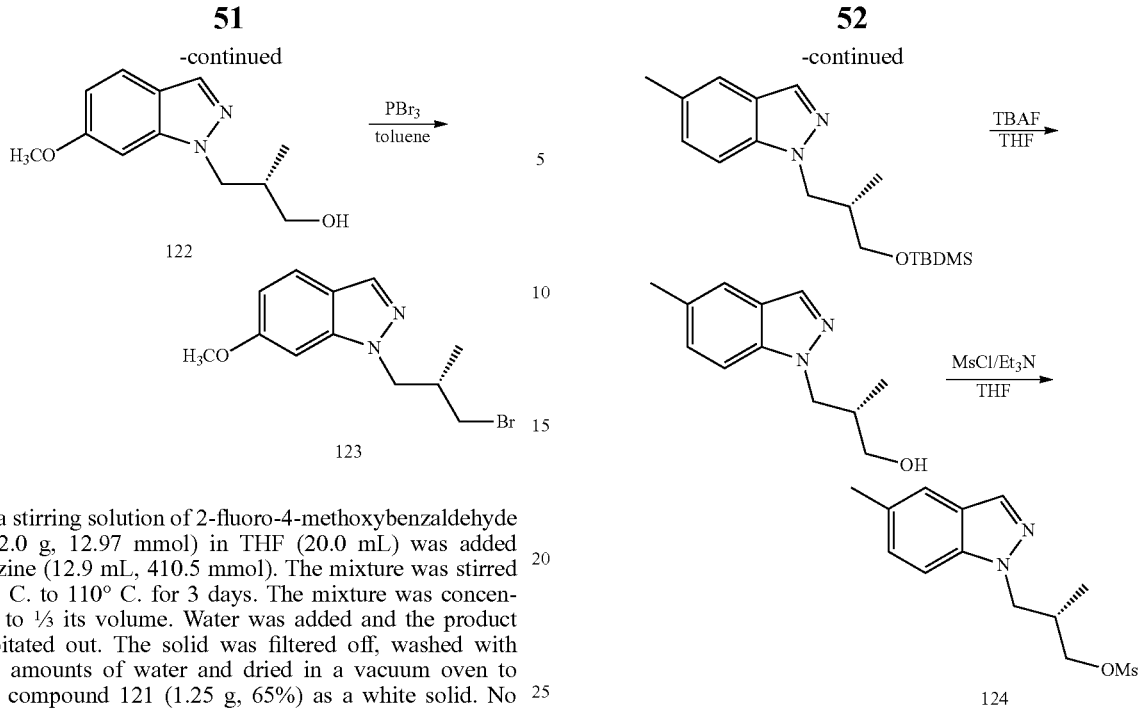

To a stirring solution of 2-fluoro-4-methoxybenzaldehyde 120 (2.0 g, 12.97 mmol) in THF (20.0 mL) was added hydrazine (12.9 mL, 410.5 mmol). The mixture was stirred at 95° C. to 110° C. for 3 days. The mixture was concentrated to ⅓ its volume. Water was added and the product precipitated out. The solid was filtered off, washed with ample amounts of water and dried in a vacuum oven to afford compound 121 (1.25 g, 65%) as a white solid. No further purification was performed.

To a stirring solution of compound 121 (1.20 g, 8.10 mmol) in DMF (25.0 mL) was added NaH (0.453 g, 11.32 mmol) portion wise. Let stir at room temperature for 30 min. (R)-3-Bromo-2-methyl-1-propanol (0.888 mL, 8.39 mmol) was added. The mixture stirred at 52° C. for 48 h. The mixture was cooled to room temperature, diluted with water and extracted with EtOAc (3×100 mL). The org. extracts were washed with water, dried (MgSO$_4$) and concentrated. The resulting oil was purified via column chromatography, eluting with 30-50% EtOAc/hexanes to afford compound 122 (0.540 g, 30%) as a colorless oil. This was combined with another lot for a total of 0.885 g for the next step.

To a stirring solution of compound 122 (0.885 g, 3.88 mmol) in toluene (15.0 mL) was added PBr$_3$ (0.451 mL, 4.80 mmol). The mixture stirred at 55° C. for 20 h. The mixture was cooled to room temperature, quenched with sat. NaHCO$_3$ and extracted with EtOAc (3×100 mL). The org. extracts were washed with brine, dried (MgSO$_4$) and concentrated. The resulting oil was purified via column chromatography, eluting with 40-50% EtOAc/hexanes to afford compound 123 (0.400 g, 35%) as an oil.

(S)-2-methyl-3-(5-methyl-1H-indazol-1-yl)propan-1-ol (124)

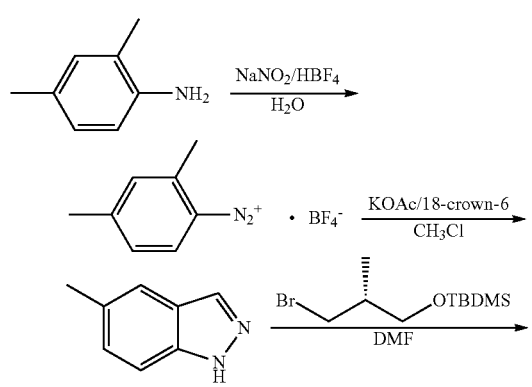

To a solution of 2,4-dimethylaniline (10 g) in 140 ml HBF$_4$ (40% in H$_2$O) the solution of NaNO$_2$ (6.36 g) in water was added at −10° C. slowly. A precipitate formed. The mixture turned red and was stirred for 1 h at 0° C. The solid was filtered and washed with acetone and ethyl ether to give 2,4-dimethylbenzenediazonium tetrafluoroborate (5.25 g). The compound (5.25 g) was added to a mixture of potassium acetate (4.72 g) and 18-crown-6 (0.31 g) in 200 ml chloroform. The mixture was stirred under nitrogen atmosphere for 13 h and thereafter filtered. The filtrate was washed with water, dried over Na$_2$SO$_4$, concentrated under vacuum to give 5-methyl-1H-indazole (1.0 g).

5-methyl-1H-indazole (760 mg), ((R)-3-bromo-2-methylpropoxy)(tert-butyl)dimethylsilane (1.59 g) and CsCO$_3$ were stirred in DMF at 50° C. for 15 h and thereafter the suspension was cooled to rt, water added and the mixture extracted with ethyl acetate and the combined organic layers washed with water and brine, dried over Na$_2$SO$_4$, concentrated and purified by flash column chromatography (SiO$_2$: petroleum ether/ethyl acetate 20:1), to give a colorless oil of (S)-1-(3-((tert-butyldimethylsilyl)oxy)-2-methylpropyl)-5-methyl-1H-indazole (1.12 g).

To a solution of (S)-1-(3-((tert-butyldimethylsilyl)oxy)-2-methylpropyl)-5-methyl-1H-indazole (1.07 g) a 10 ml THF solution of TBAF (0.77 g) was added at rt and the mixture stirred overnight and thereafter the mixture was concentrated and purified by flash column chromatography (SiO$_2$: petroleum ether/ethyl acetate 3:1) to give (S)-2-methyl-3-(5-methyl-1H-indazol-1-yl)propan-1-ol (660 mg).

To a solution of (S)-2-methyl-3-(5-methyl-1H-indazol-1-yl)propan-1-ol (660 mg) and Et$_3$N (1108 mg) in 40 ml THF, MsCl (738 mg) were added slowly at 0° C. and the mixture stirred for 1.5 h at 0° C. and thereafter 5% NaHCO$_3$ aq 20 ml was added and the organic layer extracted by ethyl acetate and dried over sodium sulphate and thereafter concentrated under vacuum to give (S)-2-methyl-3-(5-methyl-1H-indazol-1-yl)propyl methanesulfonate (124) (0.75 g).

Example 1

1-(3-((1R,3r,5S)-3-(cyclopropylmethoxy)-8-azabicyclo[3.2.1]octan-8-yl)-2-methylpropyl)-1H-indazole (301)

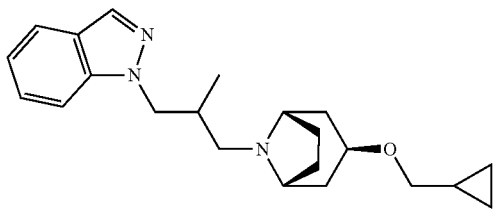 [SMILES: CC(CN1[C@@H]2CC[C@H]1C[C@@H](OCC1CC1)C2)Cn1ncc2ccccc21]

A 4 mL vial was charged with (R,S)-1-(3-chloro-2-methylpropyl)-1H-indazole 102 (0.125 g, 0.60 mmol), 3α-cyclopropylmethoxy-8-azabicyclo[3.2.1]octane 4 (0.054 g, 0.30 mmol), NaI (0.149 g, 1.00 mmol), and K$_2$CO$_3$ (0.138 g, 1.00 mmol) in DMF (1 mL) and stirred at 95° C. for 2 days. The reaction mixture was added water and the product extracted into ethyl acetate. The crude product was purified by cation-exchange column chromatography and then flash column chromatography (SiO$_2$; ethyl acetate) to give the title compound 301 (0.033 g). $^1$H NMR (CDCl$_3$) δ 7.81 (s, 1H), 7.56-7.53 (m, 1H), 7.32-7.30 (m, 1H), 7.20-7.15 (m, 1H), 6.96-6.93 (m, 1H), 4.48-4.44 (m, 1H), 4.04-3.98 (m, 1H), 3.35-3.32 (m, 1H), 3.01 (d, J=6.5 Hz, 2H), 2.94-2.93 (m, 1H), 2.86-2.84 (m, 1H), 2.13-1.96 (m, 3H), 1.82-1.60 (m, 8H), 0.87-0.80 (m, 1H), 0.72 (d, J=6.5 Hz, 3H), 0.34-0.30 (m, 2H), 0.04-0.01 (m, 2H); 13C NMR (CDCl3) δ 140.0, 132.5, 125.8, 123.8, 120.9, 120.2, 109.4, 72.6, 72.3, 59.8, 58.7, 57.2, 53.1, 36.1, 35.9, 34.4, 26.7, 25.9, 16.9, 10.9; HPLC-MS (ammonium acetate) [M+H]+=354.38.

The product was dissolved in acetone and oxalic acid dissolved in acetone was added. The formed crystals were filtered and washed with acetone to give the title compound as oxalic acid salt 301S (0.031 g, total yield 23%).

Example 2

1-((R)-3-((1R,3R,5S)-3-(cyclopropylmethoxy)-8-azabicyclo[3.2.1]octan-8-yl)-2-methylpropyl)-1H-indazole (302)

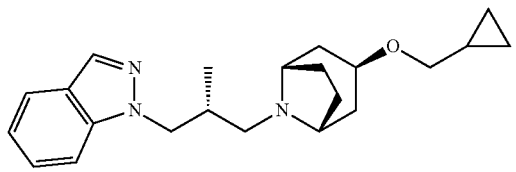 [SMILES: C[C@H](CN1[C@@H]2CC[C@H]1C[C@@H](OCC1CC1)C2)Cn1ncc2ccccc21]

Compound 104 was mixed with the amine 4 (2.3 mmol), N,N-diisopropyl ethyl amine (DIPEA) (2.3 mmol) and THF (1 mL) and shaken at 60° C. overnight. The mixture was diluted with water and extracted with ethyl acetate. The combined organic layers were washed with 1 M aqueous NaHCO$_3$, brine, dried over Na$_2$SO$_4$ and evaporated to dryness. After flash column chromatography (SiO$_2$; ethyl acetate) the title compound 302 was obtained (0.209 g, 28%). $^1$H NMR (CDCl$_3$) δ 7.99 (br s, 1H), 7.73-7.70 (m, 1H), 7.50-7.47 (m, 1H), 7.37-7.32 (m, 1H), 7.14-7.09 (m, 1H), 4.64 (dd, J=13.9, 4.5 Hz, 1H), 4.20 (dd, J=13.9, 7.5 Hz, 1H), 3.52-3.49 (m, 1H), 3.20 (d, J=6.4 Hz, 2H), 3.17-3.02 (m, 2H), 2.31-1.75 (m, 11H), 1.05-0.96 (m, 1H), 0.88 (d, J=6.3 Hz, 3H), 0.52-0.46 (m, 2H), 0.21-0.16 (m, 2H); 13C NMR (CDCl3) δ 139.9, 132.5, 125.8, 123.8, 120.9, 120.2, 109.4, 72.6, 72.3, 59.8, 58.7, 57.2, 53.0, 36.1, 35.9, 34.3, 26.5, 25.9, 16.9, 10.9, 2.8; HPLC-MS (ammonium acetate) [M+H]+=354.14.

Compound 302 was dissolved in acetone and oxalic acid dissolved in acetone was added. The formed crystals were filtered and washed with acetone to give the title compound as oxalic acid salt (302S).

Example 3

1-((R)-3-((1R,3R,5S)-3-(2-Methoxyethyl)-8-azabicyclo[3.2.1]octan-8-yl)-2-methylpropyl)-1H-indazole (303)

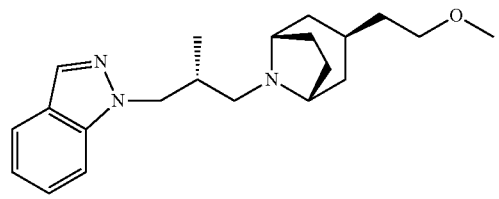 [SMILES: COCC[C@H]1C[C@H]2CC[C@@H](C1)N2C[C@@H](C)Cn1ncc2ccccc21]

Compounds 15 (610 mg, 3.6 mmol) and 105 (455 mg, 1.8 mmol) were dissolved in 20 mL of anhydrous acetonitrile. The reaction mixture was stirred at rt for 3 days. Solvent was removed and the crude product 92 was purified by flash chromatography (5% MeOH* in CH$_2$Cl$_2$, MeOH*=10% 7M NH$_3$/MeOH in MeOH) to afford the desired product compound 92 as a yellowish clear oil (300 mg, 49%). $^1$H NMR (CDCl$_3$) δ 7.97 (d, J=0.8 Hz, 1H), 7.71 (m, 1H), 7.50 (m, 1H), 7.35 (m, 1H), 7.11 (m, 1H), 4.63 (m, 1H), 4.18 (m, 1H), 3.37 (t, J=6.8 Hz, 2H), 3.32 (s, 3 Hz), 3.20-3.18 (m, 2H), 2.31-2.09 (m, 5H), 1.95-1.85 (m, 3H), 1.75-1.75 (m, 2H), 1.63-1.54 (m, 2H), 1.30-1.18 (m, 2H), 0.89 (d, J=6.4 Hz, 3H); $^{13}$C NMR (CDCl$_3$) δ 140.2, 132.7, 126.0, 124.0, 121.1, 120.4, 109.7, 72.2, 60.1, 59.0, 58.8, 57.0, 53.3, 38.2, 36.4, 36.2, 34.6, 27.7, 27.2, 25.1, 17.1; HPLC-MS (ammonium acetate) [M+H]$^+$=342.2.

Compound 303 was dissolved in acetone and oxalic acid dissolved in acetone was added. The formed crystals were filtered and washed with acetone to give the title compound as oxalic acid salt (303S).

Example 4

1-((R)-3-(3-(Cyclopropylmethoxy)-8-aza-bicyclo[3.2.1]octan-8-yl)-2-methylpropyl)-6-methyl-1H-indazole (304)

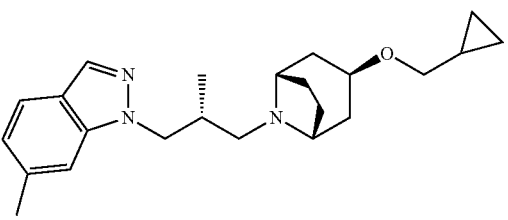 [SMILES: Cc1ccc2cnn(C[C@H](C)CN3[C@@H]4CC[C@H]3C[C@@H](OCC3CC3)C4)c2c1]

To a stirring solution of compound 108 (0.736 g, 2.60 mmol) and compound 4 (0.530 g, 2.92 mmol) in THF (24.0 mL) was added HMDS (1.10 mL, 5.30 mmol) dropwise. Let stir at 46° C. for 3 days. The mixture was concentrated, then purified via column chromatography, eluting with EtOAc (100%) to afford compound 304 (0.058 g) as a yellow oil.

Example 5

1-((R)-3-((1R,3R,5S)-3-(Allyloxy)-8-azabicyclo [3.2.1]octan-8-yl)-2-methylpropyl)-1H-indazole (305)

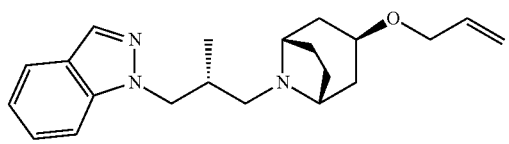 [SMILES: C=CCO[C@H]1C[C@H]2CC[C@@H](C1)N2C[C@@H](C)Cn1ncc2ccccc21]

Compound 17 (0.28 g, 1.68 mmol) was taken up in 3 mL of anhydrous acetonitrile followed by the dropwise addition of a solution of bromide 105 (0.214 g, 0.84 mmol) in acetonitrile (3 mL). The solution was stirred at room temperature for 3 days and then concentrated in vacuo. The crude mixture was taken up in dichloromethane and added to a silica gel column eluting with 5% ammonia/methanol in dichloromethane. Fractions containing only the product were combined and concentrated to give compound 305 as a pale yellow liquid. Yield: 0.193 g (67%).

Compund 305 was dissolved in acetone and oxalic acid dissolved in acetone was added. The formed crystals were filtered and washed with acetone to give the title compound as oxalic acid salt (3035).

Example 6

1-((R)-3-(3-(Cyclopropylmethoxy)-8-aza-bicyclo [3.2.1]octan-8-yl)-2-methylpropyl)-6-(trifluoromethyl)-1H-indazole (306)

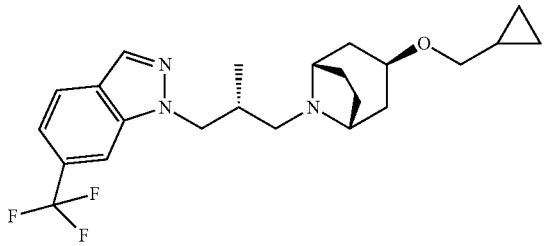 [SMILES: C[C@H](CN1[C@@H]2CC[C@H]1C[C@@H](OCC1CC1)C2)Cn1ncc2ccc(C(F)(F)F)cc21]

To a stirring solution of compound 109 (0.407 g, 1.26 mmol) in CH₃CN (5.0 mL) was added compound 4 (0.458 g, 2.52 mmol). Let stir at room temperature for 4 days. The mixture was concentrated, then purified via column chromatography, eluting with 100% EtOAc —5% MeOH/ EtOAc. The resulting oil was converted to the oxalate salt by dissolving the oil in MTBE (3.0 mL) and adding oxalic acid (0.040 g) as a solution in MTBE (2.0 mL). The mixture was concentrated to afford compound 306 (0.125 g) as an off-white solid.

Example 7

1-((R)-3-(3-(Cyclopropylmethoxy)-8-aza-bicyclo [3.2.1]octan-8-yl)-2-methylpropyl)-6-fluoro-1H-indazole (307)

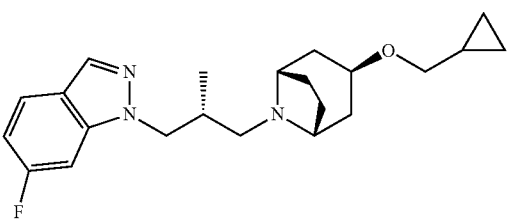 [SMILES: C[C@H](CN1[C@@H]2CC[C@H]1C[C@@H](OCC1CC1)C2)Cn1ncc2ccc(F)cc21]

To a stirring solution of compound 115 (0.180 g, 0.664 mmol) in CH₃CN (3.0 mL) was added compound 4 (0.240 g, 1.32 mmol). Let stir at room temperature for 3 days. The mixture was concentrated, then purified via column chromatography, eluting with 100% EtOAc—100% Acetone as an oil 307. The resulting oil 307 was converted to the oxalate salt by dissolving the oil in MTBE (3.0 mL) and adding oxalic acid (0.036 g) as a solution in MTBE (2.0 mL). The mixture was concentrated to afford compound 307S (0.200 g) as an off-white solid.

Example 8

1-((R)-3-(3-(Allyloxy)-8-aza-bicyclo[3.2.1]octan-8-yl)-2-methylpropyl)-6-fluoro-1H-indazole (308)

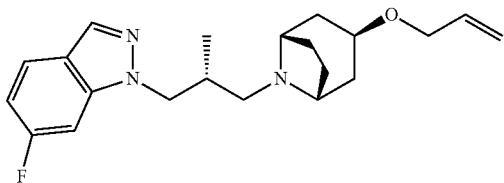 [SMILES: C=CCO[C@H]1C[C@H]2CC[C@@H](C1)N2C[C@@H](C)Cn1ncc2ccc(F)cc21]

To a stirring solution of compound 115 (0.30 g, 1.10 mmol) in CH₃CN (5.0 mL) was added compound 17 (0.37 g, 2.21 mmol). Let stir at room temperature for 5 days. The mixture was concentrated, then purified via column chromatography, eluting with 100% EtOAc—100% Acetone as an oil 308. The resulting oil 308 was converted to the oxalate salt by dissolving the oil in MTBE (3.0 mL) and adding oxalic acid (0.045 g) as a solution in MTBE (2.0 mL). The mixture was concentrated to afford compound 308S (0.220 g) as an off-white solid.

Example 9

1-((R)-3-(3-(2-Methoxyethyl)-8-aza-bicyclo[3.2.1] octan-8-yl)-2-methylpropyl)-6-fluoro-1H-indazole (309)

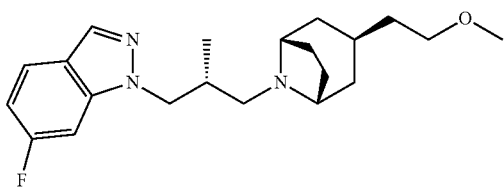 [SMILES: COCC[C@H]1C[C@H]2CC[C@@H](C1)N2C[C@@H](C)Cn1ncc2ccc(F)cc21]

To a stirring solution of compound 115 (0.30 g, 1.10 mmol) in CH$_3$CN (5.0 mL) was added compound 15 (0.374 g, 2.21 mmol). Let stir at room temperature for 5 days. The mixture was concentrated, then purified via column chromatography, eluting with 100% EtOAc—100% Acetone to obtain compound 309 as an oil. The resulting oil 309 was converted to the oxalate salt by dissolving the oil in MTBE (3.0 mL) and adding oxalic acid (0.052 g) as a solution in MTBE (2.0 mL). The mixture was concentrated to afford compound 309S (0.210 g) as an off-white solid.

Example 10

1-((R)-3-((1R,3R,5S)-3-(cyclopropylmethoxy)-8-azabicyclo[3.2.1]octan-8-yl)-2-methylpropyl)-1H-indazol-6-yl)methanol (310)

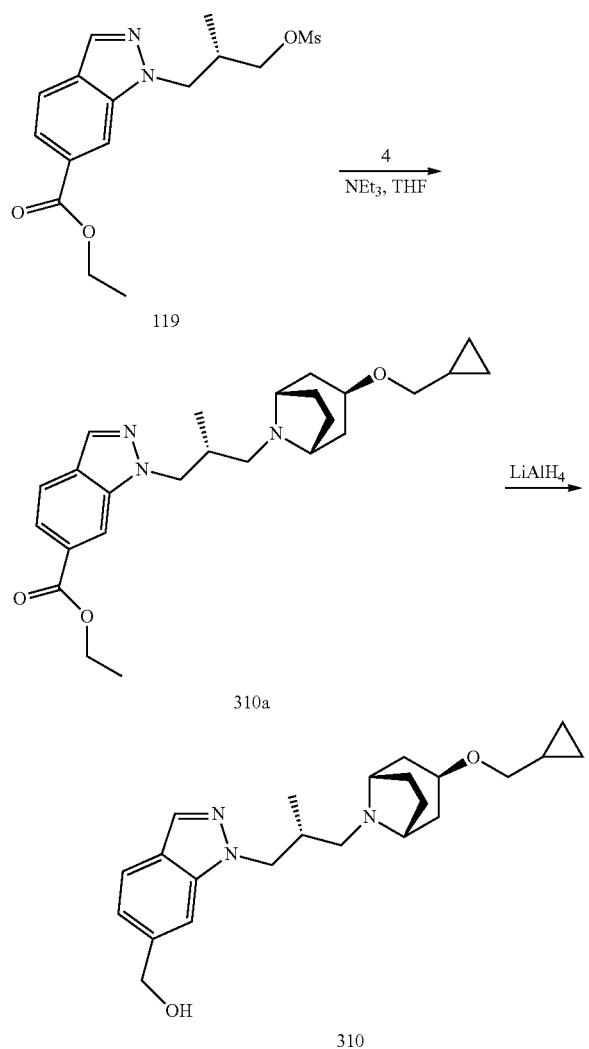

Compound 119 (260 mg, 0.765 mmol) was mixed with compound 4 (207 mg, 1.147 mmol), DIPEA (296 mg, 2.294 mmol) and THF (10 mL) and stirred at 60° C. three days. The mixture was diluted with water and extracted with ethyl acetate. The combined organic layers were washed with 1M aqueous NaHCO$_3$, brine, dried over Na$_2$SO$_4$ and evaporated to dryness. The residue was purified by flash chromatography (silica gel, PE/EA=2:1) and further purified by reverse-phase chromatography (C$_{18}$, 25% methanol/water) to afford compound 310a (60 mg, yield: 18.5%).

A 100-ml round-bottom flask containing a suspension of LiAlH$_4$ (17 mg, 0.470 mmol) in THF (10 ml) was placed in an ice-water bath. To this stirred suspension was added dropwise a solution of compound 310a (60 mg, 0.141 mmol) in THF (5 ml), and this reaction mixture was stirred for an additional 2 hours. Upon completion, the resulting suspension was filtered, and the filtrate was evaporated to dryness. The residue was purified by flash chromatography (silica gel, EtOAc) and then by reverse-phase chromatography (C$_{18}$, 30% CH$_3$CN/water) to afford compound 310 (37 mg, yield: 68.4%). LC-MS (ESI): 384 [M+H]$^+$ A mixture of compound 310 (72 mg, 0.188 mmol) and oxalic acid (17 mg, 0.188 mmol) in 10 ml of acetone was stirred at room temperature for 1 h. The formed crystals were filtered, washed with acetone and dried in vacuo to give compound 310S as oxalic acid salt (26 mg, yield 29.2%) as a white solid. LC-MS (ESI): 384 [M+H]$^+$

Example 11

1-((R)-3-(3-(cyclopropylmethoxy)-8-aza-bicyclo[3.2.1]octan-8-yl)-3-methylpropyl)-6-methoxy-1H-indazole (311)

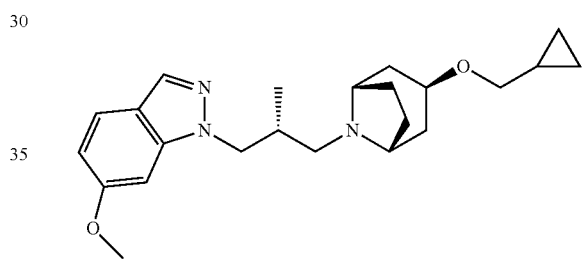

To a stirring solution of compound 123 (0.40 g, 1.41 mmol) in CH$_3$CN (8.0 mL) was added compound 4 (0.512 g, 2.82 mmol). Let stir at room temperature for 3 days. The mixture was concentrated, then purified via column chromatography, eluting with 100% EtOAc—5% MeOH/EtOAc to afford compound 311 (0.165 g, 30%) as a dark oil.

Example 12

1-((R)-3-(3-(cyclopropylmethoxy)-8-aza-bicyclo[3.2.1]octan-8-yl)-3-methylpropyl)-6-methyl-1H-indazole (312)

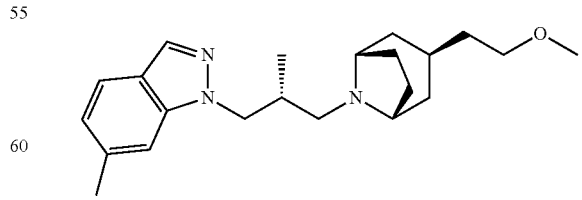

Compounds 15 (302 mg, 1.78 mmol) and 108a (238 mg, 0.89 mmol) were dissolved in 10 mL of anhydrous acetonitrile. The reaction mixture was stirred at rt for 3 days. Solvent was removed and the crude product was purified by flash chromatography (5% MeOH* in CH₂Cl₂, MeOH*=10% 7M NH₃/MeOH in MeOH) to afford the desired product compound 312 as a yellowish clear oil (117 mg, 37%).

Example 13

1-((R)-3-((1R,3R,5S)-3-(2-methoxyethyl)-8-azabicyclo[3.2.1]octan-8-yl)-2-methylpropyl)-6-methoxy-1H-indazole (313)

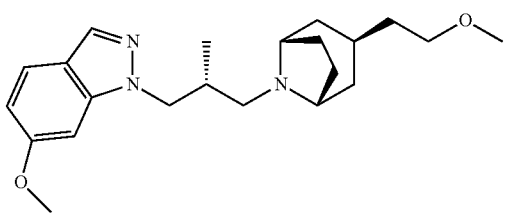 [SMILES: COCC[C@H]1C[C@H]2CC[C@@H](C1)N2C[C@@H](C)Cn1ncc2ccc(OC)cc21]

Compounds 15 (446 mg, 2.63 mmol) and (S)-1-(3-bromo-2-methylpropyl)-6-methoxy-1H-indazole (373 mg, 1.32 mmol) were dissolved in 25 mL of anhydrous acetonitrile. The reaction mixture was stirred at rt for 3 days. Solvent was removed and the crude product was purified by flash chromatography (5% MeOH* in CH₂Cl₂, MeOH*=10% 7M NH₃/MeOH in MeOH) to afford the desired product, compound 313 as a yellowish clear oil (87 mg, 18%). Additional amount of product contaminated with impurities was also obtained.

Example 14

1-((R)-3-((1R,3R,5S)-3-(cyclopentyloxy)-8-azabicyclo[3.2.1]octan-8-yl)-2-methylpropyl)-1H-indazole (314)

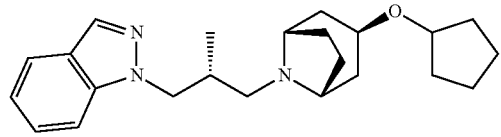 [SMILES: C[C@H](CN1[C@@H]2CC[C@H]1C[C@@H](OC1CCCC1)C2)Cn1ncc2ccccc21]

To the solution of compounds 104 (412 mg, 1.5 mmol) and 18 (300 mg, 1.5 mmol) in THF (15 mL) was added TEA (454 mg, 4.5 mmol). The mixture was stirred at 60° C. under N₂ for about three days. The reaction mixture was diluted with ethyl acetate (50 mL), washed with brine (30 mL). The organic layer was dried with anhydrous sodium sulfate, filtered and concentrated. The residue was purified by chromatography (DCM/Et₃N=100:1-50:1) to afford a yellow oil compound 314 (55 mg).

To the solution of compound 314 (55 mg, 015 mmol) in CH₃COOEt (2 mL) was added slowly the solution of oxalic acid (13 mg, 0.15 mmol) in ether (2 mL). The mixture was stirred for 0.5 h at room temperature. The suspension was filtered and washed with ether (2 mL) to afford a white solid compound 314S (46 mg, with 98.5% purity).

Example 15

1-((R)-3-(3-(cyclobutylmethoxy)-8-aza-bicyclo[3.2.1]octan-8-yl)-2-methylpropyl)-1H-indazole (315)

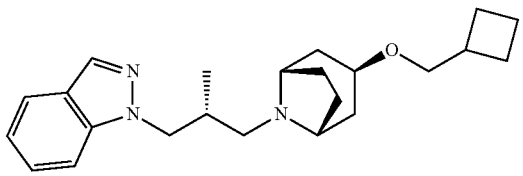 [SMILES: C[C@H](CN1[C@@H]2CC[C@H]1C[C@@H](OCC1CCC1)C2)Cn1ncc2ccccc21]

To a stirring solution of compound 105 (0.453 g, 1.79 mmol) in CH₃CN (8.0 mL) was added compound 22 (0.70 g, 3.58 mmol). Let stir at room temperature for 3 days. The mixture was concentrated, then purified via column chromatography, eluting with 100% EtOAc—5% MeOH/EtOAc to afford compound 315 (0.332 g) as a dark oil.

Example 16

1-((R)-3-(3-(cyclopropylmethoxy)-8-aza-bicyclo[3.2.1]octan-8-yl)-2-methylpropyl)-3-methyl-1H-indazole (316)

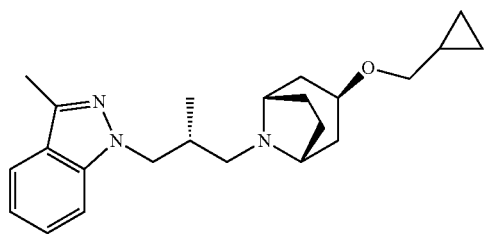 [SMILES: Cc1nn(C[C@H](C)CN2[C@@H]3CC[C@H]2C[C@@H](OCC2CC2)C3)c2ccccc12]

To a THF (8 ml) solution of starting material 23 ((R)-3-((1R,3R,5S)-3-(cyclopropylmethoxy)-8-azabicyclo[3.2.1]octan-8-yl)-2-methylpropan-1-ol) (161 mg), 3-methyl-1H-indazole (100 mg, commercially available from for example Sigma Aldrich) and PPh₃ (500 mg) at 0° C. under nitrogen atmosphere DEAD (Diethyl azodicarboxylate) (386 mg) was added dropwise. The mixture was stirred at room temperature overnight. Flash column chromatography resulted in 1-((R)-3-(3-(cyclopropylmethoxy)-8-aza-bicyclo[3.2.1]octan-8-yl)-2-methylpropyl)-3-methyl-1H-indazole (0.04 g) being obtained. Yield: 17.2%; m/z=368[M+H]⁺

Example 17

1-((R)-3-(3-(cyclopropylmethoxy)-8-aza-bicyclo[3.2.1]octan-8-yl)-2-methylpropyl)-7-methyl-1H-indazole (317)

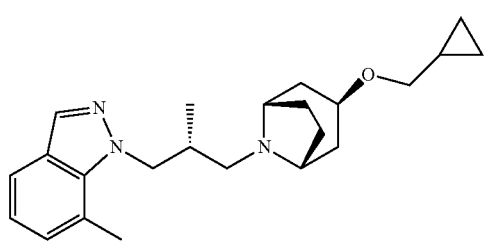 [SMILES: Cc1cccc2cnn(C[C@H](C)CN3[C@@H]4CC[C@H]3C[C@@H](OCC3CC3)C4)c12]

To a THF (8 ml) solution of starting material 23 ((R)-3-((1R,3R,5S)-3-(cyclopropylmethoxy)-8-azabicyclo[3.2.1]octan-8-yl)-2-methylpropan-1-ol) (161 mg), 7-methyl-1H-indazole (100 mg, commercially available from for example Sigma Aldrich) and PPh₃ (500 mg) at 0° C. under nitrogen atmosphere DEAD (Diethyl azodicarboxylate) (386 mg) was added dropwise. The mixture was stirred at room temperature overnight. Flash column chromatography resulted in 1-((R)-3-(3-(cyclopropylmethoxy)-8-aza-bicyclo[3.2.1]octan-8-yl)-2-methylpropyl)-7-methyl-1H-indazole (0.04 g) being obtained. Yield: 4.3%; m/z=368[M+H]⁺.

Example 18

1-((R)-3-((1R,3R,5S)-3-(prop-2-ynyloxy)-8-azabicyclo[3.2.1]octan-8-yl)-2-methylpropyl)-1H-indazole (318)

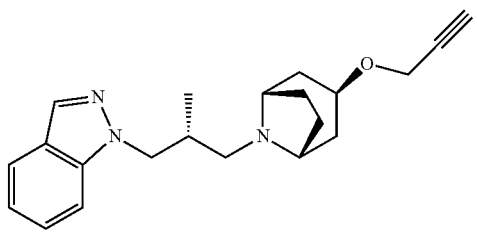 [SMILES: C#CCO[C@H]1C[C@H]2CC[C@@H](C1)N2C[C@@H](C)Cn1ncc2ccccc21]

To a solution of starting material 104 (455 mg, 1.69 mmol) and starting material 16 (400 mg, 2.42 mmol) in 15 ml THF, was added TEA (512 mg, 5.07 mmol). The mixture was stirred at 60° C. under N₂ for about three days. The reaction mixture was diluted with ethyl acetate (50 mL), washed with brine (30 mL). The organic layer was dried over anhydrous Na₂SO₄, filtered, concentrated and purified by silica gel (ethyl acetate:petroleum ether=1:5~1:1) to give 1-((R)-3-((1R,3R,5S)-3-(prop-2-ynyloxy)-8-azabicyclo[3.2.1]octan-8-yl)-2-methylpropyl)-1H-indazole (50 mg, 8.8%).

50 mg of compound 318 was dissolved in ether 6 ml, then oxalic acid dihydrate 19 mg in ether 6 ml was added to the solution. The mixture was stirred at rt overnight. Concentrate to give a white solid. The solid was dissolved in acetone, precipitate with ether afford 1-((R)-3-((1R,3R,5S)-3-(prop-2-ynyloxy)-8-azabicyclo[3.2.1]octan-8-yl)-2-methylpropyl)-1H-indazole oxalate (318s) (45 mg, 71%) as a white powder; ESI-MS m/z: 338.3[M+H⁺].

Example 19

1-((R)-3-(3-(propoxy)-8-aza-bicyclo[3.2.1]octan-8-yl)-2-methylpropyl)-1H-indazole (319)

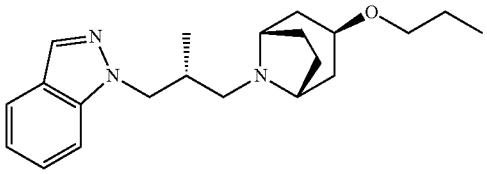 [SMILES: CCCO[C@H]1C[C@H]2CC[C@@H](C1)N2C[C@@H](C)Cn1ncc2ccccc21]

A mixture of starting material 104 (450 mg, 1.68 mmol) and starting material 24 (288 mg, 1.70 mmol) in 15 ml THF, was added TEA (509 mg, 5.04 mmol). The mixture was stirred at 60° C. under N₂ for about three days. The reaction mixture was diluted with ethyl acetate (50 mL), washed with brine (30 mL). The organic layer was dried over anhydrous Na₂SO₄, filtered, concentrated. The residue was purified by column chromatography (DCM/MeOH=100:1-20:1) to afford 1-((R)-3-(3-(propoxy)-8-aza-bicyclo[3.2.1]octan-8-yl)-2-methylpropyl)-3-methyl-1H-indazole (69 mg, 12%); LC-MS (ESI): 342[M+H]⁺

To a solution of 1-((R)-3-(3-(propoxy)-8-aza-bicyclo[3.2.1]octan-8-yl)-2-methylpropyl)-1H-indazole (69 mg, 0.202 mmol) in 3 ml of acetone was added dropwise oxalic acid dihydrate (26 mg, 0.206 mmol) in 1 ml of acetone. The mixture was stirred at rt 5 h. The solvents were removed and 1-((R)-3-(3-(propoxy)-8-aza-bicyclo[3.2.1]octan-8-yl)-2-methylpropyl)-1H-indazole oxalate (319s) (60 mg) was obtained; LC-MS (ESI): 342[M+H]⁺.

Example 20

1-((R)-3-((1R,3R,5S)-3-(2-methoxyethylidene)-8-azabicyclo[3.2.1]octan-8-yl)-2-methylpropyl)-1H-indazole (320)

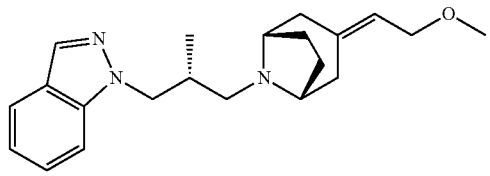 [SMILES: COC/C=C1\C[C@H]2CC[C@@H](C1)N2C[C@@H](C)Cn1ncc2ccccc21]

To a solution of starting material 104 (450 mg, 1.68 mmol) and starting material 25 (300 mg, 1.79 mmol) in 15 ml THF, was added TEA (509 mg, 5.04 mmol). The mixture was stirred at 60° C. under N₂ for about three days. The reaction mixture was diluted with ethyl acetate (50 mL), washed with brine (30 mL). The organic layer was dried over anhydrous Na₂SO₄, filtered, concentrated and purified by silica gel (DCM/Et₃N=100:1-50:1) to give 1-((R)-3-((1R,3R,5 S)-3-(2-methoxyethylidene)-8-azabicyclo[3.2.1]octan-8-yl)-2-methylpropyl)-1H-indazole (320) (60 mg).

To a solution of 1-((R)-3-((1R,3R,5S)-3-(2-methoxyethylidene)-8-azabicyclo[3.2.1]octan-8-yl)-2-methylpropyl)-1H-indazole in ethyl acetate (3 mL) was added slowly the solution of oxalic acid dihydrate (23 mg, 0.18 mmol) in ether (3 mL). The mixture was stirred for 0.5 h at room temperature. The suspension was filtered and washed with ether (3 mL) to give 1-((R)-3-((1R,3R,5S)-3-(2-methoxyethylidene)-8-azabicyclo[3.2.1]octan-8-yl)-2-methylpropyl)-1H-indazole oxalate (320s) (60 mg) as a white solid; ESI-MS m/z: 340.3[M+H⁺]

Example 21

1-((R)-3-(3-(cyclopropylmethoxy)-8-aza-bicyclo[3.2.1]octan-8-yl)-2-methylpropyl)-5-methyl-1H-indazole (321)

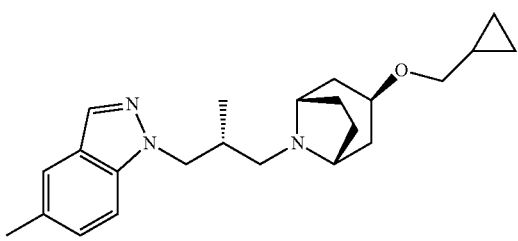 [SMILES: Cc1ccc2c(cnn2C[C@H](C)CN2[C@@H]3CC[C@H]2C[C@@H](OCC2CC2)C3)c1]

Starting material 124 (0.35 g) was mixed with starting material 4 (0.27 g) and Et₃N (0.25 g) in 5 ml THF. The resulting mixture was stirred at 40° C. for 5 days. Water was thereafter added to the mixture and the organic layer extracted by ethyl acetate, washed with 1M NaHCO₃ and brine, dried over sodium sulphate and concentrated under vacuum and the residue purified by flash column chromatography (SiO₂:Ethyl acetate) to give 1-((R)-3-(3-(cyclopropylmethoxy)-8-aza-bicyclo[3.2.1]octan-8-yl)-2-methylpropyl)-5-methyl-1H-indazole (321) (30 mg).

Example 22

1-((R)-3-((1R,3R,5S)-3-(prop-2-ynyloxy)-8-azabicyclo[3.2.1]octan-8-yl)-2-methylpropyl)-6-methoxy-1H-indazole (322)

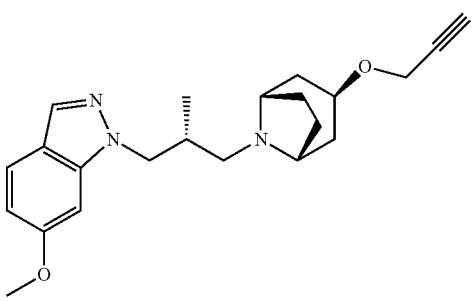 [SMILES: C#CCO[C@H]1C[C@H]2CC[C@@H](C1)N2C[C@@H](C)Cn1ncc2ccc(OC)cc21]

To a solution of starting material 104b (380 mg, 1.28 mmol) and starting material 16 (215 mg, 1.30 mmol) in THF 15 ml, was added TEA (388 mg, 3.84 mmol). The mixture was stirred at 60° C. under N₂ for about three days. The reaction mixture was diluted with ethyl acetate (50 mL), washed with brine (30 mL). The organic layer was dried over anhydrous Na₂SO₄, filtered, concentrated and purified by silica gel (ethyl acetate:petroleum ether=1:5-1:1) to give 1-((R)-3-((1R,3R,5S)-3-(prop-2-ynyloxy)-8-azabicyclo[3.2.1]octan-8-yl)-2-methylpropyl)-6-methoxy-1H-indazole (80 mg, 17%).

80 mg 1-((R)-3-((1R,3R,5S)-3-(prop-2-ynyloxy)-8-azabicyclo[3.2.1]octan-8-yl)-2-methylpropyl)-6-methoxy-1H-indazole was dissolved in ether/acetone (1:1) 6 ml, then oxalic acid dihydrate 27 mg in ether 8 ml was added to the solution. The mixture was stirred at rt overnight, filtered and lyophilized to afford 1-((R)-3-((1R,3R,5S)-3-(prop-2-ynyloxy)-8-azabicyclo[3.2.1]octan-8-yl)-2-methylpropyl)-6-methoxy-1H-indazole oxalate (322s) (65 mg, 68%) as a white powder; ESI-MS m/z: 368.3[M+H⁺]

Example 23

1-((R)-3-((1R,3R,5S)-3-(2-ethoxyethyl)-8-azabicyclo[3.2.1]octan-8-yl)-2-methylpropyl)-1H-indazole (323)

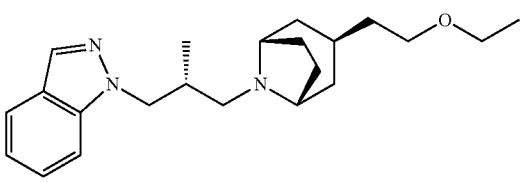 [SMILES: CCOCC[C@H]1C[C@H]2CC[C@@H](C1)N2C[C@@H](C)Cn1ncc2ccccc21]

Starting material 105 (100 mg) and starting material 13 (72 mg) were dissolved in dry toluene and heated at 90° C. overnight. The mixture was thereafter evaporated under vacuum, extracted by DCM, washed with brine, dried and evaporated in vacuum to afford crude oil. The crude was purified on silica gel eluting by 1%(NH₃/MeOH) in DCM to give 1-((R)-3-((1R,3R,5 S)-3-(2-ethoxyethyl)-8-azabicyclo[3.2.1]octan-8-yl)-2-methylpropyl)-1H-indazole (323), yield 14.3% (20 mg); LCMS: 356 [ESI, M+H⁺].

Example 24

1-((R)-3-((1R,3R,5S)-3-(2-ethoxyethyl)-8-azabicyclo[3.2.1]octan-8-yl)-2-methylpropyl)-6-methyl-1H-indazole (324)

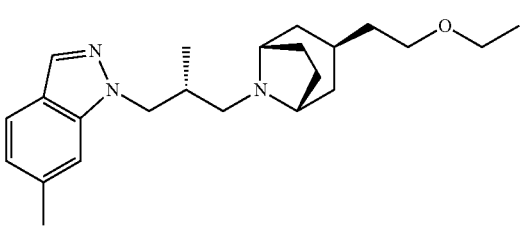 [SMILES: CCOCC[C@H]1C[C@H]2CC[C@@H](C1)N2C[C@@H](C)Cn1ncc2ccc(C)cc21]

To a solution of compound 108 (450 mg, 1.59 mmol) and compound 13 (291 mg, 1.59 mmol) in THF 15 ml, was added TEA (482 mg, 4.77 mmol). The mixture was stirred at 60° C. under N₂ for about 5 days. The reaction mixture was diluted with ethyl acetate, washed with brine. The organic layer was dried over anhydrous Na₂SO₄, filtered and concentrated. Flash chromatography (DCM with 1% MeOH) gives 1-((R)-3-((1R,3R,5S)-3-(2-ethoxyethyl)-8-azabicyclo[3.2.1]octan-8-yl)-2-methylpropyl)-6-methyl-1H-indazole (324) (64 mg).

Example 25

1-((R)-3-(3-(cyclopropylmethoxy)-8-aza-bicyclo[3.2.1]octan-8-yl)-2-methylpropyl)-6-methyl-1H-indazole (325)

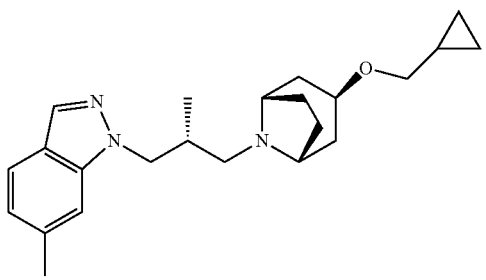 [SMILES: Cc1ccc2cnn(C[C@H](C)CN3[C@@H]4CC[C@H]3C[C@@H](OCC3CC3)C4)c2c1]

Compound 108 (0.35 g) was mixed with compound 4 (0.27 g) and Et₃N (0.25 g) in 5 ml THF. The resulting mixture was stirred at 40° C. for 5 days. Water was thereafter added to the mixture and the organic layer extracted by ethyl acetate, washed with 1M NaHCO₃ and brine, dried over sodium sulphate and concentrated under vacuum and the residue purified by flash column chromatography (SiO₂: Ethyl acetate) to give 1-((R)-3-(3-(cyclopropylmethoxy)-8-aza-bicyclo[3.2.1]octan-8-yl)-2-methylpropyl)-6-methyl-1H-indazole (325) (29 mg), also exemplified in example 4 as compound (304)

Example 26

1-((R)-3-(3-(Allyloxy)-8-aza-bicyclo[3.2.1]octan-8-yl)-2-methylpropyl)-1H-indazole (326)

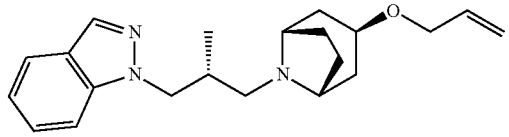 [SMILES: C=CCO[C@H]1C[C@H]2CC[C@@H](C1)N2C[C@@H](C)Cn1ncc2ccccc21]

To a stirring solution of compound 105 (0.28 g, 1.10 mmol) in CH₃CN (5.0 mL) was added compound 17 (0.37 g, 2.21 mmol). Let stir at room temperature for 5 days. The mixture was concentrated, then purified via column chromatography, eluting with 100% EtOAc—100% Acetone gave compound 326. The resulting oil 326 was converted to the oxalate salt by dissolving the oil in MTBE (3.0 mL) and adding oxalic acid (0.045 g) as a solution in MTBE (2.0 mL). The mixture was concentrated to afford compound 326S (0.220 g) as an off-white solid.

Screening of Test Compounds in an Assay Using Muscarinic Receptor Subtypes M₁, M₂, and M₃ R-SAT Assays Receptor Selection and Amplification Assays (RSAT™) were performed on human M₁, M₂, and M₃ muscarinic acetylcholine receptors essentially as previously described (Spalding et al., 2002; 2006). Briefly, NIH-3T3 cells were grown in 96-well tissue culture plates to 70% to 80% confluence. Cells were transfected with plasmid DNAs using Superfect Reagent (QIAGEN, Valencia, Calif.) as per the manufacturer's protocols. After 16-22 hours, medium was replaced with DMEM containing 1% PSG, 0.5% calf serum, 25% Ultraculture synthetic supplement (Cambrex, Walkersville, Md.) instead of calf serum, and the indicated concentrations of ligand. Cells were then grown in a humidified atmosphere with 5% ambient CO₂ for 4 to 6 days. Media were then removed from the plates, and beta-galactosidase activity was measured by the addition of o-nitrophenyl-D-galactopyranoside (in phosphate-buffered saline with 5% NP-40 detergent). The resulting colorimetric reaction was measured in a spectrophotometric plate reader (Titertek, Helsinki, Finland) at 420 nM. All data represent the mean of three wells and were analyzed using the computer program Excel Fit, and EC50 determinations were made using least-squares fit analysis with GraphPad Software Inc. (San Diego, Calif.) software.

The results, which demonstrate the agonist activity of several compounds described herein, are below presented in Table 1.

TABLE 1

Activity at muscarinic receptors.

| Compound | M1 PEC50 AVG | M1 EFF % AVG | M2 PEC50 AVG | M2 EFF % AVG | M3 PEC50 AVG | M3 EFF % AVG | M1 GTPγS PEC50 AVG | M1 GTPγS EFF % AVG |
|---|---|---|---|---|---|---|---|---|
| 302S | 8.9 | 111 | 7.6 | 153 | 6.8 | 12 | 8.5 | 98 |
| 303S | 8.4 | 121 | 7.1 | 102 | — | 8 | 7.2 | 67 |
| 304 | 8.9 | 110 | 7.6 | 108 | 7.4 | 9 | 8.3 | 67 |
| 305 | 8.1 | 115 | 6.9 | 107 | — | 4 | 7.1 | 70 |
| 307 | 9.5 | 156 | 7.7 | 198 | 7.3 | 19 | 8.0 | 63 |
| 308 | 8.9 | 131 | 7.4 | 152 | 6.3 | 18 | 7.1 | 66 |
| 309 | 9.4 | 123 | 7.5 | 176 | 6.9 | 18 | 7.3 | 53 |
| 310s | 7.5 | 96 | | 27 | | 6 | 6.2 | 62 |
| 311 | 8.0 | 120 | 6.9 | 65 | | 2 | 7.3 | 55 |
| 312 | 9.3 | 105 | 7.5 | 137 | 6.3 | 17 | 7.9 | 64 |
| 313 | 8.2 | 116 | 7.3 | 111 | | 7 | 7.4 | 49 |
| 314s | 8.4 | 104 | 7.3 | 74 | | 8 | 7.6 | 48 |
| 315 | 8.1 | 100 | 7.3 | 47 | | 5 | 7.3 | 36 |
| 316 | 7.9 | 78 | 6.6 | 81 | — | 5 | 7.5 | 88 |
| 317 | 7.6 | 81 | 6.9 | 46 | — | 2 | 7.0 | 85 |
| 318s | 8.0 | 122 | 7.2 | 92 | — | 8 | 7.1 | 66 |
| 319s | 8.1 | 111 | 7.5 | 102 | — | 3 | 6.7 | 63 |
| 320s | 8.2 | 109 | 7.2 | 90 | — | 8 | 6.8 | 60 |
| 321 | 7.9 | 75 | 8.1 | 19 | — | 3 | 7.2 | 56 |
| 322s | 8.0 | 86 | 7.1 | 44 | — | 5 | 7.1 | 42 |
| 323 | 9.1 | 66 | 7.8 | 34 | — | -2 | 7.7 | 32 |
| 324 | 9.1 | 82 | 7.9 | 45 | — | 17 | 8.2 | 31 |

TABLE 1-continued

Activity at muscarinic receptors.

| Compound | M1 PEC50 AVG | M1 EFF % AVG | M2 PEC50 AVG | M2 EFF % AVG | M3 PEC50 AVG | M3 EFF % AVG | M1 GTPγS PEC50 AVG | M1 GTPγS EFF % AVG |
|---|---|---|---|---|---|---|---|---|
| 325 | 8.9 | 110 | 7.6 | 108 | 7.4 | 9 | 8.3 | 67 |
| 326s | 8.1 | 115 | 6.9 | 107 | — | 4 | 7.1 | 70 |
| Comparative examples | | | | | | | | |
| Pilocarpine | 5.8 | 94 | 5.8 | 90 | 5.4 | 56 | 6.1 | 67 |
| Comparative compound 2 | 9.0 | 126 | 7.1 | 52 | 7.1 | 30 | 7.9 | 32 |

Table 1: pEC50 is the negative logarithm of the concentration of compound causing 50 percent of its maximal effect, and EFF % is the percent efficacy compared to the maximum effect of the reference compound carbachol which is set at 100 percent; GTPγS is GTPγS binding assays and a detailed description on how to perform the assay has been published by Bradley et al in Neuropharmacology 58 (2010) p.365-373. Pilocarpine is a non-selective muscarinic receptor agonist and comparative compound 2 is previously known muscarinic receptor agonist (AC00263201)

IOP Lowering Effect

Intraocular pressure (IOP) was measured in laser-induced unilaterally ocular hypertensive conscious Cynomolgus monkeys by applanation pneumatonometry at t=0 (immediately pre-dose), 2, 4, 6, 24 h. A single dose of the test compound was administered topically to the hypertensive eye while vehicle was given to the fellow eye. The intraocular pressure taken before the eye drop administration (0 hours) was used as a baseline value. All animals were evaluated for changes in pupil diameter and apparent discomfort throughout the course of the experiments. Student's paired t-test was used for statistical comparisons. Differences were considered statistically significant if the P-value is less than 0.05. The peak IOP decrease over the first 6 h was expressed as a percent change from the baseline IOP value (TDFB). The peak IOP lowering with compounds disclosed herein is greater than comparative compound 2 (FIG. 1). The IOP decrease caused by the compounds lasted for at least 24 h. These compounds disclosed herein also exhibit greater efficacy than comparative compound 2 in the in vitro M1 GTPγS assay (Table 1). FIG. 1 shows that for compounds disclosed herein there is a correlation (P=0.05, $R^2$=0.51) between the peak % efficacy in the monkey IOP lowering experiments and the % efficacy in the M1 GTPγS assay.

Methods for Tear Secretion

Compounds disclosed herein, (302s, 303s, and 305) were compared to Comparative Compound 2 and/or Pilocarpine. Naïve, awake balb/c mice are gently scruffed at the neck, and tear production is measured by placing a Zone Quick Sterile Standardized Phenol Red Thread into the inferior conjunctiva sac of the right eye for 30 seconds. The tear distance, in mm, is recorded. The mice were not anesthetized or otherwise sedated. Tear secretion is measured at baseline, after which a 5 µl drop of 0.1% 302s, 303s, or 305 or vehicle or 20 µl standard drop of 0.2% Pilocarpine is applied to each eye, and tear secretion is measured again 1, 3, 6, and/or 24 hours post-dosing. Data are analyzed by repeated measures ANOVA with post-hoc Bonferroni comparisons to vehicle. All data are shown in FIG. 2 and Table 2. In the longest time-course study (the pilocarpine 24-hour study), the compound (302s) and pilocarpine showed statistically significant improved tear secretion at 3 and 6 hours post-dosing, and compound 302s showed a trend toward significance at 24 hours, compared to vehicle, but the effect on tear secretion with Comparative Compound 2 was not significantly different from vehicle. The enhancement of tear secretion by the compound exceeded the effect of pilocarpine at all time points. Further details can be seen in FIG. 2. In other studies using the same method (see Table 2), additional compounds disclosed herein (303s and 305) were shown to have effects on tear secretion greater than that of Comparative Compound 2 that were statistically significant compared to vehicle.

TABLE 2

Tear secretion studies

| | 1 hr | |
|---|---|---|
| Vehicle | 96% | |
| Comparative Compound 2 | 149% * | |
| 302 s | 156% * | |
| 305 | 163% * | |

| | 1 hr | 3 hr |
|---|---|---|
| Vehicle | 106% | 100% |
| Comparative Compound 2 | 113% | 123% |
| 302 s | 157% * | 155% * |
| 303 s | 131% | 134% * |

| | 3 hr | 6 hr | 24 hr |
|---|---|---|---|
| Vehicle | 112% | 97% | 98% |
| Pilocarpine | 142% * | 136% * | 113% |
| Comparative Compound 2 | 134% | 110% | 98% |
| 302 s | 152% * | 151% * | 120% † |

For all studies, there was a significant effect of treatment and a significant treatment × time interaction (2-way repeated measures ANOVA). Significance from vehicle using post hoc Bonferroni comparisons are indicated by an asterisk (*), and are significant at P < 0.05. A trend (P = 0.1) is indicated by †.

Methods for Pharmacokinetic Evaluation

The experimental animals were normotensive male New Zealand White rabbits. A single drop (35 µl) of a compound, (302s), at a concentration of 0.126% (corrected for oxalate salt weight) was administered to each eye by pipette. At 0.25, 0.5, 1, 2, 4, 8, and 24 hours, plasma, aqueous humor, vitreous humor, cornea, iris-ciliary body, retina, and choroid were collected (2 rabbits/timepoint, or 4 eyes/timepoint). Approximately 0.5 ml of blood was collected and placed in EDTA tubes. Blood samples were kept on ice during the duration of sample collection, and centrifuged to harvest plasma. Animals were euthanized and ocular tissues were collected and placed in vials and kept on dry ice for the duration of the collections. All ocular tissue and plasma samples were stored at or below −60° C. until bioanalysis. In all tissues, the $T_{max}$ for the compound was 0.25 hr.

Maximal plasma concentration ($C_{max}$) for the compound was 6.4 ng/g. The plasma concentration at most timepoints was >100-fold lower than the compound concentration in target ocular tissues (iris/ciliary body, cornea, retina). The concentration of compound 302s in the target ocular tissues remained at active levels up to at least 24 h. The analysis of all tissues is reported in FIG. 3. Abbreviations used in FIG. 3 have the following meanings AH (Aqueous Humor), VH (Vitreous Humor) ICB (Iris Ciliary Body), CenP Retina (Center Punch Retina), Per Retina (Peripheral Retina) CenP Choroid (Center Punch Choroid), and Per Choroid (Peripheral Choroid)

What is claimed is:

1. A compound of formula (I):

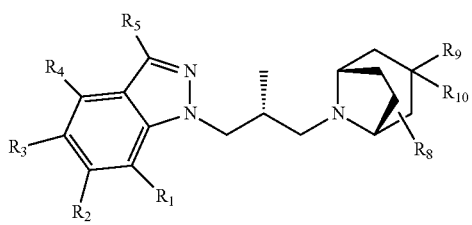

or a pharmaceutically acceptable salt thereof, wherein:
$R_1$, $R_2$, $R_3$, and $R_4$ are each independently selected from the group consisting of hydrogen, halogen, hydroxy, optionally substituted $C_{1-6}$ alkyl, optionally substituted $C_{2-6}$ alkenyl, optionally substituted $C_{2-6}$ alkynyl, and optionally substituted $C_{1-6}$ alkoxy;
$R_5$ is selected from the group consisting of hydrogen, halogen, hydroxy, optionally substituted $C_{1-6}$ alkyl, optionally substituted $C_{2-6}$ alkenyl, optionally substituted $C_{2-6}$ alkynyl, and optionally substituted $C_{1-6}$ alkoxy;
$R_8$ is present 0, 1, or 2 times, and is independently selected from the group consisting of halogen, hydroxy, optionally substituted $C_{1-6}$ alkyl, and optionally substituted —O—$C_{1-6}$ alkyl;
$R_9$ is selected from the group consisting of optionally substituted $C_{1-6}$ alkoxy, optionally substituted $C_{1-6}$ alkoxy-$C_{1-6}$ alkyl, optionally substituted $C_{2-6}$ alkenyl, optionally substituted $C_{2-6}$ alkynyl, optionally substituted $C_{2-6}$ alkenyloxy, optionally substituted $C_{2-6}$ alkynyloxy, optionally substituted $C_{1-6}$ heteroalkyl, optionally substituted $C_{3-6}$ cycloalkyl-$C_{1-6}$ alkyl, optionally substituted $C_{3-6}$ cycloalkenyl-$C_{1-6}$ alkyl, and optionally substituted $C_{3-6}$ cycloalkyloxy; and
$R_{10}$ is hydrogen;
or $R_9$ and $R_{10}$ together form an optionally substituted $C_{1-6}$ alkoxy-$C_{1-6}$ alkylidene.

2. The compound or pharmaceutically acceptable salt of claim 1, wherein the compound of formula (I) is selected from a compound of formula (Ia):

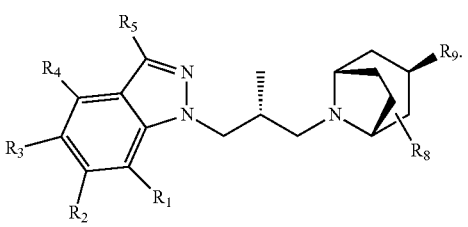

3. The compound or pharmaceutically acceptable salt of claim 1, wherein $R_1$, $R_2$, $R_3$, and $R_4$ are each independently selected from the group consisting of hydrogen, halogen, optionally substituted $C_{1-6}$ alkyl, and optionally substituted $C_{1-6}$ alkoxy; and
$R_9$ is selected from the group consisting of optionally substituted $C_{1-6}$ alkoxy, optionally substituted $C_{1-6}$ alkoxy-$C_{1-6}$ alkyl, optionally substituted $C_{2-6}$ alkenyl, optionally substituted $C_{2-6}$ alkynyl, optionally substituted $C_{2-6}$ alkenyloxy, optionally substituted $C_{2-6}$ alkynyloxy, optionally substituted $C_{1-6}$ heteroalkyl, optionally substituted $C_{3-6}$ cycloalkyl-$C_{1-6}$ alkyl, optionally substituted $C_{3-6}$ cycloalkenyl-$C_{1-6}$ alkyl, and optionally substituted $C_{3-6}$ cycloalkyloxy.

4. The compound or pharmaceutically acceptable salt of claim 3, wherein $R_1$ is hydrogen, and $R_2$, $R_3$, and $R_4$ are each independently selected from the group consisting of hydrogen, halogen, optionally substituted $C_{1-6}$ alkyl, and optionally substituted $C_{1-6}$ alkoxy.

5. The compound or pharmaceutically acceptable salt of claim 1, wherein $R_1$, $R_2$, $R_3$, and $R_4$ are independently selected from the group consisting of hydrogen, Br, F, Cl, —$CH_3$, —$CF_3$, —$CH_2OH$, and —$OCH_3$.

6. The compound or pharmaceutically acceptable salt of claim 5, wherein $R_1$, $R_3$, and $R_4$ are hydrogen, and $R_2$ is selected from the group consisting of hydrogen, F, —$CH_3$, —$CF_3$, —$CH_2OH$, and —$OCH_3$.

7. The compound or pharmaceutically acceptable salt of claim 6, wherein $R_2$ is hydrogen, F or —$CH_3$.

8. The compound or pharmaceutically acceptable salt of claim 1, wherein $R_5$ is hydrogen or methyl.

9. The compound or pharmaceutically acceptable salt of claim 1, wherein $R_9$ is selected from the group consisting of $C_{1-6}$ alkoxy, optionally substituted $C_{3-6}$ cycloalkyl-$C_{1-6}$ alkoxy, $C_{1-6}$ alkoxy-$C_{1-6}$ alkyl, $C_{2-6}$ alkenyloxy, $C_{2-6}$ alkynyloxy, and $C_{3-6}$ cycloalkyloxy.

10. The compound or pharmaceutically acceptable salt of claim 1, wherein $R_9$ is selected from the group consisting of propoxy, cyclopropylmethoxy, cyclobutylmethoxy, allyloxy, methoxyethyl, ethoxyethyl, cyclopentyloxy, and prop-2-ynyloxy.

11. The compound or pharmaceutically acceptable salt of claim 10, wherein $R_9$ is selected from the group consisting of cyclopropylmethoxy, allyloxy, and methoxyethyl.

12. The compound or pharmaceutically acceptable salt of claim 1, wherein $R_9$ and $R_{10}$ together form optionally substituted $C_{1-6}$ alkoxy-$C_{1-6}$ alkylidene.

13. The compound or pharmaceutically acceptable salt of claim 12, wherein optionally substituted $C_{1-6}$ alkoxy-$C_{1-6}$ alkylidene is methoxyethylidene.

14. A compound or pharmaceutically acceptable salt, wherein the compound is selected from the group consisting of:
1-(3-((1R,3R,5S)-3-(cyclopropylmethoxy)-8-azabicyclo [3.2.1]octan-8-yl)-2-methylpropyl)-1H-indazole;
1-((R)-3-((1R,3R,5S)-3-(cyclopropylmethoxy)-8-azabicyclo[3.2.1]octan-8-yl)-2-methylpropyl)-1H-indazole;
1-((R)-3-((1R,3R,5S)-3-(2-Methoxyethyl)-8-azabicyclo [3.2.1]octan-8-yl)-2-methylpropyl)-1H-indazole;
1-((R)-3-(3-(Cyclopropylmethoxy)-8-aza-bicyclo [3.2.1] octan-8-yl)-2-methylpropyl)-6-methyl-1H-indazole;
1-((R)-3-((1R,3R,5S)-3-(Allyloxy)-8-azabicyclo [3.2.1] octan-8-yl)-2-methylpropyl)-1H-indazole;
1-((R)-3-(3-(Cyclopropylmethoxy)-8-aza-bicyclo [3.2.1] octan-8-yl)-2-methylpropyl)-6-(trifluoromethyl)-1H-indazole;

1-((R)-3-(3-(Cyclopropylmethoxy)-8-aza-bicyclo[3.2.1]octan-8-yl)-2-methylpropyl)-6-fluoro-1H-indazole;

1-((R)-3-(3-(Allyloxy)-8-aza-bicyclo [3.2.1]octan-8-yl)-2-methylpropyl)-6-fluoro-1H-indazole;

1-((R)-3-(3-(2-Methoxyethyl)-8-aza-bicyclo[3.2.1]octan-8-yl)-2-methylpropyl)-6-fluoro-1H-indazole;

(1-((R)-3-((1R,3R,5S)-3-(cyclopropylmethoxy)-8-azabicyclo[3.2.1]octan-8-yl)-2-methylpropyl)-1H-indazol-6-yl)methanol;

1-((R)-3-(3-(cyclopropylmethoxy)-8-aza-bicyclo[3.2.1]octan-8-yl)-2-methylpropyl)-6-methoxy-1H-indazole;

1-((R)-3-((1R,3R,5S)-3-(2-methoxyethyl)-8-azabicyclo[3.2.1]octan-8-yl)-2-methylpropyl)-6-methyl-1H-indazole;

1-((R)-3-((1R,3R,5S)-3-(2-methoxyethyl)-8-azabicyclo[3.2.1]octan-8-yl)-2-methylpropyl)-6-methoxy-1H-indazole;

1-((R)-3-((1R,3R,5S)-3-(cyclopentyloxy)-8-azabicyclo[3.2.1]octan-8-yl)-2-methylpropyl)-1H-indazole;

1-((R)-3-(3-(cyclobutylmethoxy)-8-aza-bicyclo[3.2.1]octan-8-yl)-2-methylpropyl)-1H-indazole;

1-((R)-3-(3-(cyclopropylmethoxy)-8-aza-bicyclo [3.2.1]octan-8-yl)-2-methylpropyl)-3-methyl-1H-indazole;

1-((R)-3-(3-(cyclopropylmethoxy)-8-aza-bicyclo[3.2.1]octan-8-yl)-2-methylpropyl)-7-methyl-1H-indazole;

1-((R)-3-((1R,3R,5S)-3-(prop-2-ynyloxy)-8-azabicyclo[3.2.1]octan-8-yl)-2-methylpropyl)-1H-indazole;

1-((R)-3-((1R,3R,5S)-3-(propoxy)-8-azabicyclo[3.2.1]octan-8-yl)-2-methylpropyl)-1H-indazole;

1-((R)-3-((1R,3R,5S)-3-(2-methoxyethylidene)-8-azabicyclo[3.2.1]octan-8-yl)-2-methylpropyl)-1H-indazole;

1-((R)-3-(3-(cyclopropylmethoxy)-8-aza-bicyclo[3.2.1]octan-8-yl)-2-methylpropyl)-5-methyl-1H-indazole;

1-((R)-3-((1R,3R,5S)-3-(prop-2-ynyloxy)-8-azabicyclo[3.2.1]octan-8-yl)-2-methylpropyl)-6-methoxy-1H-indazole;

1-((R)-3-((1R,3R,5S)-3-(2-ethoxyethyl)-8-azabicyclo[3.2.1]octan-8-yl)-2-methylpropyl)-1H-indazole; and 1-((R)-3-((1R,3R,5S)-3-(2-ethoxyethyl)-8-azabicyclo[3.2.1]octan-8-yl)-2-methylpropyl)-6-methyl-1H-indazole.

15. A pharmaceutical composition comprising the compound, or pharmaceutically acceptable salt of claim 1, and a pharmaceutically acceptable excipient.

16. The compound or pharmaceutically acceptable salt according to claim 1, wherein $R_1$, $R_3$, $R_4$, and $R_5$ are hydrogen, and $R_2$ is selected from the group consisting of hydrogen, F, —CH$_3$, —CF$_3$, —CH$_2$OH, and —OCH$_3$; and $R_9$ is selected from the group consisting of $C_{1-6}$ alkoxy, optionally substituted $C_{3-6}$ cycloalkyl-$C_{1-6}$ alkoxy, $C_{1-6}$ alkoxy-$C_{1-6}$ alkyl, $C_{2-6}$ alkenyloxy, $C_{2-6}$ alkynyloxy, and $C_{3-6}$ cycloalkyloxy, or $R_9$ and $R_{10}$ together form optionally substituted $C_{1-6}$ alkoxy-$C_{1-6}$ alkylidene.

17. The compound or pharmaceutically acceptable salt of claim 11, wherein $R_9$ is cyclopropylmethoxy.

18. The compound or pharmaceutically acceptable salt of claim 14, wherein the compound is selected from the group consisting of:

1-((R)-3-((1R,3R,5S)-3-(cyclopropylmethoxy)-8-azabicyclo[3.2.1]octan-8-yl)-2-methylpropyl)-1H-indazole;

1-((R)-3-((1R,3R,5S)-3-(2-Methoxyethyl)-8-azabicyclo[3.2.1]octan-8-yl)-2-methylpropyl)-1H-indazole;

1-((R)-3-(3-(Cyclopropylmethoxy)-8-aza-bicyclo[3.2.1]octan-8-yl)-2-methylpropyl)-6-methyl-1H-indazole; and 1-((R)-3-((1R,3R,5S)-3-(Allyloxy)-8-azabicyclo[3.2.1]octan-8-yl)-2-methylpropyl)-1H-indazole.

19. The compound or pharmaceutically acceptable salt of claim 18, wherein the compound is 1-((R)-3-((1R,3R,5S)-3-(cyclopropylmethoxy)-8-azabicyclo[3.2.1]octan-8-yl)-2-methylpropyl)-1H-indazole.

20. A compound or a pharmaceutically acceptable salt thereof, wherein the compound is 1-(3-((1R,3R,5S)-3-(cyclopropylmethoxy)-8-azabicyclo[3.2.1]octan-8-yl)-2-methylpropyl)-1H-indazole.

\* \* \* \* \*